United States Patent
Lee et al.

(10) Patent No.: US 11,976,059 B2
(45) Date of Patent: May 7, 2024

(54) ISOINDOLIN-1-ON DERIVATIVE, METHOD FOR PREPARING SAME, AND PHARMACEUTICAL COMPOSITION COMPRISING SAME AS EFFECTIVE COMPONENT FOR PREVENTING OR TREATING CANCER

(71) Applicant: KOREA RESEARCH INSTITUTE OF CHEMICAL TECHNOLOGY, Daejeon (KR)

(72) Inventors: Kwangho Lee, Daejeon (KR); Gildon Choi, Daejeon (KR); Seoyoung Lee, Daejeon (KR); Jiwon Kim, Daejeon (KR); Byoung Chul Cho, Daejeon (KR); Chae Won Park, Daejeon (KR); Jiyeon Yun, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 625 days.

(21) Appl. No.: 17/268,869

(22) PCT Filed: Aug. 12, 2019

(86) PCT No.: PCT/KR2019/010202
§ 371 (c)(1),
(2) Date: Feb. 16, 2021

(87) PCT Pub. No.: WO2020/036386
PCT Pub. Date: Feb. 20, 2020

(65) Prior Publication Data
US 2021/0332029 A1 Oct. 28, 2021

(30) Foreign Application Priority Data

Aug. 16, 2018 (KR) ........................ 10-2018-0095574

(51) Int. Cl.
| | | |
|---|---|---|
| *C07D 401/14* | (2006.01) | |
| *A61K 45/06* | (2006.01) | |
| *C07D 403/06* | (2006.01) | |
| *C07D 403/14* | (2006.01) | |
| *C07D 471/04* | (2006.01) | |

(52) U.S. Cl.
CPC ............ *C07D 403/06* (2013.01); *A61K 45/06* (2013.01); *C07D 401/14* (2013.01); *C07D 403/14* (2013.01); *C07D 471/04* (2013.01)

(58) Field of Classification Search
CPC ............................ C07D 403/06; C07D 401/14
See application file for complete search history.

(56) References Cited

U.S. PATENT DOCUMENTS

2011/0269768 A1   11/2011   Kinney et al.

FOREIGN PATENT DOCUMENTS

| KR | 20070047807 A | 5/2007 |
|---|---|---|
| KR | 20120113219 A | 10/2012 |
| WO | WO 2006/015060 A2 | 2/2006 |
| WO | WO 2010/053732 A1 | 5/2010 |
| WO | WO 2011/079091 A1 | 6/2011 |

OTHER PUBLICATIONS

Majumdar, et al. Inorg. Chem. 2017, 56, 8889-8899.*
Lala, et al. Cancer and Metastasis Reviews 17:91-106, 1998.*
Golub, et al. Science 286, 531 (1999).*
Cancer [online] retrieved from the internet on Oct. 5, 2023, URL: https://medlineplus.gov/cancer.html.*
Balak et al., "Novel D761Y and Common Secondary T790M Mutations in Epidermal Growth Factor Receptor—Mutant Lung Adenocarcinomas with Acquired Resistance to Kinase Inhibitors," *Clin Cancer Res.* 12.21: 6494-6501, Nov. 2006.
Cheng et al., "Highly diastereoselective reactions of 2-lithiated indoles with chiral N-tert-butanesulfinyl aldimines for the synthesis of chiral (2-indolyl) methanamine derivatives," *Tetrahedron: Asymmetry* 18.15: 1833-1843, Aug. 2007.
Engelman et al., "MET Amplification Leads to Gefitinib Resistance in Lung Cancer by Activating ERBB3 Signaling," *Science* 316: 1039-1043, May 2007.
Fukuoka et al., "Multi-Institutional Randomized Phase II Trial of Gefitinib for Previously Treated Patients with Advanced Non-Small-Cell Lung Cancer," *J Clin Oncol.* 21.12: 2237-2246, Jun. 2003.
International Search Report and Written Opinion for PCT/KR2019/010202, dated Nov. 15, 2019, ISA Korean Intellectual Property Office, 8 pages (with English translation of International Search Report, 4 pages).
Jia et al., "Overcoming EGFR (T790M) and EGFR (C797S) Resistance with Mutant-Selective Allosteric Inhibitors," *Nature* 534. 7605: 129-132, Jun. 2016.
Kobayashi et al., "EGFR Mutation and Resistance of Non-Small-Cell Lung Cancer to Gefitinib," *N Engl J Med.* 352.8: 786-792, Feb. 2005.
Kosaka et al., "Analysis of Epidermal Growth Factor Receptor Gene Mutation in Patients with Non-Small Cell Lung Cancer and Acquired Resistance to Gefitinib," *Clin Cancer Res* 12.19: 5764-5769, Oct. 2006.
Kris et al., "Efficacy of Gefitinib, an Inhibitor of the Epidermal Growth Factor Receptor Tyrosine Kinase, in Symptomatic Patients with Non-Small Cell Lung Cancer," *JAMA* 290.16: 2149-2158, Oct. 2003.
Lynch et al., "Activating Mutations in the Epidermal Growth Factor Receptor Underlying Responsiveness of Non-Small-Cell Lung Cancer to Gefitinib," *N Engl J Med.* 350.21: 2129-2139, May 2004.

(Continued)

*Primary Examiner* — Shawquia Jackson
(74) *Attorney, Agent, or Firm* — Klarquist Sparkman, LLP

(57) ABSTRACT

The present invention relates to an isoindolin-1-on derivative, a method for preparing same, and a pharmaceutical composition comprising same as an effective component for preventing or treating tumors, wherein the isoindolin-1-on derivative exhibits a high inhibitory effect on EGFR mutations, and thus can be beneficially used for the treatment of EGFR-mutated tumors, and the isoindolin-1-on derivative exhibits a significant synergistic effect when co-administered, and thus can be beneficially used in concomitant therapy.

19 Claims, 14 Drawing Sheets

(56) References Cited

OTHER PUBLICATIONS

Paez et al., "EGFR Mutations in Lung Cancer: Correlation with Clinical Response to Gefitinib Therapy," *Science* 304.5676: 1497-1500, Jun. 2004.

Pao et al., "KRAS Mutations and Primary Resistance of Lung Adenocarcinomas to Gefitinib or Erlotinib," *PLoS Medicine* 2.1: e17, Jan. 2005 (6 pages).

Renteria-Gomez et al., "Synthesis of 2-Tetrazolylmethyl-isoindolin-1-ones via a One-Pot Ugi-Azide/(N-Acylation/exo-Diels-Alder)/Dehydration Process," *ACS Omega* 1: 943-951, Nov. 2016.

Sharma et al., "Epidermal Growth Factor Receptor Mutations in Lung Cancer," *Nat Rev Cancer* 7.3: 169-181, Mar. 2007.

Thress et al., "Acquired EGFR C797S Mutation Mediates Resistance to AZD9291 in Non-Small Cell Lung Cancer Harboring EGFR T790M," *Nat Med.* 21.6: 560-562, Jun. 2015.

Tsao et al., "Erlotinib in Lung Cancer—Molecular and Clinical Predictor of Outcome," *N Engl J Med.* 353.2: 133-144, Jul. 2005.

\* cited by examiner

【Figure 1a】
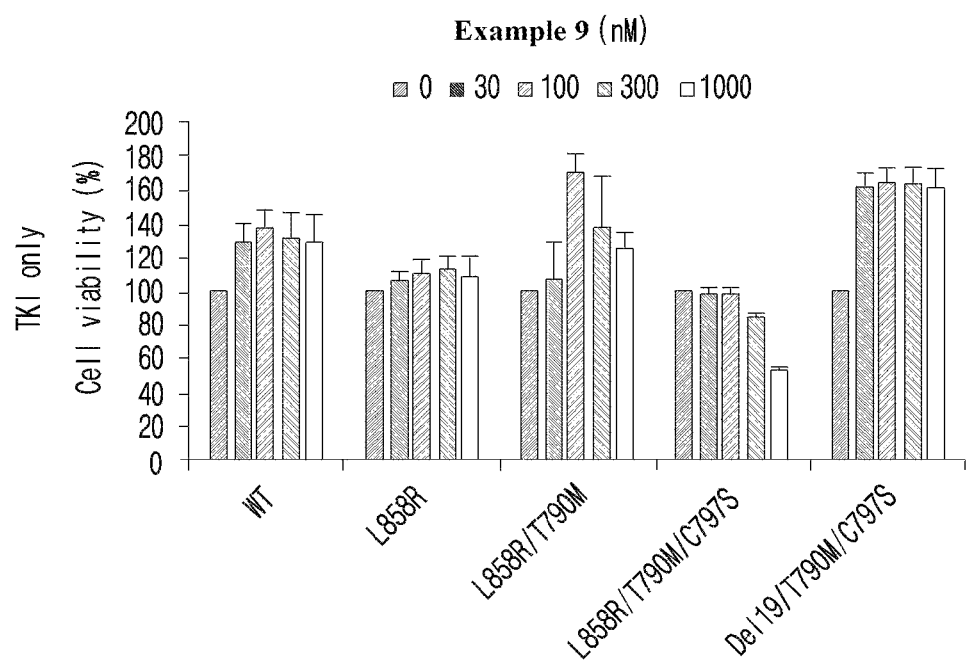

【Figure 1b】
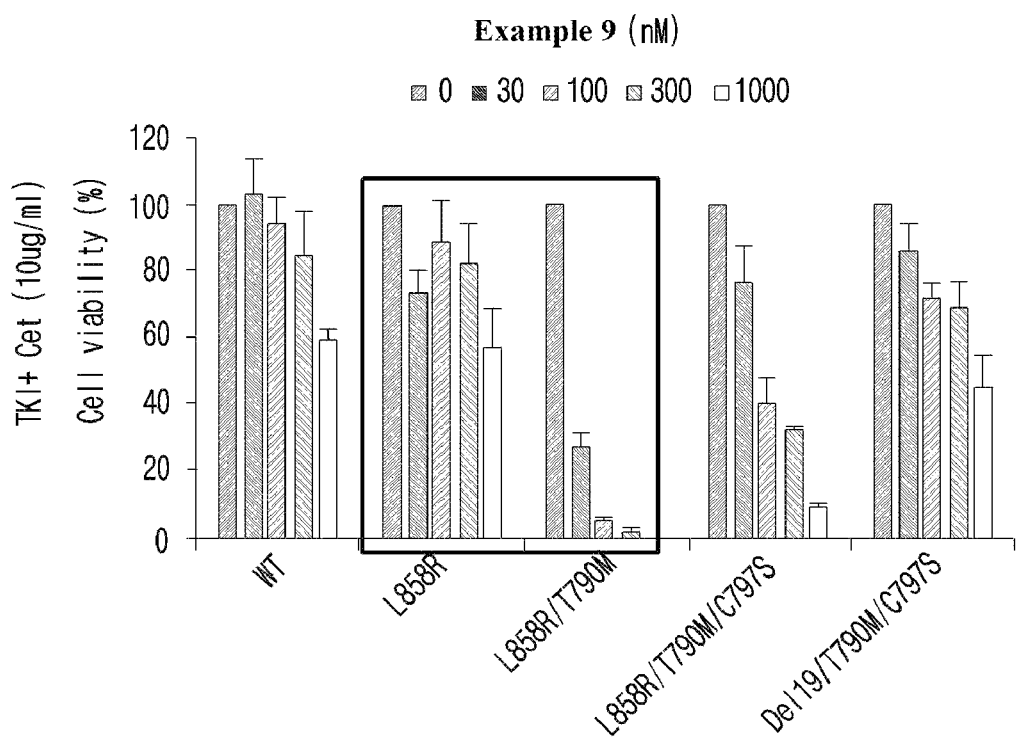

[Figure 2a]
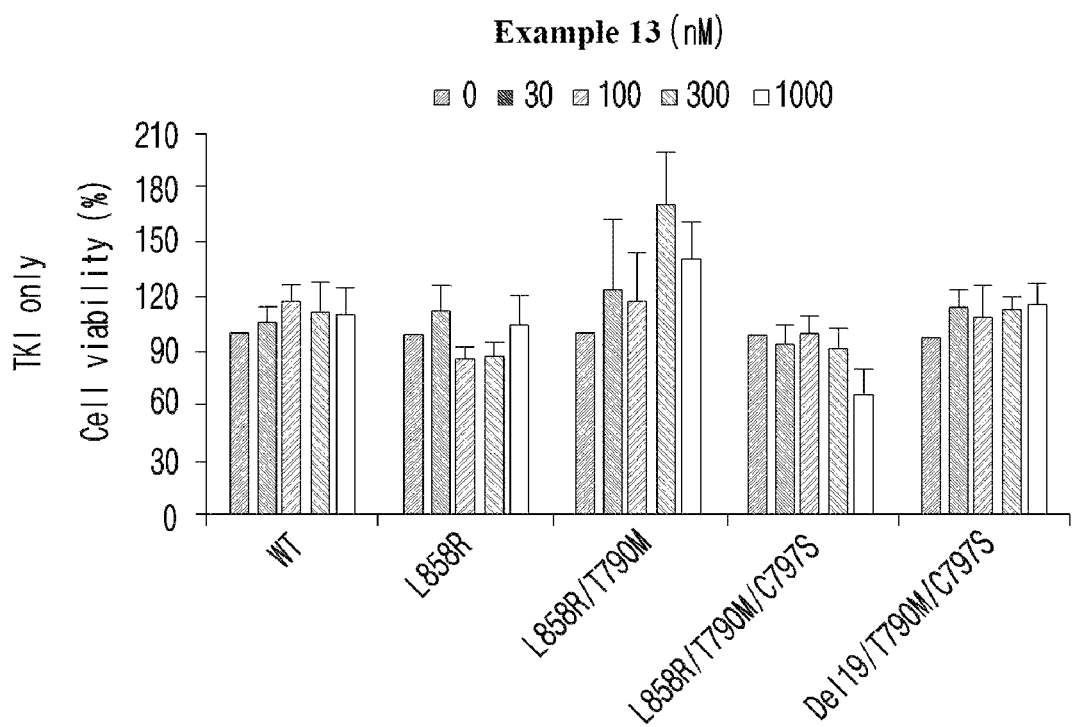

【Figure 2b】
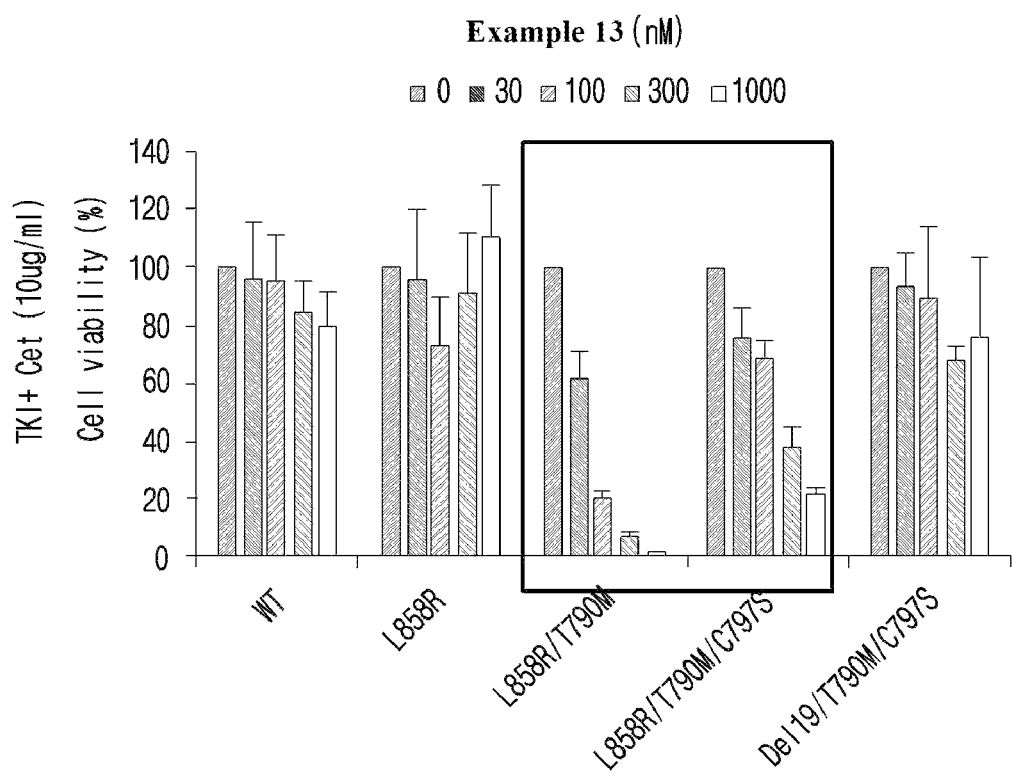

【Figure 3a】
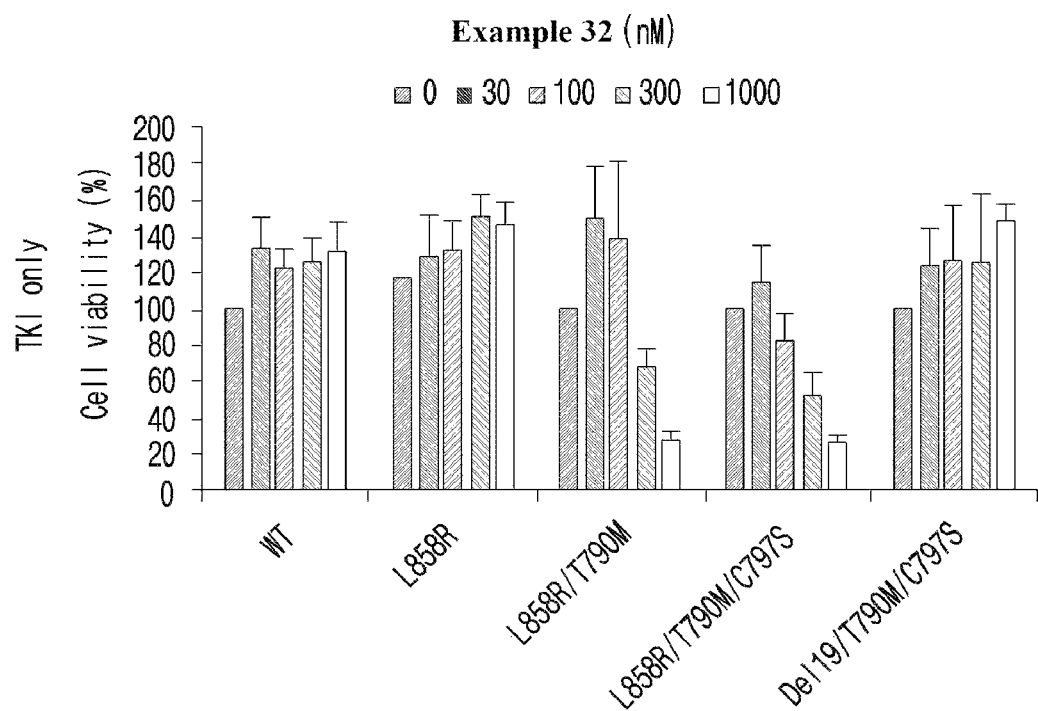

【Figure 3b】
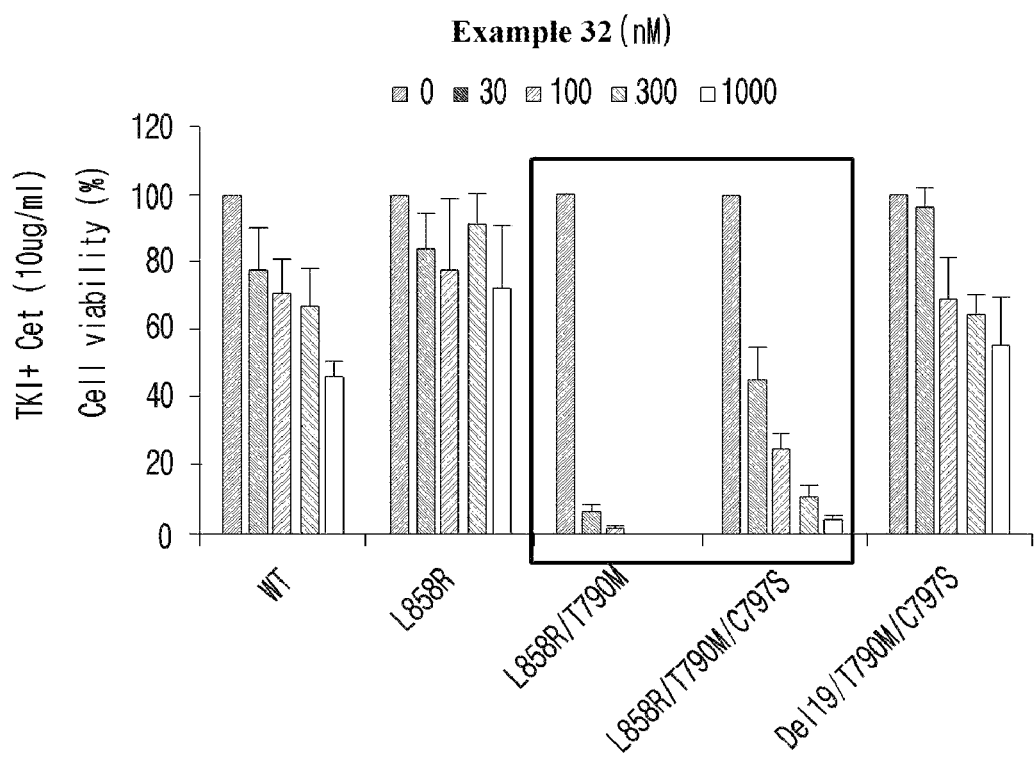

【Figure 4a】
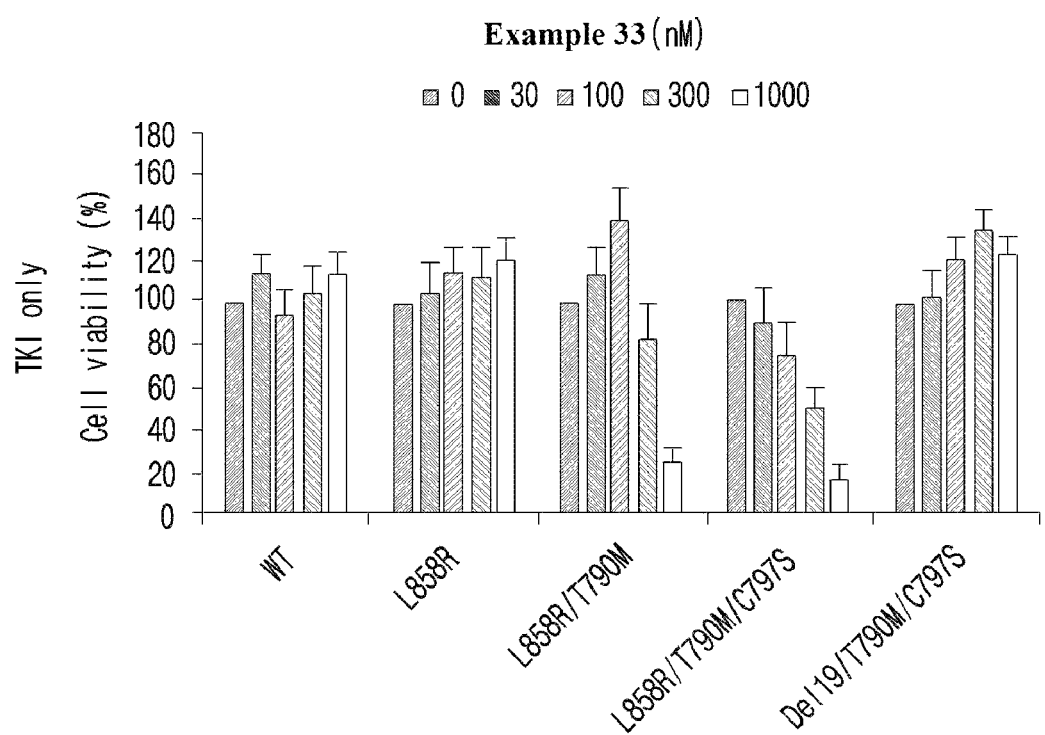

【Figure 4b】
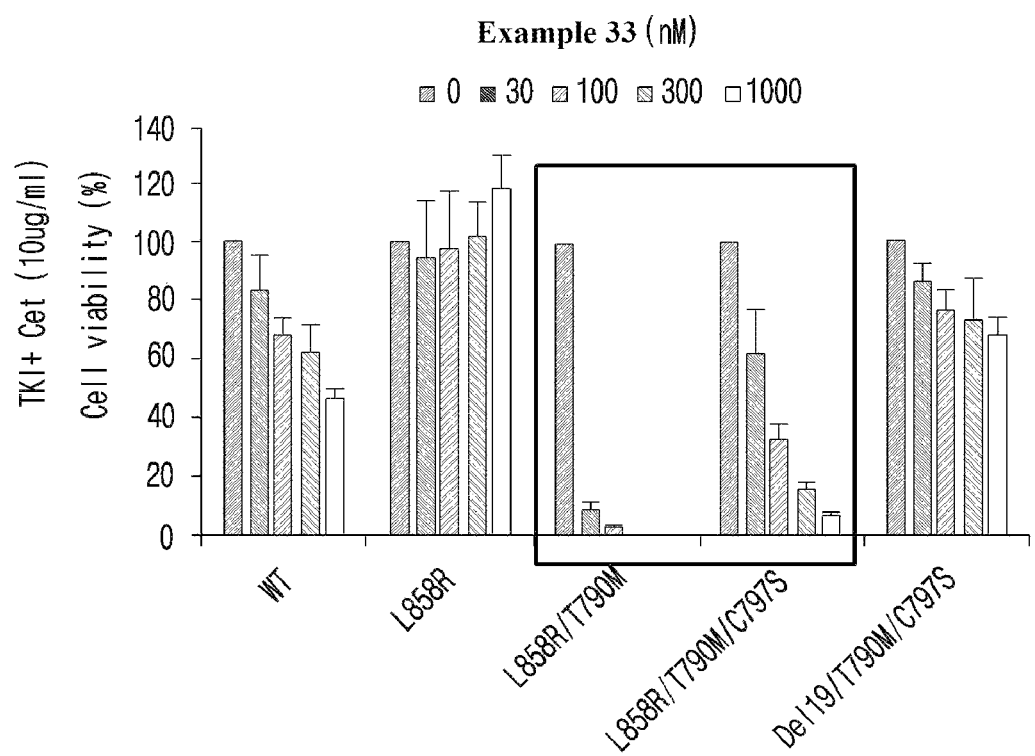

【Figure 5a】
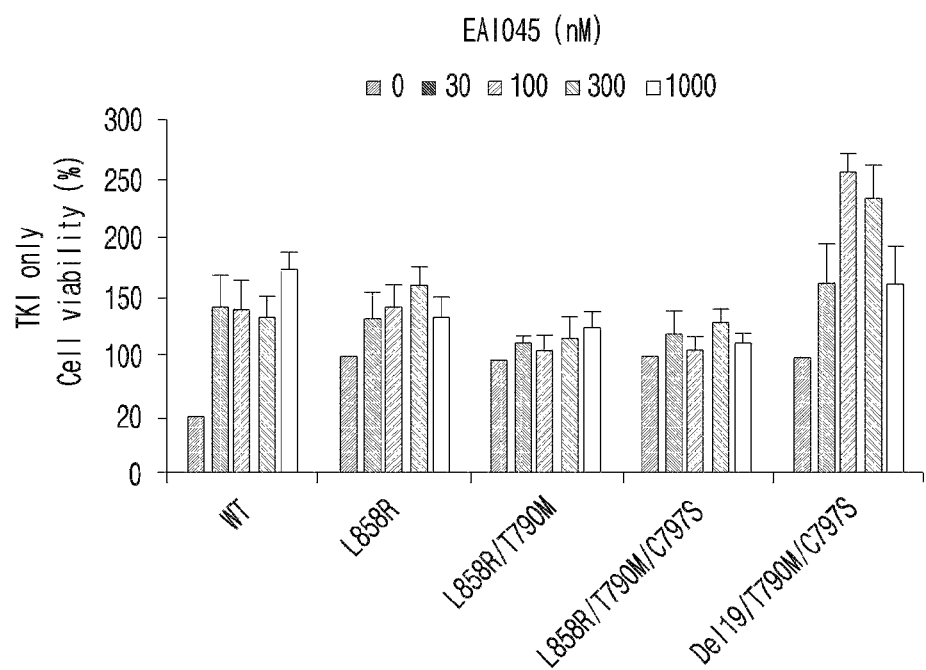

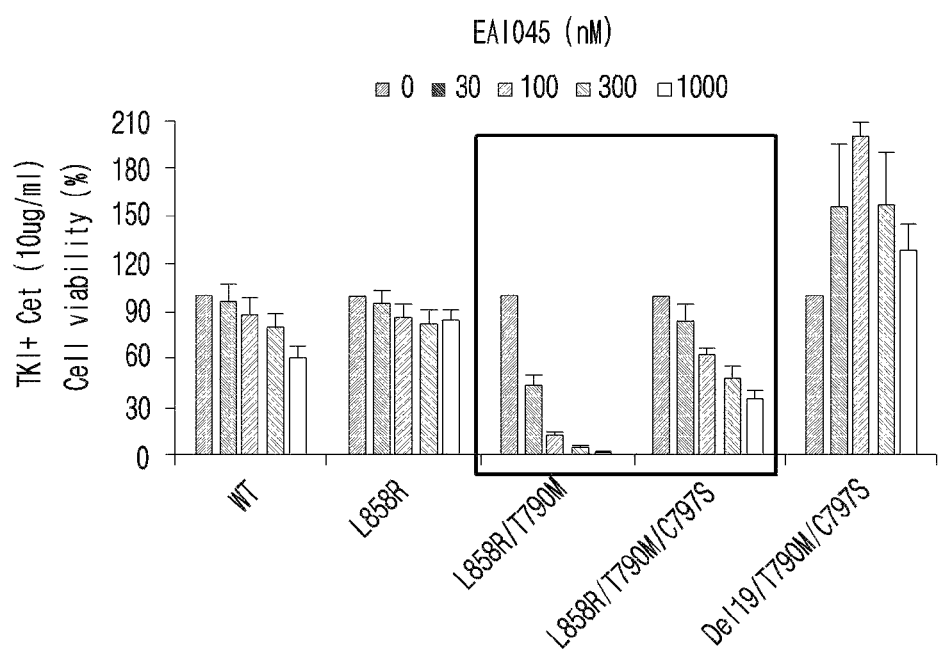
【Figure 5b】

[Figure 6a]
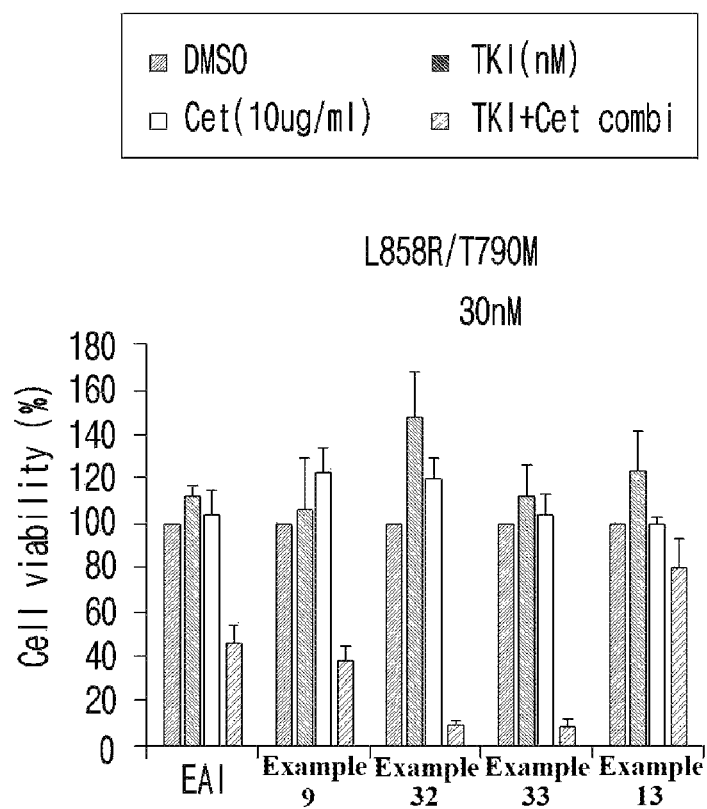

【Figure 6b】
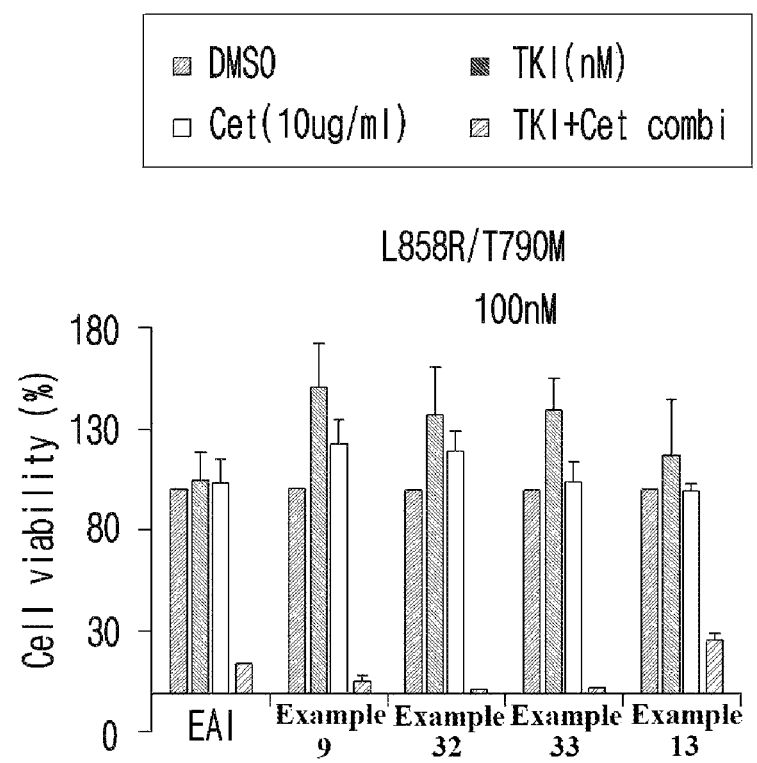

[Figure 7a]
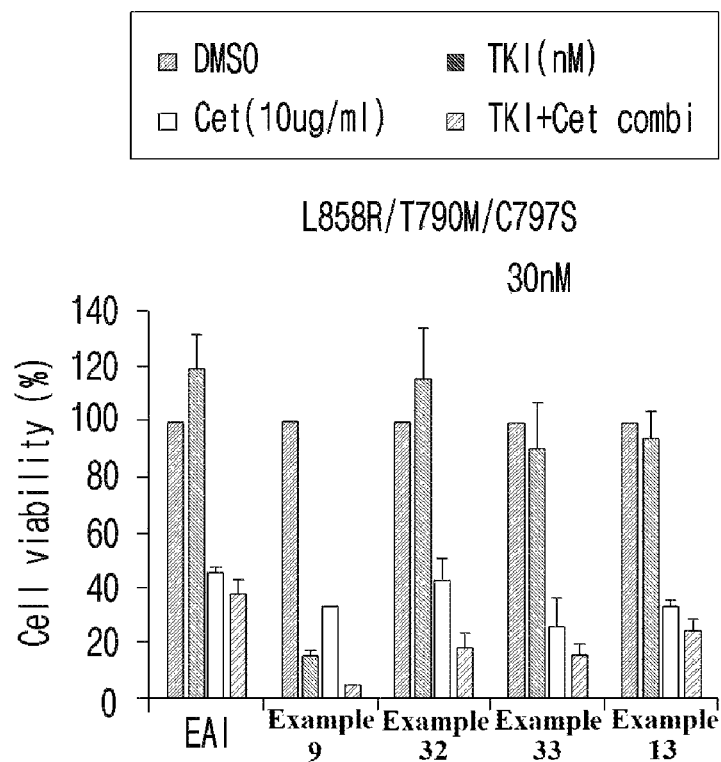

【Figure 7b】
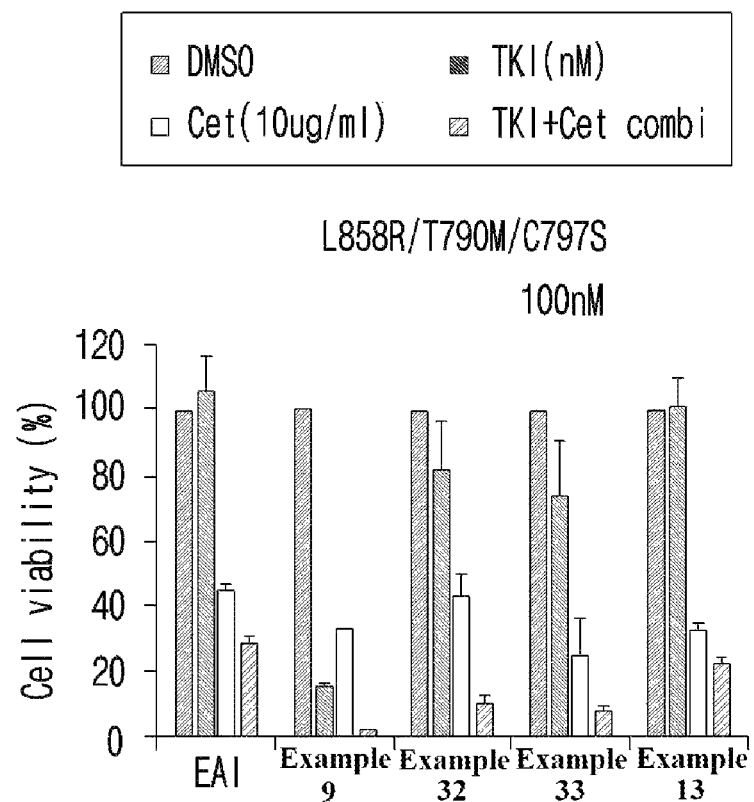

ISOINDOLIN-1-ON DERIVATIVE, METHOD FOR PREPARING SAME, AND PHARMACEUTICAL COMPOSITION COMPRISING SAME AS EFFECTIVE COMPONENT FOR PREVENTING OR TREATING CANCER

CROSS-REFERENCE TO RELATED APPLICATIONS

This is the U.S. National Stage of International Application No. PCT/KR2019/010202, filed on Aug. 12, 2019, which in turn claims the benefit of priority from Korean Patent Application No. 10-2018-0095574, filed on Aug. 16, 2018. The contents of each of which are incorporated herein by reference in their entirety.

BACKGROUND OF THE INVENTION

1. Field of the Invention

The present invention relates to an isoindolin-1-one derivative, a method for preparing the same, and a pharmaceutical composition comprising the same as an active ingredient for preventing or treating cancer.

2. Description of the Related Art

The incidence of cancer is related to various environmental factors including chemicals, radiation, and viruses, as well as changes in oncogenes, tumor suppressor genes, and genes related to apoptosis and DNA repair. Recent understanding of the molecular mechanisms of cancer has enabled targeted anticancer therapy, a new treatment.

Targeted agents are generally made to target the molecules that cancer cells characteristically have to show their effectiveness. Molecular targets are genes related to cancer cell signal transduction pathway, angiogenesis, matrix, cell cycle regulator, and apoptosis. Currently, 'signal transduction pathway inhibitors' including tyrosine kinase inhibitors and 'angiogenesis inhibitors' are used as important targeted agents in cancer treatment.

Protein tyrosine kinase has been known to play an important role in many malignant tumors.

In particular, epidermal growth factor receptor (EGFR), a receptor tyrosine kinase of the erbB family, is abnormally activated in many epithelial cell tumors including non-small cell lung carcinoma (NSCLC), breast cancer, glioma, squamous cell carcinoma of the head and neck, colon cancer, rectal carcinoma, head and neck cancer, stomach cancer, and prostate cancer, and it has been known that the activation of the EGFR-tyrosine kinase causes continuous cell proliferation, invasion of surrounding tissues, distant metastasis, blood vessel formation, and increases cell survival.

Particularly, EGFR is one of the ErbB tyrosine kinase receptors family (EGFR, HER-2, ErbB-3, ErbB-4), and is a transmembrane tyrosine kinase having an intracellular domain including an extracellular ligand-binding domain and a tyrosine kinase domain. When a ligand is bound to a receptor that forms a homodimer or heterodimer, the intracellular tyrosine kinase is activated, and the signal stimulated by EGFR activates phosphatidylinositol 3-kinase (PI3K/AKT/mTOR, RAS/RAF/MAPK, JAK/STAT) signaling pathway (Nat Rev Cancer 2007; 7:169-81).

In particular, EGFR is overexpressed in more than half of non-small cell lung cancer (NSCLC), and many studies have been conducted with EGFR as a target of treatment. EGFR TKI (tyrosine kinase inhibitor), which inhibits EGFR tyrosine kinase activity, has been developed, and the representative drugs include gefitinib (IRESSA™), erlotinib (TARCEVA™), and lapatinib (TYKERB™, TYVERB™).

On the other hand, in 2004, it was reported that the activation mutation of EGFR is correlated with the response to gefitinib therapy in non-small-cell lung cancer (NSCLC) (Science [2004] Vol. 304, 1497-500 and New England Journal of Medicine [2004] Vol. 350, 2129-39).

Particularly, the EGFR mutation is largely classified into a sensitizing mutation and a resistant mutation, and the deletion of exon 19 and the L858R point mutation of exon 21 are the most important sensitizing mutations, accounting for about 85-90%, and the exon 19 del mutation is known to have better sensitivity to TKI. On the other hand, the T790M point mutation of exon 20 is the most important resistant mutation and is known to be found in more than 50% of acquired resistance patients (Clin Cancer Res 2006; 12:6494-6501.).

Somatic mutations identified so far include intraframe deletion in exon 19 or insertions in exon 20, as well as point mutations in which a single nucleic acid residue is modified in the expressed protein (e.g., L858R, G719S, G719C, G719A, L861Q) (Fukuoka et al. JCO 2003; Kris et al JAMA 2003 and Shepherd et al NEJM 2005).

Despite the initial clinical effects of gefitinib/erlotinib on NSCLC patients with EGFR mutations, advanced cancer eventually develops in most patients during therapy with these agents. Early studies of relapsed specimens identified a secondary EGFR mutation, T790M, which makes gefitinib and erlotinib ineffective inhibitors of EGFR kinase activity (Kobayashi et al NEJM 2005 and Pao et al PLOS Medicine 2005). It was demonstrated in subsequent studies that the EGFR T790M mutation was found in approximately 50% (24/48) of tumors of patients who acquired resistance to gefitinib or erlotinib (Kosaka et al CCR 2006; Balak et al CCR 2006 and Engelman et al Science 2007). This secondary genetic modification occurs at a position similar to the 'gatekeeper' residue and the secondary resistance allele associated with it in patients treated with kinase inhibitors (e.g., T315I in ABL in imatinib resistant CML).

It has long been known that the EGFR mutation, EGFR_del19 or EGFR_L858R, is the major cause of non-small cell lung cancer and head and neck cancer, and their therapeutic drugs, Iressa and Tarceva, have been developed and are currently used in clinic. However, when these drugs were used in patients, acquired resistance was observed, resulting in EGFR secondary mutations based on the structure of the drug, and it was also found that this is the main cause of actual drug resistance. When the first generation EGFR inhibitors are used for an average of 10 months, the acquired resistance, the T790M mutation located in the gatekeeper of the EGFR kinase, occurs, and the first generation EGFR inhibitors are not effective. That is, EGFR_del19_T790M or EGFR_L858R_T790M double mutation occurs, and the conventional therapeutic agents do not show efficacy.

Based on these facts, the need for the development of $2^{nd}$ and $3^{rd}$ generation drugs with excellent drug efficacy and new structures emerged.

In the past 10 years, various $3^{rd}$ generation new drug candidates that have an effect on the double mutation of EGFR T790M have been discovered and in clinical use, and the most advanced of them is Osimertinib of AstraZeneca, a multinational pharmaceutical company. However, it has been reported that resistance to Osimertinib occurs in about 10 months, resulting in loss of the drug efficacy of Osimertinib, and in particular, resistance to triple mutations including C797S has been reported (Thress et al, Nature Medicine 2015).

Accordingly, there is a need for the development of inhibitors that exhibit relatively low inhibition of WT EGFR and higher inhibition of specific activated or resistant mutant forms of EGFR.

Gefitinib, erlotinib and afatinib, the EGFR TKIs (tyrosine kinase inhibitors), are approved therapeutic agents for non-small cell lung cancer with activating mutations in EGFR kinase. However, they have a problem that resistance to these occurs rapidly, and T790M mutations in the ATP site of the receptor frequently occur. On the other hand, recently developed mutation selective irreversible inhibitors exhibit high activity against the T790M mutation, but the efficacy can be neutralized by the acquired mutation of C797, a cysteine residue that forms a core covalent bond. Currently, most EGFR TKIs target the ATP site of kinase (Nature 2016, 534(7605), 129).

On the other hand, the enzyme activity can be promoted or suppressed through 'allosteric regulation'. Allosteric regulation is an example of a natural regulatory circuit in the metabolic process represented by feedback, and is particularly important in cell signaling pathway. When an effector molecule binds to a specific other site in a protein, the allosteric signal is transmitted to the binding site of the substrate along a pathway in the network within the molecule. In other words, allosteric regulation is the regulation of reaction capacity in biochemistry by binding of active substances to the sites other than active sites of enzymes or other proteins. At this time, an active substance that accelerates the reaction of an enzyme or protein is called an 'allosteric activator', and a substance that inhibits the reaction is called an 'allosteric inhibitor'.

Therefore, it is necessary to develop an allosteric inhibitor of EGFR TKI as a therapeutic agent with an alternative action mechanism.

SUMMARY OF THE INVENTION

It is an object of the present invention to provide an isoindolin-1-one derivative.

It is another object of the present invention to provide a method for preparing an isoindolin-1-one derivative.

It is another object of the present invention to provide a pharmaceutical composition for preventing or treating cancer comprising an isoindolin-1-one derivative as an active ingredient.

It is another object of the present invention to provide a health functional food for preventing or ameliorating cancer comprising an isoindolin-1-one derivative as an active ingredient.

To achieve the above objects, in one aspect of the present invention, the present invention provides a compound represented by formula 1, an isomer thereof, a solvate thereof, a hydrate thereof or a pharmaceutically acceptable salt thereof:

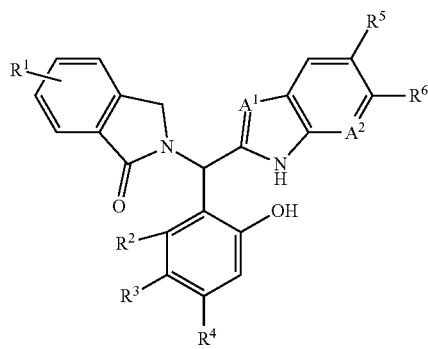

[Formula 1]

(In formula 1,
$A^1$, $A^2$, $R^1$, $R^2$, $R^3$, $R^4$, $R^5$ and $R^6$ are as defined in this specification).

In another aspect of the present invention, the present invention provides a method for preparing a compound represented by formula 1a comprising the following steps, as shown in reaction formula 1 below:

preparing a compound represented by formula 3 by reacting a compound represented by formula 5 with a compound represented by formula 4 (step 1);

preparing a compound represented by formula 2 by cyclization of the compound represented by formula 3 (step 2); and preparing a compound represented by formula 1a by reacting the compound represented by formula 2 (step 3):

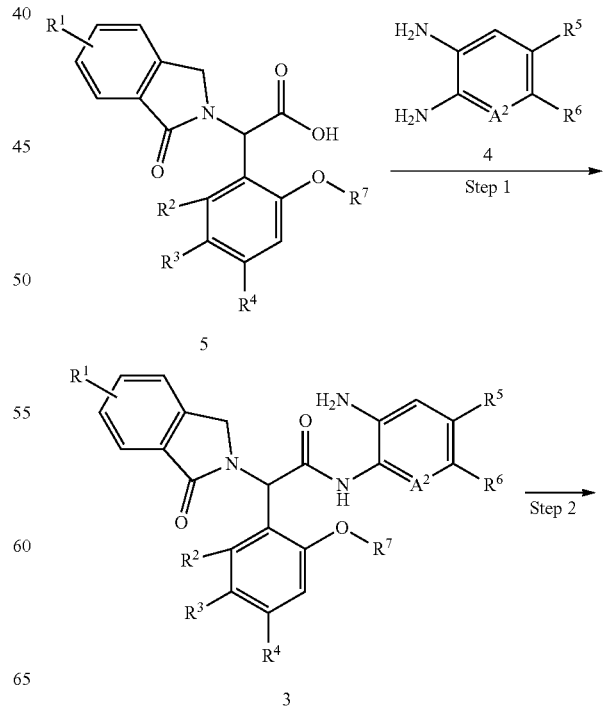

[Reaction Formula 1]

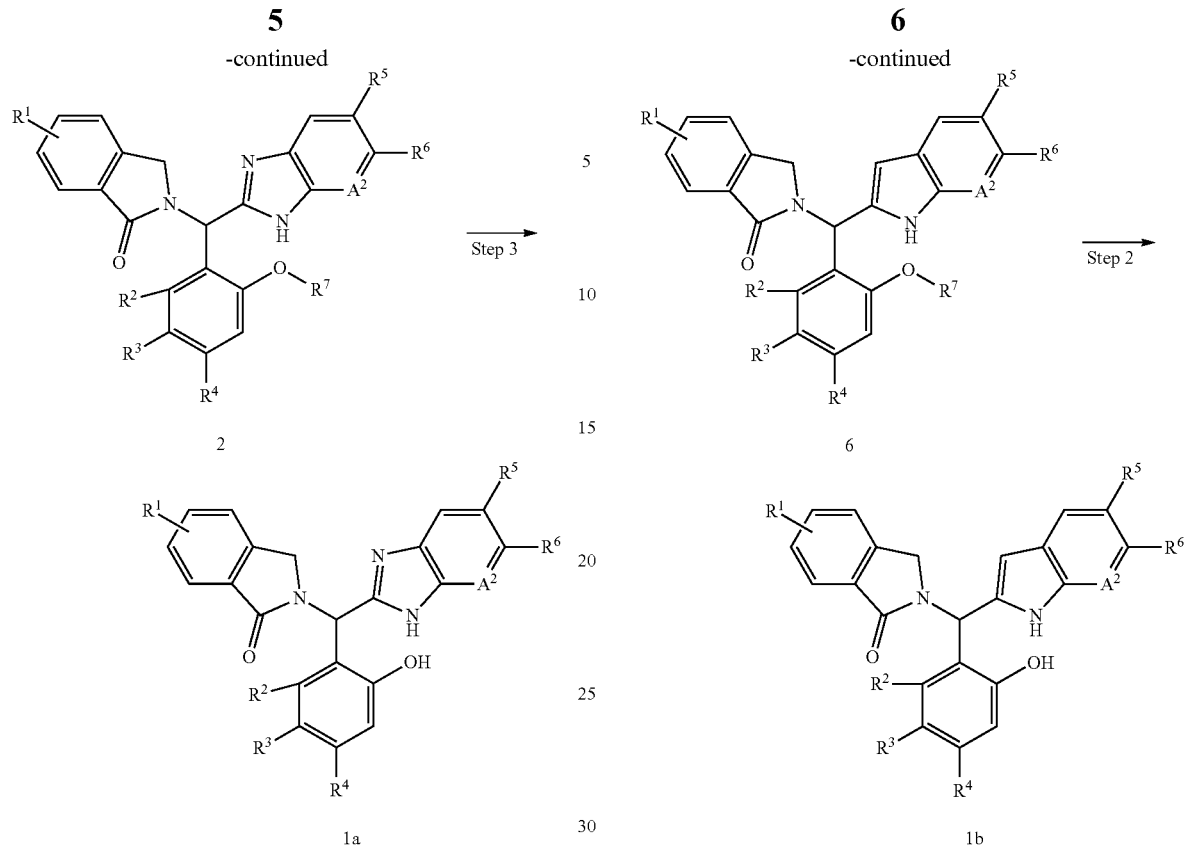

(In reaction formula 1,
A¹, A², R¹, R², R³, R⁴, R⁵, R⁶ and R⁷ are as defined in this specification; and
the compound represented by formula 1a is a derivative when A¹ is N in the compound represented by formula 1).

In another aspect of the present invention, the present invention provides a method for preparing a compound represented by formula 1b comprising the following steps, as shown in reaction formula 2 below:
  preparing a compound represented by formula 6 by reacting a compound represented by formula 8 with a compound represented by formula 7 (step 1); and
  preparing a compound represented by formula 1b by reacting the compound represented by formula 6 (step 2):

[Reaction Formula 2]

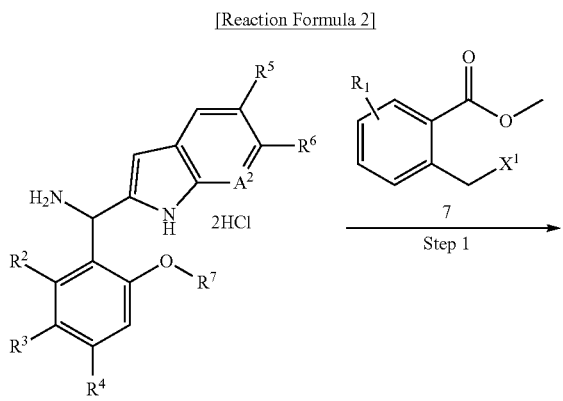

(In reaction formula 2,
A¹, A², R¹, R², R³, R⁴, R⁵, R⁶, R⁷ and X¹ are as defined in this specification; and
the compound represented by formula 1b is a derivative when A¹ is CH in the compound represented by formula 1).

In another aspect of the present invention, the present invention provides a pharmaceutical composition comprising a compound represented by formula 1, an isomer thereof, a solvate thereof or a pharmaceutically acceptable salt thereof as an active ingredient for the prevention or treatment of cancer.

In another aspect of the present invention, the present invention provides a health functional food comprising a compound represented by formula 1, an isomer thereof, a solvate thereof or a pharmaceutically acceptable salt thereof as an active ingredient for the prevention or amelioration of cancer.

In another aspect of the present invention, the present invention provides a method for preventing or treating cancer, which comprises a step of administering a pharmaceutical composition or a health functional food comprising a compound represented by formula 1, an isomer thereof, a solvate thereof or a pharmaceutically acceptable salt thereof as an active ingredient to a subject in need.

In another aspect of the present invention, the present invention provides a use of the pharmaceutical composition or the health functional food above comprising a compound represented by formula 1, an isomer thereof, a solvate thereof or a pharmaceutically acceptable salt thereof as an active ingredient for the prevention or treatment of cancer.

Advantageous Effect

The isoindolin-1-one derivative of the present invention exhibits a high inhibitory effect on EGFR mutations, and thus can be beneficially used for the treatment of EGFR-mutated cancers, and the isoindolin-1-one derivative exhibits a significant synergistic effect when co-administered, and thus can be beneficially used in concomitant therapy.

BRIEF DESCRIPTION OF THE DRAWINGS

FIG. 1a is a graph showing the evaluation results of the cell viability inhibitory effect of the allosteric inhibitors of Example 9 on EGFR wild-type and mutants, more particularly showing the survival rate of B a/F3 cells when only the compound according to the present invention was treated as a tyrosine kinase inhibitor (TKI).

FIG. 1b is a graph showing the evaluation results of the cell viability inhibitory effect of the allosteric inhibitor of Example 9 on EGFR wild-type and mutants, more particularly showing the survival rate of B a/F3 cells when Cetuximab (Cet.) was treated in combination with the compound of the present invention (TKI in the graph).

FIG. 2a is a graph showing the evaluation results of the cell viability inhibitory effect of the allosteric inhibitor of Example 13 on EGFR wild-type and mutants, more particularly showing the survival rate of B a/F3 cells when only the compound according to the present invention was treated as a tyrosine kinase inhibitor (TKI).

FIG. 2b is a graph showing the evaluation results of the cell viability inhibitory effect of the allosteric inhibitor of Example 13 on EGFR wild-type and mutants, more particularly showing the survival rate of B a/F3 cells when Cetuximab (Cet.) was treated in combination with the compound of the present invention (TKI in the graph).

FIG. 3a is a graph showing the evaluation results of the cell viability inhibitory effect of the allosteric inhibitor of Example 32 on EGFR wild-type and mutants, more particularly showing the survival rate of B a/F3 cells when only the compound according to the present invention was treated as a tyrosine kinase inhibitor (TKI).

FIG. 3b is a graph showing the evaluation results of the cell viability inhibitory effect of the allosteric inhibitor of Example 32 on EGFR wild-type and mutants, more particularly showing the survival rate of B a/F3 cells when Cetuximab (Cet.) was treated in combination with the compound of the present invention (TKI in the graph).

FIG. 4a is a graph showing the evaluation results of the cell viability inhibitory effect of the allosteric inhibitor of Example 33 on EGFR wild-type and mutants, more particularly showing the survival rate of B a/F3 cells when only the compound according to the present invention was treated as a tyrosine kinase inhibitor (TKI).

FIG. 4b is a graph showing the evaluation results of the cell viability inhibitory effect of the allosteric inhibitor of Example 33 on EGFR wild-type and mutants, more particularly showing the survival rate of B a/F3 cells when Cetuximab (Cet.) was treated in combination with the compound of the present invention (TKI in the graph).

FIG. 5a is a graph showing the evaluation results of allosteric inhibitory effect of EAI045 on EGFR wild type and mutants, more particularly showing the results when EAI045 was treated alone.

FIG. 5b is a graph showing the evaluation results of allosteric inhibitory effect of EAI045 on EGFR wild type and mutants, more particularly showing the results when EAI045 and Cetuximab were co-treated.

FIG. 6a is a graph showing the survival rate of B a/F3 cells when 30 nM of the compounds of Examples 9, 13, 32 and 33 and EAI045 (EAI in the graph) were treated to EGFR L858R/T790M mutant.

FIG. 6b is a graph showing the survival rate of B a/F3 cells when 100 nM of the compounds of Examples 9, 13, 32 and 33 and EAI045 (EAI in the graph) were treated to EGFR L858R/T790M mutant.

FIG. 7a is a graph showing the survival rate of B a/F3 cells when 30 nM of the compounds of Examples 9, 13, 32 and 33 and EAI045 (EAI in the graph) were treated to EGFR L858R/T790M/C797S mutant.

FIG. 7b is a graph showing the survival rate of B a/F3 cells when 100 nM of the compounds of Examples 9, 13, 32 and 33 and EAI045 (EAI in the graph) were treated to EGFR L858R/T790M/C797S mutant.

DESCRIPTION OF THE PREFERRED EMBODIMENTS

Hereinafter, the present invention is described in detail.

In one aspect of the present invention, the present invention provides a compound represented by formula 1, an isomer thereof, a solvate thereof, a hydrate thereof or a pharmaceutically acceptable salt thereof.

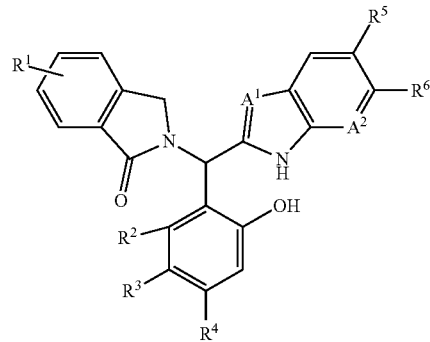

[Formula 1]

(In formula 1,
$A^1$ is CH or N;
$A^2$ is CH or N;
$R^1$ is hydrogen, $C_{3-10}$ cycloalkyl, $C_{6-10}$ aryl, 3-10 membered heterocycloalkyl containing one or more heteroatoms selected from the group consisting of N, O and S, or 5-10 membered heteroaryl containing one or more heteroatoms selected from the group consisting of N, O and S, wherein the cycloalkyl and heterocycloalkyl may be unsaturated by including one double bond,
cycloalkyl, aryl, heterocycloalkyl and heteroaryl can be independently substituted with one or more substituents selected from the group consisting of —$NR^aR^b$; straight or branched $C_{1-6}$ alkyl; acetyl; straight or branched $C_{1-6}$ alkylcarbonyl; straight or branched $C_{1-6}$ alkylaminocarbonyl; straight or branched $C_{1-6}$ alkylcarbonylamino; straight or branched $C_{1-6}$ alkylsulfonyl; saturated or unsaturated $C_{3-7}$ cycloalkyl including one double bond, which is nonsubstituted or substituted with one or more substituents selected from the group consisting of —$NR^cR^d$, acetyl, straight or branched $C_{1-6}$ alkyl, straight or branched $C_{1-6}$ alkylcarbonyl, straight or branched $C_{1-6}$ alkylaminocarbonyl, straight or branched $C_{1-6}$ alkylcarbonylamino straight or branched $C_{1-6}$ alkylsulfonyl, and 5 or 6 membered heterocycloalkyl nonsubstituted or substituted with one or more straight or branched $C_{1-4}$ alkyl containing one or more heteroatoms selected from the group consisting of N, O and S; saturated or unsaturated 3-7 membered heterocycloalkyl including one double bond and one or more heteroatoms selected from the group consisting of N, O and S, which is nonsubstituted or substituted with one or more substituents selected from the group consisting of —NR$^e$R$^f$, acetyl, straight or branched C$_{1-6}$ alkyl, straight or branched C$_{1-6}$ alkylcarbonyl, straight or branched C$_{1-6}$ alkylaminocarbonyl, straight or branched C$_{1-6}$ alkylcarbonylamino, straight or branched C$_{1-6}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S, wherein R$^a$, R$^b$, R$^c$, R$^d$, R$^e$ and R$^f$ are independently hydrogen, straight or branched C$_{1-6}$ alkyl or straight or branched C$_{1-6}$ alkylsulfonyl;

R$^2$, R$^3$ and R$^4$ are independently hydrogen, halogen or straight or branched C$_{1-6}$ alkyl, wherein the alkyl can be substituted with one or more halogens; and R$^5$ and R$^6$ are independently hydrogen, halogen or straight or branched C$_{1-6}$ alkyl, wherein the alkyl can be substituted with one or more halogens).

In formula 1 above,

R$^1$ is hydrogen, C$_{3-7}$ cycloalkyl, phenyl, 3-7 membered heterocycloalkyl containing one or more heteroatoms selected from the group consisting of N, O and S, or 5-8 membered heteroaryl containing one or more heteroatoms selected from the group consisting of N, O and S, wherein the cycloalkyl and heterocycloalkyl may be unsaturated by including one double bond, cycloalkyl, phenyl, heterocycloalkyl and heteroaryl can be independently substituted with one or more substituents selected from the group consisting of —NR$^a$R$^b$; straight or branched C$_{1-4}$ alkyl; acetyl; straight or branched C$_{1-4}$ alkylcarbonyl; straight or branched C$_{1-4}$ alkylaminocarbonyl; straight or branched C$_{1-4}$ alkylcarbonylamino; straight or branched C$_{1-4}$ alkylsulfonyl; saturated or unsaturated C$_{3-6}$ cycloalkyl including one double bond, which is nonsubstituted or substituted with one or more substituents selected from the group consisting of —NR$^c$R$^d$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; saturated or unsaturated 5 or 6 membered heterocycloalkyl including one double bond and one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S, wherein R$^a$, R$^b$, R$^c$, R$^d$, R$^e$ and R$^f$ are independently hydrogen, straight or branched C$_{1-4}$ alkyl or straight or branched C$_{1-4}$ alkylsulfonyl.

In addition, R$^1$ is hydrogen, C$_{5-6}$ cycloalkyl, phenyl, 5 or 6 membered heterocycloalkyl containing one or more heteroatoms selected from the group consisting of N, O and S, or 5 or 6 membered heteroaryl containing one or more heteroatoms selected from the group consisting of N, O and S, wherein the cycloalkyl and heterocycloalkyl may be unsaturated by including one double bond, cycloalkyl, phenyl, heterocycloalkyl and heteroaryl can be independently substituted with one or more substituents selected from the group consisting of —NR$^a$R$^b$; straight or branched C$_{1-4}$ alkyl; acetyl; straight or branched C$_{1-4}$ alkylcarbonyl; straight or branched C$_{1-4}$ alkylaminocarbonyl; straight or branched C$_{1-4}$ alkylcarbonylamino; straight or branched C$_{1-4}$ alkylsulfonyl; saturated or unsaturated C$_{5-6}$ cycloalkyl nonsubstituted or substituted with one or more substituents selected from the group consisting of —NR$^c$R$^d$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; saturated or unsaturated 5 or 6 membered heterocycloalkyl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S,
wherein R$^a$, R$^b$, R$^c$, R$^d$, R$^e$ and R$^f$ are independently hydrogen, straight or branched C$_{1-4}$ alkyl or straight or branched C$_{1-4}$ alkylsulfonyl.

In addition, R$^1$ is hydrogen, cyclohexyl, phenyl, tetrahydrofuranyl, morpholinyl, piperidinyl, piperazinyl, pyridinyl, pyrimidinyl, thiophenyl, quinolinyl, isoquinolinyl or quinazolinyl, wherein the cyclohexyl, tetrahydrofuranyl, morpholinyl, piperidinyl and piperazinyl may be unsaturated by including one double bond, cyclohexyl, phenyl, tetrahydrofuranyl, morpholinyl, piperidinyl, piperazinyl, pyridinyl, pyrimidinyl, thiophenyl, quinolinyl, isoquinolinyl and quinazolinyl can be independently substituted with one or more substituents selected from the group consisting of —NR$^a$R$^b$; straight or branched C$_{1-4}$ alkyl; acetyl; straight or branched C$_{1-4}$ alkylcarbonyl; straight or branched C$_{1-4}$ alkylaminocarbonyl; straight or branched C$_{1-4}$ alkylcarbonylamino; straight or branched C$_{1-4}$ alkylsulfonyl; saturated or unsaturated cyclohexyl including one double bond, which is nonsubstituted or substituted with one or more substituents selected from the group consisting of —NR$^c$R$^d$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino and straight or branched C$_{1-4}$ alkylsulfonyl; saturated or unsaturated 5 or 6 membered heterocycloalkyl containing one double bond and one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and saturated or unsaturated 5 or 6 membered heterocycloalkyl containing one double bond, which is nonsubstituted or substituted with one or more substituents selected from the group consisting of piperidinyl nonsubstituted or substituted with one or more straight or branched C$_{1-4}$ alkyl and piperazinyl nonsubstituted or substituted with one or more straight or branched C$_{1-4}$ alkyl; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, piperidinyl nonsubstituted or substituted with one or more straight or branched C$_{1-4}$ alkyl, and piperazinyl nonsubstituted or substituted with one or more straight or branched C$_{1-4}$ alkyl,
wherein R$^a$, R$^b$, R$^c$, R$^d$, R$^e$ and R$^f$ are independently hydrogen, straight or branched C$_{1-4}$ alkyl or straight or branched C$_{1-4}$ alkylsulfonyl.

In addition, R$^1$ is hydrogen, phenyl, piperidinyl or piperazinyl, wherein the piperidinyl may be unsaturated by including one double bond, phenyl, piperidinyl and piperazinyl can be independently substituted with one or more substituents selected from the group consisting of —NR$^a$R$^b$; straight or branched C$_{1-4}$ alkyl; and pyridinyl, pyrrolyl, piperidinyl, piperazinyl or morpholinyl nonsubstituted or substituted with one or more substituents selected from the group consisting of —NR$^e$R$^f$; acetyl; straight or branched C$_{1-4}$alkyl; piperidinyl nonsubstituted or substituted with one or more straight or branched C$_{1-4}$ alkyl; and piperazinyl nonsubstituted or substituted with one or more straight or branched C$_{1-4}$ alkyl, In addition, R$^1$ is hydrogen,

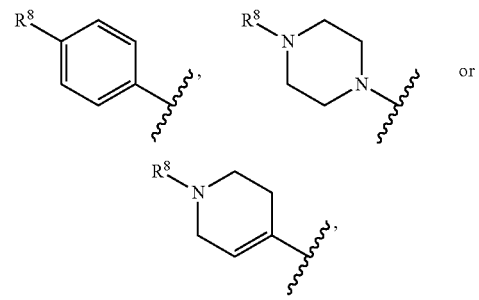

R$^8$ is independently hydrogen, —NH$_2$, straight or branched C$_{1-4}$ alkyl, pyridinyl, pyrrolyl, piperidinyl, piperazinyl or morpholinyl, wherein the pyridinyl, pyrrolyl, piperidinyl, piperazinyl and morpholinyl can be independently substituted with one or more substituents selected from the group consisting of —NR$^e$R$^f$; acetyl; straight or branched C$_{1-4}$ alkyl; piperidinyl nonsubstituted or substituted with one or more C$_{1-2}$ alkyl; and piperazinyl nonsubstituted or substituted with one or more C$_{1-2}$ alkyl, wherein R$^e$ and R$^f$ are independently hydrogen or straight or branched C$_{1-4}$ alkyl.

In addition, R$^1$ is hydrogen,

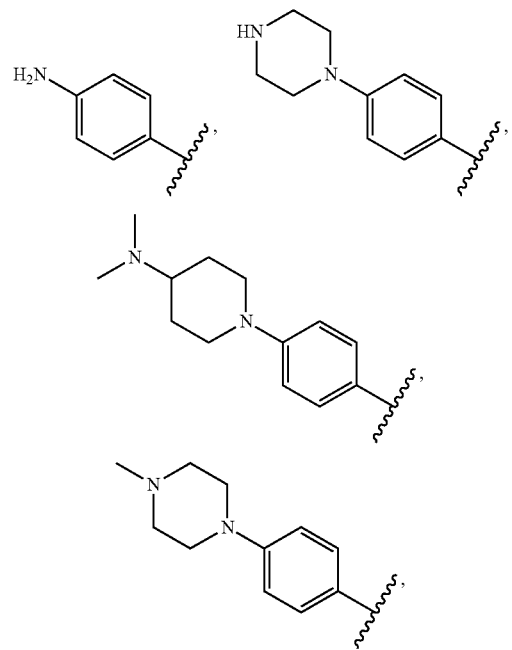

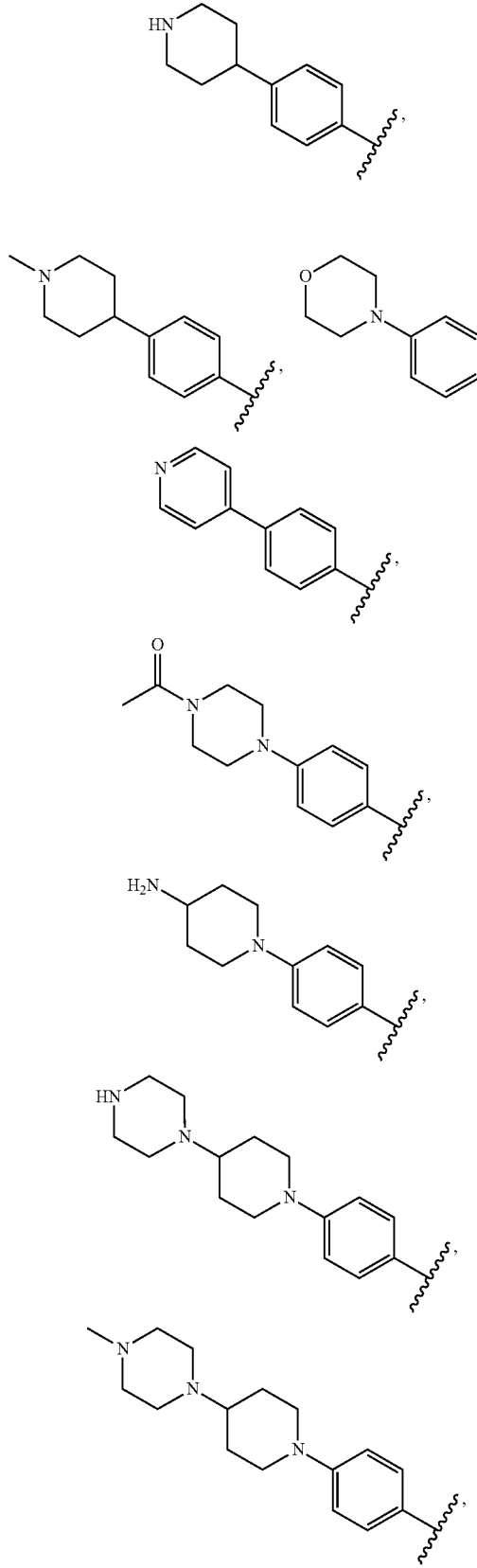
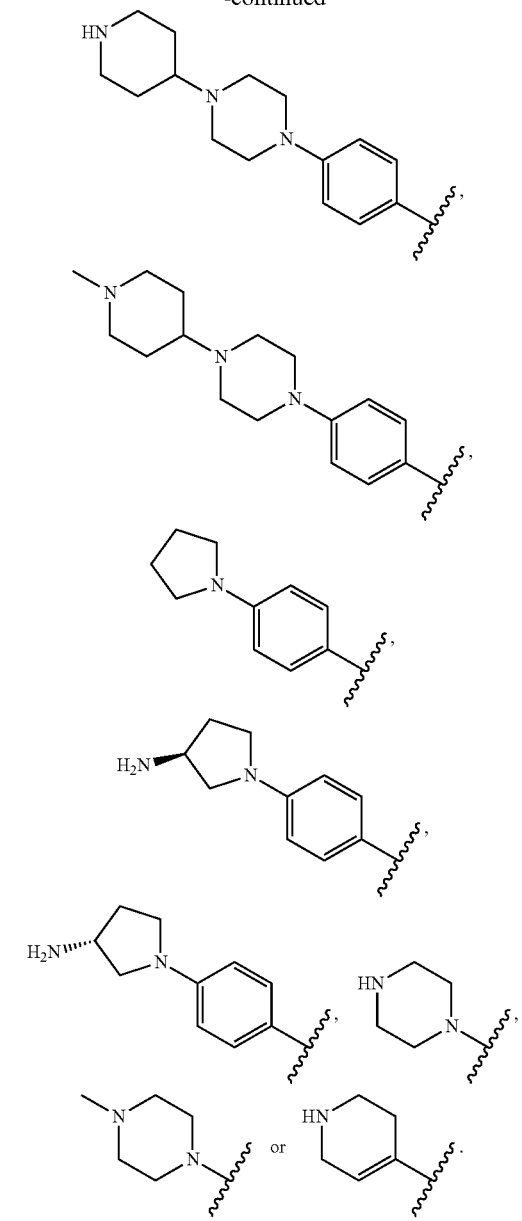

In formula 1 above,
$R^2$, $R^3$ and $R^4$ are independently hydrogen, halogen or straight or branched $C_{1-4}$ alkyl, wherein the alkyl can be substituted with one or more halogens; and
$R^5$ and $R^6$ are independently hydrogen, halogen or straight or branched $C_{1-4}$ alkyl, wherein the alkyl can be substituted with one or more halogens.

In addition, $R^2$, $R^3$ and $R^4$ are independently hydrogen, halogen or $C_{1-2}$ alkyl, wherein the alkyl can be substituted with one or more halogens; and
$R^5$ and $R^6$ are independently hydrogen, halogen or $C_{1-2}$ alkyl, wherein the alkyl can be substituted with one or more halogens.

In addition, $R^2$, $R^3$ and $R^4$ are independently hydrogen, F, Cl, $CH_3$ or $CF_3$; and
$R^5$ and $R^6$ are independently hydrogen, F or Cl.

Examples of the compound represented by formula 1 according to the present invention include the following compounds:

<1> 2-((1H-benzo[d]imidazole-2-yl)(2-hydroxyphenyl)methyl)isoindolin-1-one;
<2> 2-((6-fluoro-1H-benzo[d]imidazole-2-yl)(2-hydroxyphenyl)methyl)isoindolin-1-one;
<3> 2-((2-hydroxyphenyl)(3H-imidazo[4,5-b]pyridine-2-yl)methyl)isoindolin-1-one;
<4> 2-((6-chloro-1H-benzo[d]imidazole-2-yl)(2-hydroxyphenyl)methyl)isoindolin-1-one;
<5> 2-((5,6-dichloro-1H-benzo[d]imidazole-2-yl)(2-hydroxyphenyl)methyl)isoindolin-1-one;
<6> 2-((5-chloro-3H-imidazo[4,5-b]pyridine-2-yl)(2-hydroxyphenyl)methyl)isoindolin-1-one;
<7> 2-((1H-benzo[d]imidazole-2-yl)(5-fluoro-2-hydroxyphenyl)methyl)isoindolin-1-one;
<8> 2-((1H-benzo[d]imidazole-2-yl)(5-chloro-2-hydroxyphenyl)methyl)isoindolin-1-one;
<9> 2-((1H-benzo[d]imidazole-2-yl)(2-hydroxyphenyl)methyl)-6-(4-(piperazine-1-yl)phenyl)isoindolin-1-one;
<10> 2-((1H-benzo[d]imidazole-2-yl)(5-fluoro-2-hydroxyphenyl)methyl)-6-(4-(piperazine-1-yl)phenyl)isoindolin-1-one;
<11> 2-((1H-benzo[d]imidazole-2-yl)(5-chloro-2-hydroxyphenyl)methyl)-6-(4-(piperazine-1-yl)phenyl)isoindolin-1-one;
<12> 2-((1H-benzo[d]imidazole-2-yl)(2-hydroxyphenyl)methyl)-6-(4-aminophenyl)isoindolin-1-one;
<13> 2-((1H-benzo[d]imidazole-2-yl)(5-fluoro-2-hydroxyphenyl)methyl)-6-(4-aminophenyl)isoindolin-1-one;
<14> 2-((1H-benzo[d]imidazole-2-yl)(5-chloro-2-hydroxyphenyl)methyl)-6-(4-aminophenyl)isoindolin-1-one;
<15> 2-((1H-benzo[d]imidazole-2-yl)(2-hydroxyphenyl)methyl)-6-(1,2,3,6-tetrahydropyridine-4-yl)isoindolin-1-one;
<16> 2-((1H-benzo[d]imidazole-2-yl)(5-fluoro-2-methoxyphenyl)methyl)-6-(1,2,3,6-tetrahydropyridine-4-yl)isoindolin-1-one;
<17> 2-((1H-benzo[d]imidazole-2-yl)(5-chloro-2-methoxyphenyl)methyl)-6-(1,2,3,6-tetrahydropyridine-4-yl)isoindolin-1-one;
<18> 2-((1H-benzo[d]imidazole-2-yl)(5-fluoro-2-hydroxyphenyl)methyl)-6-(4-(4-methylpiperazine-1-yl)phenyl)isoindolin-1-one;
<19> (R)-2-((2-hydroxyphenyl)(1H-indole-2-yl)methyl)isoindolin-1-one;
<20> (R)-2-((2-hydroxy-5-methylphenyl)(1H-indole-2-yl)methyl)isoindolin-1-one;
<21> (R)-2-((2,3-difluoro-6-hydroxyphenyl)(1H-indole-2-yl)methyl)isoindolin-1-one;
<22> (R)-2-((4,5-difluoro-2-hydroxyphenyl)(1H-indole-2-yl)methyl)isoindolin-1-one;
<23> (R)-2-((5-fluoro-2-hydroxyphenyl)(1H-indole-2-yl)methyl)isoindolin-1-one;
<24> (S)-2-((5-fluoro-2-hydroxyphenyl)(1H-indole-2-yl)methyl)isoindolin-1-one;
<25> (R)-2-((2-fluoro-6-hydroxyphenyl)(1H-indole-2-yl)methyl)isoindolin-1-one;
<26> (R)-2-((5-chloro-2-hydroxyphenyl)(1H-indole-2-yl)methyl)isoindolin-1-one;
<27> (S)-2-((5-fluoro-2-hydroxyphenyl)(1H-pyrrolo[2,3-b]pyridine-2-yl)methyl)isoindolin-1-one;
<28> (R)-6-(4-aminophenyl)-2-((2-hydroxyphenyl)(1H-indole-2-yl)methyl)isoindolin-1-one;
<29> (R)-6-(4-aminophenyl)-2-((5-fluoro-2-hydroxyphenyl)(1H-indole-2-yl)methyl)isoindolin-1-one;
<30> (R)-6-(4-aminophenyl)-2-((5-chloro-2-hydroxyphenyl)(1H-indole-2-yl)methyl)isoindolin-1-one;
<31> (R)-2-((2-hydroxyphenyl)(1H-indole-2-yl)methyl)-6-(4-(piperazine-1-yl)phenyl)isoindolin-1-one;
<32> (R)-2-((5-fluoro-2-hydroxyphenyl)(1H-indole-2-yl)methyl)-6-(4-(piperazine-1-yl)phenyl)isoindolin-1-one;
<33> (R)-2-((5-chloro-2-hydroxyphenyl)(1H-indole-2-yl)methyl)-6-(4-(piperazine-1-yl)phenyl)isoindolin-1-one;
<34> (R)-2-((2-hydroxyphenyl)(1H-indole-2-yl)methyl)-6-(1,2,3,6-tetrahydropyridine-4-yl)isoindolin-1-one;
<35> (R)-2-((5-fluoro-2-hydroxyphenyl)(1H-indole-2-yl)methyl)-6-(1,2,3,6-tetrahydropyridine-4-yl)isoindolin-1-one;
<36> (R)-2-((5-chloro-2-hydroxyphenyl)(1H-indole-2-yl)methyl)-6-(1,2,3,6-tetrahydropyridine-4-yl)isoindolin-1-one;
<37> (R)-2-((5-fluoro-2-hydroxyphenyl)(1H-indole-2-yl)methyl)-6-(piperazine-1-yl)isoindolin-1-one;
<38> (R)-2-((5-fluoro-2-hydroxyphenyl)(1H-indole-2-yl)methyl)-6-(4-methylpiperazine-1-yl)isoindolin-1-one;
<39> 2-((1H-benzo[d]imidazole-2-yl)(5-fluoro-2-hydroxyphenyl)methyl)-6-(4-morpholinophenyl)isoindolin-1-one;
<40> 2-((1H-benzo[d]imidazole-2-yl)(5-chloro-2-hydroxyphenyl)methyl)-6-(4-morpholinophenyl)isoindolin-1-one;
<41> 2-((1H-benzo[d]imidazole-2-yl)(5-fluoro-2-hydroxyphenyl)methyl)-6-(4-(pyridine-4-yl)phenyl)isoindolin-1-one;
<42> 2-((1H-benzo[d]imidazole-2-yl)(5-chloro-2-hydroxyphenyl)methyl)-6-(4-(pyridine-4-yl)phenyl)isoindolin-1-one;
<43> (R)-2-((5-fluoro-2-hydroxyphenyl)(1H-indole-2-yl)methyl)-6-(4-(4-methylpiperazine-1-yl)phenyl)isoindolin-1-one;
<44> (R)-2-((5-chloro-2-hydroxyphenyl)(1H-indole-2-yl)methyl)-6-(4-(4-methylpiperazine-1-yl)phenyl)isoindolin-1-one;
<45> (R)-2-((5-fluoro-2-hydroxyphenyl)(1H-indole-2-yl)methyl)-6-(4-morpholinophenyl)isoindolin-1-one;
<46> (R)-2-((5-chloro-2-hydroxyphenyl)(1H-indole-2-yl)methyl)-6-(4-morpholinophenyl)isoindolin-1-one;
<47> (R)-2-((5-fluoro-2-hydroxyphenyl)(1H-indole-2-yl)methyl)-6-(4-(pyridine-4-yl)phenyl)isoindolin-1-one;
<48> (R)-2-((5-chloro-2-hydroxyphenyl)(1H-indole-2-yl)methyl)-6-(4-(pyridine-4-yl)phenyl)isoindolin-1-one;
<49> (R)-2-((5-fluoro-2-hydroxyphenyl)(1H-pyrrolo[2,3-b]pyridine-2-yl)methyl)-6-(4-(piperazine-4-yl)phenyl)isoindolin-1-one;
<50> (R)-2-((5-chloro-2-hydroxyphenyl)(1H-pyrrolo[2,3-b]pyridine-2-yl)methyl)-6-(4-(piperazine-4-yl)phenyl)isoindolin-1-one;
<51> (R)-2-((5-fluoro-1H-indole-2-yl)(5-fluoro-2-hydroxyphenyl)methyl)-6-(4-(piperazine-1-yl)phenyl)isoindolin-1-one;
<52> (R)-2-((5-fluoro-1H-indole-2-yl)(5-fluoro-2-hydroxyphenyl)methyl)-6-(4-(1,2,3,6-tetrahydropyridine-4-yl)phenyl)isoindolin-1-one;
<53> (S)-2-((5-fluoro-2-hydroxyphenyl)(1H-indole-2-yl)methyl)-6-(4-(piperazine-1-yl)phenyl)isoindolin-1-one;
<54> (R)-6-(4-(4-acetylpiperazine-1-yl)phenyl)-2-((5-fluoro-2-hydroxyphenyl)(1H-indole-2-yl)methyl)-isoindolin-1-one;
<55> (R)-6-(4-(4-aminopiperazine-1-yl)phenyl)-2-((5-fluoro-2-hydroxyphenyl)(1H-indole-2-yl)methyl)-isoindolin-1-one;
<56> (R)-6-(4-(4-aminopiperazine-1-yl)phenyl)-2-((5-chloro-2-hydroxyphenyl)(1H-indole-2-yl)methyl)-isoindolin-1-one;

<57> (R)-2-((5-fluoro-2-hydroxyphenyl)(1H-indole-2-yl)methyl)-6-(4-(4-(4-methylpiperazine-1-yl)piperidine-1-yl)phenyl)isoindolin-1-one;
<58> (R)-2-((5-chloro-2-hydroxyphenyl)(1H-indole-2-yl)methyl)-6-(4-(4-(4-methylpiperazine-1-yl)piperidine-1-yl)phenyl)isoindolin-1-one;
<59> (R)-2-((5-fluoro-2-hydroxyphenyl)(1H-indole-2-yl)methyl)-6-(4-(4-(piperazine-1-yl)piperidine-1-yl)phenyl)isoindolin-1-one;
<60> (R)-2-((5-chloro-2-hydroxyphenyl)(1H-indole-2-yl)methyl)-6-(4-(4-(piperazine-1-yl)piperidine-1-yl)phenyl)isoindolin-1-one;
<61> (R)-6-(4-(4-(dimethylamino)piperidine-1-yl)phenyl)-2-((5-fluoro-2-hydroxyphenyl)(1H-indole-2-yl)methyl)-isoindolin-1-one;
<62> (R)-2-((5-chloro-2-hydroxyphenyl)(1H-indole-2-yl)methyl)-6-(4-(4-(dimethylamino)piperidine-1-yl)phenyl)-isoindolin-1-one;
<63> (R)-2-((5-fluoro-2-hydroxyphenyl)(1H-indole-2-yl)methyl)-6-(4-(4-(piperidine-4-yl)piperazine-1-yl)phenyl)isoindolin-1-one;
<64> (R)-2-((5-chloro-2-hydroxyphenyl)(1H-indole-2-yl)methyl)-6-(4-(4-(piperidine-4-yl)piperazine-1-yl)phenyl)isoindolin-1-one;
<65> (R)-2-((5-fluoro-2-hydroxyphenyl)(1H-indole-2-yl)methyl)-6-(4-(4-(1-methylpiperidine-4-yl)piperazine-1-yl)phenyl)isoindolin-1-one;
<66> (R)-2-((5-chloro-2-hydroxyphenyl)(1H-indole-2-yl)methyl)-6-(4-(4-(1-methylpiperidine-4-yl)piperazine-1-yl)phenyl)isoindolin-1-one;
<67> (R)-2-((5-fluoro-2-hydroxyphenyl)(1H-indole-2-yl)methyl)-6-(4-(pyrrolidine-1-yl)phenyl)isoindolin-1-one;
<68> (R)-2-((5-chloro-2-hydroxyphenyl)(1H-indole-2-yl)methyl)-6-(4-(pyrrolidine-1-yl)phenyl)isoindolin-1-one;
<69> 6-(4-((R)-3-aminopyrrolidine-1-yl)phenyl)-2-((R)-(5-fluoro-2-hydroxyphenyl)(1H-indole-2-yl)methyl)isoindolin-1-one;
<70> 6-(4-((R)-3-aminopyrrolidine-1-yl)phenyl)-2-((R)-(5-chloro-2-hydroxyphenyl)(1H-indole-2-yl)methyl)isoindolin-1-one; and
<71> 6-(4-((S)-3-aminopyrrolidine-1-yl)phenyl)-2-((R)-(5-fluoro-2-hydroxyphenyl)(1H-indole-2-yl)methyl)isoindolin-1-one.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The term "hydrate" refers to a compound or a salt thereof of the present invention containing a stoichiometric or non-stoichiometric amount of water bound by a non-covalent intermolecular force. The hydrate of the compound represented by formula 1 of the present invention can contain a stoichiometric or non-stoichiometric amount of water bonded by a non-covalent intermolecular force. The hydrate can contain 1 equivalent or more of water, preferably 1 to 5 equivalents of water. The hydrate can be prepared by crystallizing the compound represented by formula 1, the isomer thereof, or the pharmaceutically acceptable salt thereof from water or the solvent containing water.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human.

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

In another aspect of the present invention, the present invention provides a method for preparing a compound represented by formula 1a comprising the following steps, as shown in reaction formula 1 below:
  preparing a compound represented by formula 3 by reacting a compound represented by formula 5 with a compound represented by formula 4 (step 1);

preparing a compound represented by formula 2 by cyclization of the compound represented by formula 3 (step 2); and preparing a compound represented by formula 1a by reacting the compound represented by formula 2 (step 3):

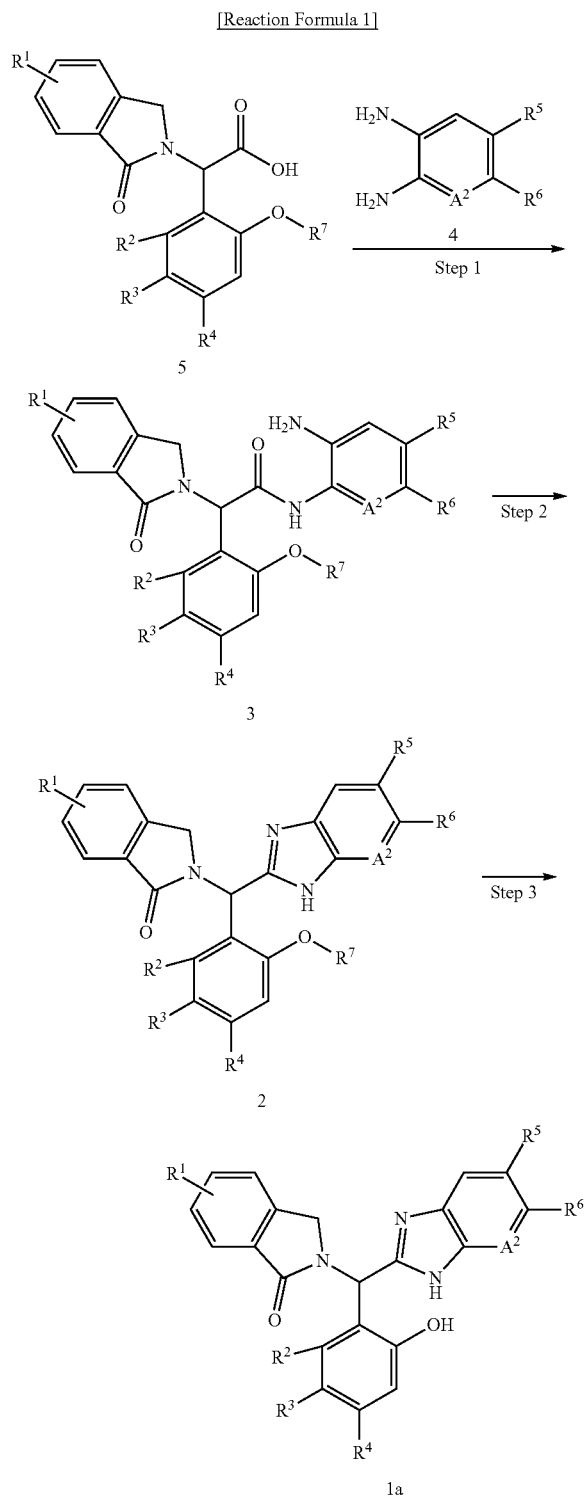

[Reaction Formula 1]

(In reaction formula 1,
$A^2$, $R^1$, $R^2$, $R^3$, $R^4$, $R^5$ and $R^6$ are as defined in formula 1;
$R^7$ is straight or branched $C_{1-6}$ alkyl; and
the compound represented by formula 1a is a derivative when $A^1$ is N in the compound represented by formula 1).

Hereinafter, the preparation method shown in the reaction formula 1 is described in more detail.

In the preparation method of the reaction formula 1, step 1 is a step of preparing a compound represented by formula 3 by reacting a compound represented by formula 5 with a compound represented by formula 4. This step can be performed using generally used conditions in which OH of the carboxyl group of the compound represented by formula 5 and the primary amine of the compound represented by formula 4 react to form an amide bond. In an embodiment of the present invention, a compound represented by formula 3 was prepared by condensation in the presence of a condensing agent and a base to form an amide bond, but not always limited thereto.

At this time, the condensing agent that can be used herein includes organophosphorus reagents such as bis(2-oxo-3-oxazolidinyl)phosphinic chloride (BOP-Cl), benzotriazol-1-yloxytris(dimethylamino)phosphonium hexafluorophosphate (BOP) and diphenylphosphonylazide (DPPA); and carbodiimide-based reagents such as dicyclohexylcarbodiimide (DCC), diisopropylcarbodiimide (DIC) and 1-ethyl-3-(3-dimethylaminopropyl)carbodiimide (EDC). Preferably, N,N-carbonyldiimidazole, 0-benzotriazole-N,N,N',N'-tetramethyl-uroninium-hexafluorophosphate (HBTU), 1-[bis(dimethylamino)methylene]-1H-1,2,3-triazolo[4,5-b]pyridinium 3-oxide hexafluorophosphate (HATU) and the like can be used herein.

In addition, the base was used to promote the reaction and increase the yield. The base that can be used herein includes organic bases such as N,N-dimethylaminopyridine (DMAP), pyridine, triethylamine, N,N-diisopropylethylamine and 1,8-diazabicyclo[5.4.0]-7-undecene (DBU), or inorganic bases such as sodium bicarbonate, sodium hydroxide and potassium hydroxide, and these can be used in an equivalent amount or excess amount, alone or in combination.

Further, as the reaction solvent, an ether solvent such as tetrahydrofuran, dioxane, dichloromethane and 1,2-dimethoxyethane; an aromatic hydrocarbon solvent such as benzene, toluene and xylene; N,N-dimethylformamide (DMF); dimethyl sulfoxide; acetonitrile; and the like can be used alone or in combination.

In the preparation method of the reaction formula 1, step 2 is a step of preparing a compound represented by formula 2 by cyclization of the compound represented by formula 3. Step 2 can be performed using generally used conditions capable of forming imidazole through cyclization. In an embodiment of the present invention, after performing the step 1, an imidazole compound represented by formula 2 was prepared by trituration with methylene chloride and n-hexane using a compound represented by formula 3 in a crude state, but not always limited thereto.

In the preparation method of the reaction formula 1, step 3 is a step of preparing a compound represented by formula 1a by reacting the compound represented by formula 2. Specifically, this step is a step of forming OH by O-dealkylation of the compound represented by formula 2. This step can be performed using generally used conditions capable of O-dealkylation. In an embodiment of the present invention, alkyl was removed by using boron tribromide, but not always limited thereto.

In another aspect of the present invention, the present invention provides a method for preparing a compound represented by formula 1b comprising the following steps, as shown in reaction formula 2 below:
preparing a compound represented by formula 6 by reacting a compound represented by formula 8 with a compound represented by formula 7 (step 1); and
preparing a compound represented by formula 1b by reacting the compound represented by formula 6 (step 2):

[Reaction Formula 2]

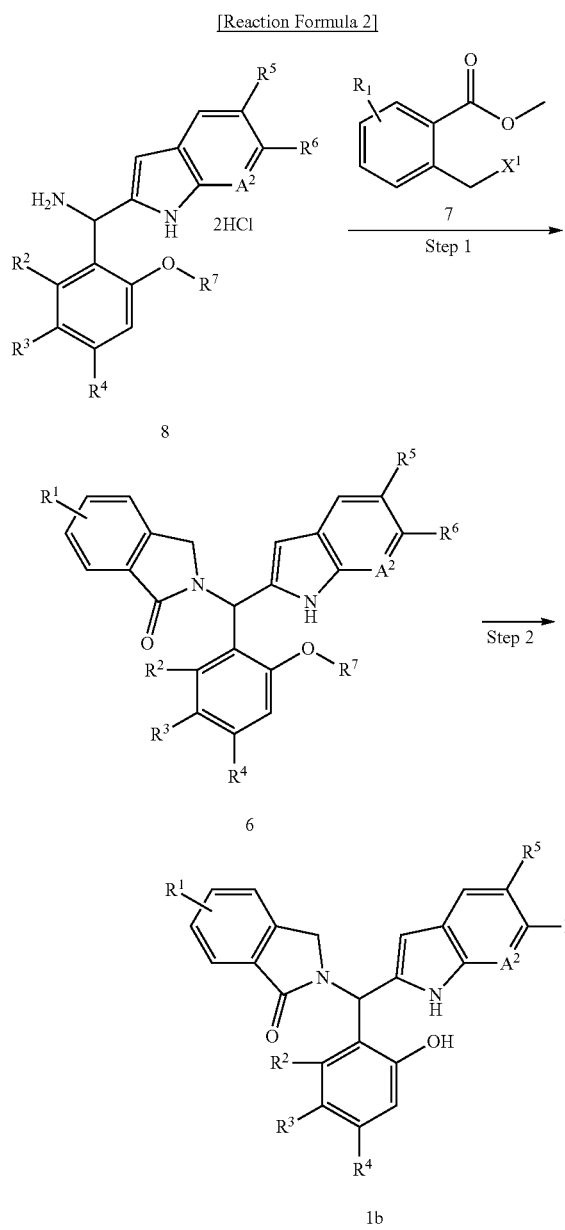

(In reaction formula 2,
$A^2$, $R^1$, $R^2$, $R^3$, $R^4$, $R^5$ and $R^6$ are as defined in formula 1;
$R^7$ is straight or branched $C_{1-6}$ alkyl;
$X^1$ is halogen; and
the compound represented by formula 1b is a derivative when $A^1$ is CH in the compound represented by formula 1).

In the preparation method of the reaction formula 2, step 1 is a step of preparing a compound represented by formula 6 by reacting a compound represented by formula 8 with a compound represented by formula 7. This step is a step of forming isoindolin-1-one represented by formula 6 by cyclization of the compound represented by formula 8 and the compound represented by formula 7. Step 1 can be performed using generally used conditions capable of forming indole through cyclization. In an embodiment of the present invention, the compound represented by formula 6 was prepared by refluxing the compound represented by formula 8 and the compound represented by formula 7 in the presence of a base, but not always limited thereto.

At this time, the base that can be used herein includes organic bases such as N,N-dimethylaminopyridine (DMAP), pyridine, triethylamine, N,N-diisopropylethylamine and 1,8-diazabicyclo[5.4.0]-7-undecene (DBU), or inorganic bases such as sodium bicarbonate, sodium hydroxide and potassium hydroxide, and these can be used in an equivalent amount or excess amount, alone or in combination.

Further, as the reaction solvent, an ether solvent such as tetrahydrofuran, dioxane, dichloromethane and 1,2-dimethoxyethane; an aromatic hydrocarbon solvent such as benzene, toluene and xylene; N,N-dimethylformamide (DMF); dimethyl sulfoxide; acetonitrile; and the like can be used alone or in combination.

In the preparation method of the reaction formula 2, step 2 is a step of preparing a compound represented by formula 1b by reacting the compound represented by formula 6. Specifically, this step is a step of forming OH by O-dealkylation of the compound represented by formula 6. This step can be performed using generally used conditions capable of O-dealkylation. In an embodiment of the present invention, alkyl was removed by using boron tribromide, but not always limited thereto.

In another aspect of the present invention, the present invention provides a pharmaceutical composition comprising a compound represented by formula 1, an isomer thereof, a solvate thereof, a hydrate thereof or a pharmaceutically acceptable salt thereof as an active ingredient for the prevention or treatment of cancer.

The cancer can be at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lip cancer, mycelia, acute myelogenous leukemia, acute lymphocytic leukemia, basal cell cancer, ovarian epithelial carcinoma, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer and thymus cancer, in which a mutation is expressed in EGFR.

In addition, the compound can inhibit EGFR (epidermal growth factor receptor) mutations. At this time, the EGFR mutation is at least one selected from the group consisting of EGFR del19, EGFR del19/T790M, EGFR del19/T790M/C797S, EGFR L858R, EGFR L858R/T790M and EGFR L858R/T790M/C797S.

Further, the compound may act as an allosteric inhibitor to EGFR (epidermal growth factor receptor).

In addition, the pharmaceutical composition can be administered as an individual therapeutic agent or can be used in combination with other anticancer agents in use.

Further, the pharmaceutical composition can be administered in combination with an anticancer agent to enhance the anticancer effect.

The compound represented by formula 1 of the present invention exhibited high inhibitory activity against EGFR L858R/T790M/C797S, a triple mutation of EGFR (see Experimental Example 1). The compound of the present invention exhibited selective inhibitory effect on EGFR mutants than wild type, and particularly, among the mutants, showed remarkably superior inhibitory effect on EGFR L858R/T790M and EGFR L858R/T790M/C797S. When the compound of the present invention was co-administered with a conventional anticancer agent, the cell viability of Ba/F3 cells expressing EGFR L858R/T790M and EGFR L858R/T790M/C797S was significantly decreased. The compound of the present invention significantly reduced the cell viability of Ba/F3 cells expressing EGFR L858R/T790M and EGFR L858R/T790M/C797S compared to EAI045, a well known allosteric inhibitor to EGFR L858R/T790M, and exhibited more excellent effect than the conventional inhibitor (Experimental Example 2).

Accordingly, the compound represented by formula 1 according to the present invention exhibited higher inhibitory ability against EGFR mutations than EGFR wild type, and particularly, showed remarkably excellent inhibitory effect on EGFR L858R/T790M/C797S. Among the various EGFR mutations, the compound of the present invention selectively showed excellent inhibitory effect on EGFR L858R/T790M and EGFR L858R/T790M/C797S, so that the compound of the present invention can be effectively used in the treatment of cancer expressing EGFR L858R/T790M or EGFR L858R/T790M/C797S.

In addition, the compound of the present invention exhibited a significant synergistic effect when co-administered, and thus can be beneficially used in concomitant therapy.

The compound represented by formula 1 of the present invention or the pharmaceutically acceptable salt thereof can be administered orally or parenterally and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a health functional food comprising a compound represented by formula 1, an isomer thereof, a solvate thereof, a hydrate thereof or a pharmaceutically acceptable salt thereof as an active ingredient for the prevention or amelioration of cancer.

The cancer can be at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lip cancer, mycelia, acute myelogenous leukemia, acute lymphocytic leukemia, basal cell cancer, ovarian epithelial carcinoma, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer and thymus cancer, in which a mutation is expressed in EGFR.

The compound represented by formula 1 according to the present invention exhibits high inhibitory activity against EGFR mutations, and thus can be added to health functional foods such as foods and beverages as a health functional food composition for preventing or ameliorating cancer.

The compound represented by formula 1 of the present invention can be used as a food additive. In that case, the compound represented by formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~ 90 weight part for the total weight of the food. However, if long term administration is required for health and hygiene or regulating health condition, the content can be lower than the above but higher content can be accepted as well since the compound of the present invention has been proved to be very safe.

In addition, the health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~ 20 g and more preferably 5~ 12 g in 100 g of the composition of the invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

In another aspect of the present invention, the present invention provides a method for preventing or treating cancer, which comprises a step of administering a pharmaceutical composition or a health functional food comprising a compound represented by formula 1, an isomer thereof, a solvate thereof or a pharmaceutically acceptable salt thereof as an active ingredient to a subject in need.

In another aspect of the present invention, the present invention provides a use of the pharmaceutical composition or the health functional food above comprising a compound represented by formula 1, an isomer thereof, a solvate thereof or a pharmaceutically acceptable salt thereof as an active ingredient for the prevention or treatment of cancer.

Hereinafter, the present invention will be described in detail by the following examples and experimental examples.

However, the following examples and experimental examples are only for illustrating the present invention, and the contents of the present invention are not limited thereto.

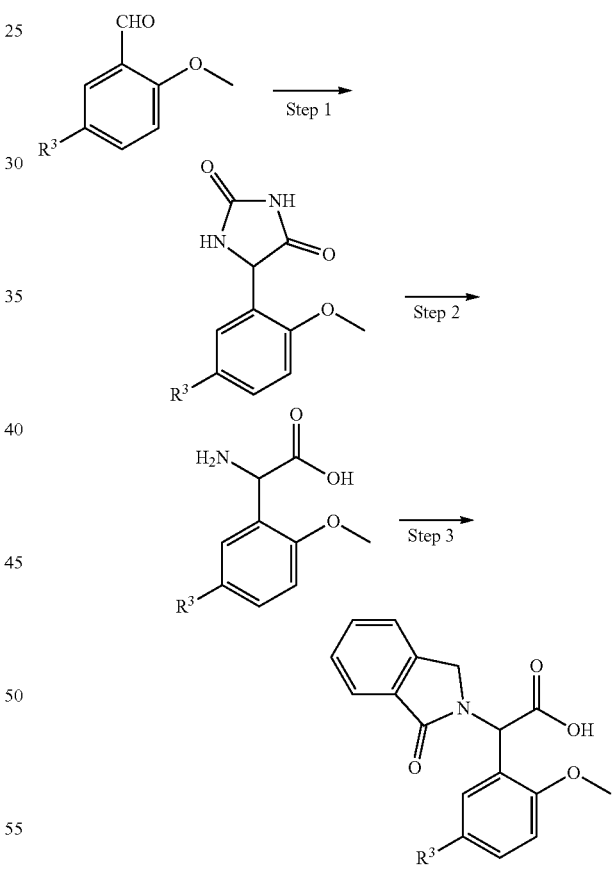

1: R³ = H
2: R³ = F
3: R³ = Cl

According to reaction formula a, the compounds of Preparative Examples 1 to 3 were obtained. In reaction formula a, 1 is the compound of Preparative Example 1, 2 is the compound of Preparative Example 2, and 3 is the compound of Preparative Example 3.

<Preparative Example 1> Preparation of 2-(2-methoxyphenyl)-2-(1-oxoisoindole-2-yl)acetic acid

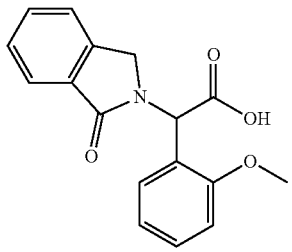 [SMILES: COc1ccccc1C(C(=O)O)N1Cc2ccccc2C1=O]

Step 1: Preparation of 5-(2-methoxyphenyl)imidazolidine-2,4-dione

Water solution (250 ml) of potassium cyanide (30 g, 461 mmol) was added dropwise to a mixture of water (160 ml) and ethanol (400 ml) of 2-methoxybenzaldehyde (50 g, 367 mmol) and ammonium carbonate (95 g, 990 mmol) at 50° C. for 30 minutes. The reaction mixture was heated to 60° C., followed by stirring for 5 hours. Ethanol was removed under reduced pressure and the residue was cooled to 20° C. The reaction mixture was acidified to pH 1 with 35% hydrochloric acid aqueous solution at 0° C. to induce precipitation of the product. The resulting solid was filtered and washed with cold water to give 5-(2-methoxyphenyl)imidazolidine-2,4-dione (55 g, pale yellow powder, yield: 72%), which was used in the next step without further purification.

$^1$H NMR (300 MHz, chloroform-d) δ 7.39 (td, J=8.0, 1.7 Hz, 1H), 7.27 (d, J=1.8 Hz, 1H), 7.01 (d, J=7.4 Hz, 1H), 6.96 (d, J=8.4 Hz, 1H), 5.64 (br s, 1H), 5.32 (s, 1H), 3.87 (s, 3H).

Step 2: Preparation of 2-amino-2-(2-methoxyphenyl)acetic acid 5-(2-Methoxyphenyl)imidazolidine-2,4-dione (50 g, 242 mmol) was added to water solution (200 mL) of potassium hydroxide (56 g, 1 mol), and the mixture was refluxed for 60 hours. The reaction mixture was cooled to 0° C., to which 35% hydrochloric acid aqueous solution was added dropwise until the pH reached 7. The reaction mixture was filtered and washed with cold water to give 2-amino-2-(2-methoxyphenyl)acetic acid (34 g, white powder, yield: 55%), which was used in the next step without further purification.

$^1$H NMR (300 MHz, Deuterium Oxide) δ 7.43-7.35 (m, 1H), 7.26 (dd, J=7.5, 1.7 Hz, 1H), 7.01 (d, J=8.4 Hz, 1H), 6.96 (td, J=7.7, 1.3 Hz, 1H), 4.74 (s, 1H), 3.77 (s, 3H).

Step 3: Preparation of 2-(2-methoxyphenyl)-2-(1-oxoisoindole-2-yl)acetic acid Phthalaldehyde (8.1 g, 61 mmol) was added to the acetic acid (275 mL) reaction mixture of 2-amino-2-(2-methoxyphenyl)acetic acid (10 g, 55 mmol). The reaction mixture was stirred at 110° C. for 10 minutes. After cooling the reaction mixture to room temperature, the mixture was concentrated under reduced pressure to remove acetic acid. The residue was fractionated as ethyl acetate and saturated sodium bicarbonate solution. The combined aqueous layer was acidified to pH 2 with 1 N hydrochloric acid aqueous solution, followed by extraction three times with ethyl acetate. The combined organic layer was washed with brine, dried over MgSO$_4$ and filtered. The organic filtrate was evaporated under reduced pressure to give 2-(2-methoxyphenyl)-2-(1-oxoisoindole-2-yl)acetic acid (8 g, white solid, yield: 50%).

$^1$H NMR (500 MHz, DMSO-d$_6$) δ 13.14 (br s, 1H), 7.72 (d, J=7.5 Hz, 1H), 7.59 (td, J=7.3, 1.2 Hz, 1H), 7.55 (d, J=7.5 Hz, 1H), 7.50 (td, J=7.4, 1.2 Hz, 1H), 7.41 (td, J=7.8, 1.7 Hz, 1H), 7.30 (dd, J=7.6, 1.7 Hz, 1H), 7.12 (dd, J=8.4, 1.1 Hz, 1H), 7.03 (td, J=7.5, 1.1 Hz, 1H), 6.13 (s, 1H), 4.61 (d, J=17.5 Hz, 1H), 3.88 (d, J=17.5 Hz, 1H).

<Preparative Example 2> Preparation of 2-(5-fluoro-2-methoxyphenyl)-2-(1-oxoisoindole-2-yl)acetic acid

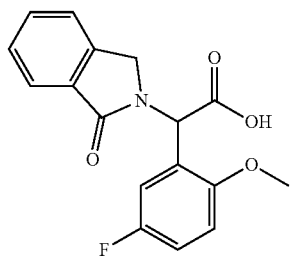 [SMILES: COc1ccc(F)cc1C(C(=O)O)N1Cc2ccccc2C1=O]

Step 1: Preparation of 5-(5-fluoro-2-methoxyphenyl)imidazolidine-2,4-dione 5-(5-Fluoro-2-methoxyphenyl)imidazolidine-2,4-dione was obtained by performing the same method as in step 1 of Preparative Example 1.

$^1$H NMR (300 MHz, DMSO-d$_6$) δ 10.2 (br s, 1H), 8.09 (s, 1H), 7.24-7.05 (m, 3H), 5.21 (d, J=1.0 Hz, 1H), 3.75 (s, 3H); Mass (ESI), calcd for C$_{10}$H$_9$FN$_2$O$_3$ 224.06, found m/z 225.0 (M+H$^+$).

Step 2: Preparation of 2-amino-2-(5-fluoro-2-methoxyphenyl)acetic acid

2-Amino-2-(5-fluoro-2-methoxyphenyl)acetic acid (6.5 g, 55%) was obtained by performing the same method as in step 2 of Preparative Example 1.

$^1$H NMR (500 MHz, CD$_3$OD) δ 7.17 (dd, J=8.9, 3.1 Hz, 1H), 7.13 (td, J=8.5, 3.1, 1H), 7.06 (dd, J=9.0, 4.4 Hz, 1H), 4.80 (s, 1H), 3.90 (s, 3H).

Step 3: Preparation of 2-(5-fluoro-2-methoxyphenyl)-2-(1-oxoisoindole-2-yl)acetic acid 2-(5-Fluoro-2-methoxyphenyl)-2-(1-oxoisoindole-2-yl) acetic acid (7.5 g, 54%) was obtained by performing the same method as in step 3 of Preparative Example 1.

$^1$H NMR (300 MHz, DMSO-d$_6$) δ 13.2 (br s, 1H), 7.73 (dt, J=7.5, 1.0 Hz 1H), 77.64-7.48 (m, 3H), 7.26 (td, J=8.6, 3.1 Hz, 1H), 7.15 (dt, J=9.0, 3.8 Hz, 2H), 6.12 (s, 1H), 4.65 (d, J=17.5 Hz, 1H), 3.99 (d, J=17.5 Hz, 1H), 3.80 (s, 3H); Mass (ESI), calcd for C$_{17}$H$_{14}$FNO$_4$ 315.09, found m/z 316.1 (M+H$^+$).

<Preparative Example 3> Preparation of 2-(5-chloro-2-methoxyphenyl)-2-(1-oxoisoindole-2-yl) acetic acid

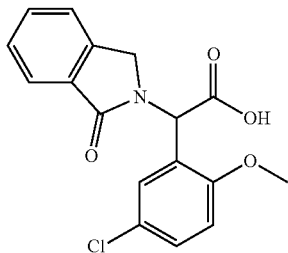 [SMILES: COc1ccc(Cl)cc1C(C(=O)O)N1Cc2ccccc2C1=O]

Step 1: Preparation of 5-(5-chloro-2-methoxyphenyl)imidazolidine-2,4-dione 5-(5-Chloro-2-methoxyphenyl)imidazolidine-2,4-dione (10 g, 71%) was obtained by performing the same method as in step 1 of Preparative Example 1.

$^1$H NMR (300 MHz, methanol-d$_4$) δ 7.38 (dd, J=8.8, 2.6 Hz, 1H), 7.29 (d, J=2.6 Hz, 1H), 7.06 (d, J=8.8 Hz, 1H), 5.25 (s, 1H), 3.85 (s, 3H).

Step 2: Preparation of 2-amino-2-(5-chloro-2-methoxyphenyl)acetic acid

2-Amino-2-(5-chloro-2-methoxyphenyl)acetic acid (7.6 g, 85%) was obtained by performing the same method as in step 2 of Preparative Example 1.

Step 3: Preparation of 2-(5-chloro-2-methoxyphenyl)-2-(1-oxoisoindole-2-yl)acetic acid 2-(5-Chloro-2-methoxyphenyl)-2-(1-oxoisoindole-2-yl) acetic acid (1.7 g 37%) was obtained by performing the same method as in step 3 of Preparative Example 1.

$^1$H NMR (300 MHz, DMSO-d$_6$) δ 13.27 (br s, 1H), 7.73 (dt, J=7.5, 1.1 Hz, 1H), 7.64-7.54 (m, 2H), 7.51 (dd, J=7.4, 1.7 Hz, 1H), 7.46 (dd, J=8.8, 2.6 Hz, 1H), 7.31 (d, J=2.7 Hz, 1H), 7.15 (d, J=8.9 Hz, 1H), 6.10 (s, 1H), 4.65 (d, J=17.5 Hz, 1H), 3.99 (d, J=17.5 Hz, 1H), 3.81 (s, 3H).

<Preparative Example 4> Preparation of methyl 5-bromo-2-(bromomethyl)benzoate

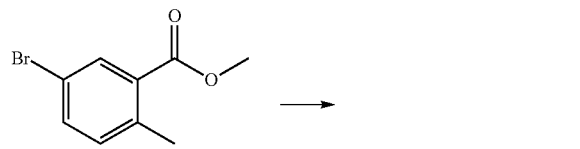

Methyl 5-bromo-2-methylbenzoate is commercially available and can also be prepared by the following method and used.

N-bromosuccinimide (2.2 g, 12 mmol) and 2-(azo(1-cyano-1-methylethyl))-2-methylpropane nitrile (36 mg, 0.22 mmol) were added to benzene solution (55 mL) of methyl 5-bromo-2-methylbenzoate (2.5 g, 11 mmol). The reaction mixture was refluxed for 30 minutes. After cooling the reaction mixture to room temperature, the mixture was concentrated and fractionated as ethyl acetate and water. The organic layer was dried over MgSO$_4$, filtered, and concentrated under reduced pressure to give methyl 5-bromo-2-(bromomethyl)benzoate (2.8 g, yellow oil and white solid, yield: 84%).

$^1$H NMR (300 MHz, chloroform-d) δ 8.10 (d, J=1.8 Hz, 1H), 7.66-7.56 (m, 1H), 7.34 (d, J=8.2 Hz, 1H), 4.90 (s, 2H), 3.95 (s, 3H).

<Preparative Example 5> Preparation of 2-(6-bromo-1-oxoisoindole-2-yl)-2-(2-methoxyphenyl) acetic acid

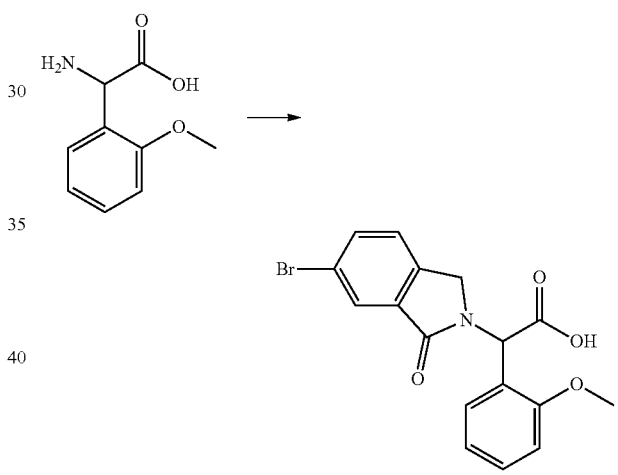

Diisopropylethylamine (7.8 mL) was added to N,N-dimethylformamide (45 mL) of 2-amino-2-(2-methoxyphenyl) acetic acid (1.6 g, 9 mmol) and crude methyl 5-bromo-2-(bromomethyl)benzoate (2.8 g, 9 mmol). The reaction mixture was stirred at 80° C. overnight and concentrated under reduced pressure. The residue was extracted with ethyl acetate and saturated sodium bicarbonate solution. The combined aqueous layer was acidified to pH 2 with 1 N hydrochloric acid aqueous solution, followed by extraction three times with ethyl acetate. The combined organic layer was washed with brine, dried over MgSO$_4$ and filtered. The organic filtrate was evaporated under reduced pressure to give 2-(6-bromo-1-oxoisoindole-2-yl)-2-(2-methoxyphenyl)acetic acid (1 g, brown solid, yield: 27%).

$^1$H NMR (300 MHz, DMSO-d$_6$) δ 13.16 (s, 1H), 7.86 (d, J=1.8 Hz, 1H), 7.79 (dd, J=8.1, 1.9 Hz, 1H), 7.53 (d, J=8.1 Hz, 1H), 7.42 (td, J=7.9, 7.4, 1.7 Hz, 1H), 7.29 (dd, J=7.6, 1.7 Hz, 1H), 7.12 (d, J=8.3 Hz, 1H), 7.07-6.99 (m, 1H), 6.11 (s, 1H), 4.58 (d, J=18.0 Hz, 1H), 3.87 (d, J=18.0 Hz, 1H), 3.80 (s, 3H).

[Reaction Formula b]

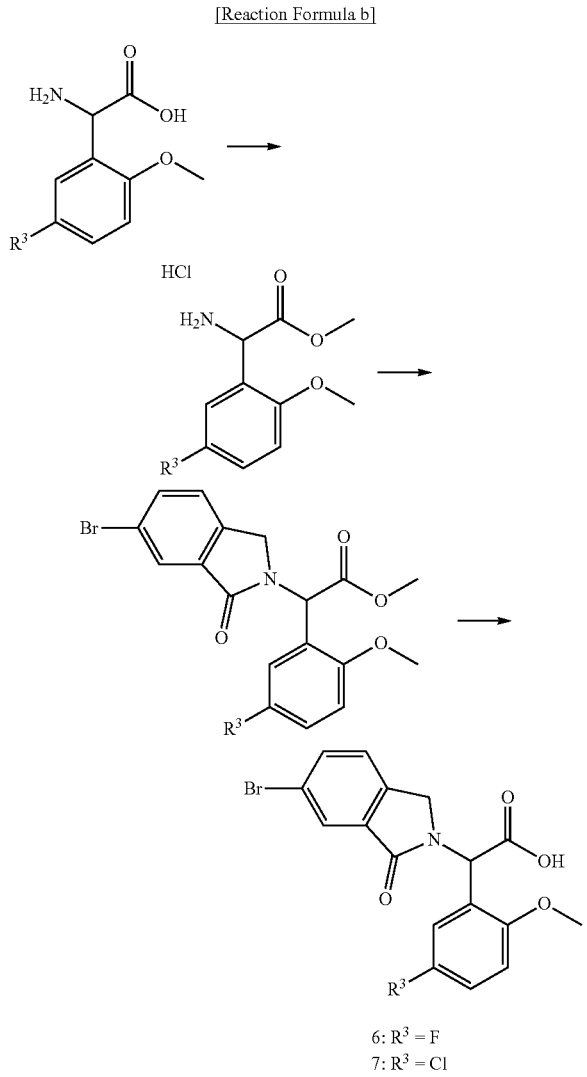

6: R³ = F
7: R³ = Cl

According to reaction formula b, the compounds of Preparative Examples 6 and 7 were obtained. In reaction formula b, 6 is the compound of Preparative Example 6, and 7 is the compound of Preparative Example 7.

<Preparative Example 6> Preparation of 2-(6-bromo-1-oxoisoindole-2-yl)-2-(5-fluoro-2-methoxyphenyl)acetic acid

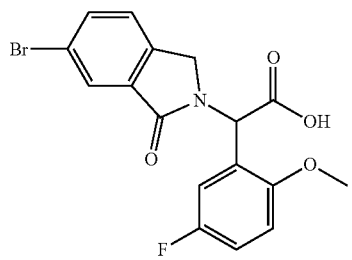 [SMILES: COc1ccc(F)cc1C(C(=O)O)N1Cc2ccc(Br)cc2C1=O]

Step 1: Preparation of methyl 2-amino-2-(5-fluoro-2-methoxyphenyl)acetate hydrochloride Thionyl chloride (7 mL) was added dropwise to methanol (125 mL) of 2-amino-2-(5-fluoro-2-methoxyphenyl)acetic acid (5 g, 25 mmol) at 0° C. The reaction mixture was refluxed for 1 hour. Upon completion of the reaction, the reaction mixture was concentrated under reduced pressure to give methyl 2-amino-2-(5-fluoro-2-methoxyphenyl)acetate hydrochloride (6 g, white salt, yield: 96%).

$^1$H NMR (300 MHz, DMSO-$d_6$) δ 8.98 (s, 3H), 7.39 (dd, J=8.9, 3.1 Hz, 1H), 7.29 (td, J=8.7, 3.2 Hz, 1H), 7.14 (dd, J=9.1, 4.5 Hz, 1H), 5.32 (s, 1H), 3.80 (s, 3H), 3.70 (s, 3H).

Step 2: Preparation of methyl 2-(6-bromo-1-oxoisoindole-2-yl)-2-(5-fluoro-2-methoxyphenyl)acetate Methyl 2-(6-bromo-1-oxoisoindole-2-yl)-2-(5-fluoro-2-methoxyphenyl)acetate was prepared according to the same method as in step 1 above, except for the extraction step. Upon completion of the reaction, the reaction mixture was concentrated under reduced pressure, and the residue was extracted several times with ethyl acetate and water. The combined organic layer was washed with brine, dried over MgSO₄, filtered, and concentrated.

LC-MS (M+H⁺) calcd for C18H15BrFNO4 407.0, found 408.0.

Step 3: Preparation of 2-(6-bromo-1-oxoisoindole-2-yl)-2-(5-fluoro-2-methoxyphenyl)acetic acid 1 N sodium hydroxide aqueous solution was added to tetrahydrofuran solution of methyl 2-(6-bromo-1-oxoisoindole-2-yl)-2-(5-fluoro-2-methoxyphenyl)acetate. After stirring for 4 hours, the reaction mixture was extracted with ethyl acetate and saturated sodium bicarbonate solution. The combined aqueous layer was acidified to pH 2 with 1 N hydrochloric acid aqueous solution, followed by extraction three times with ethyl acetate. The combined organic layer was washed with brine, dried over MgSO₄ and filtered. The organic filtrate was evaporated under reduced pressure to give 2-(6-bromo-1-oxoisoindole-2-yl)-2-(5-fluoro-2-methoxyphenyl)acetic acid.

LC-MS (M+H⁺) calcd for C17H13BrFNO4 393.00, found 394.1.

<Preparative Example 7> Preparation of 2-(6-bromo-1-oxoisoindole-2-yl)-2-(5-chloro-2-methoxyphenyl)acetic acid

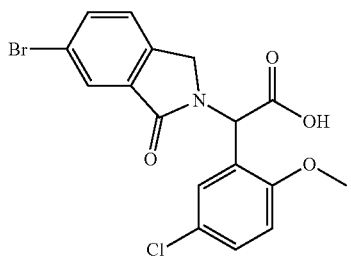 [SMILES: COc1ccc(Cl)cc1C(C(=O)O)N1Cc2ccc(Br)cc2C1=O]

Step 1: Preparation of methyl 2-amino-2-(5-chloro-2-methoxyphenyl)acetate hydrochloride Methyl 2-amino-2-(5-chloro-2-methoxyphenyl)acetate hydrochloride (2 g, 99%) was obtained by performing the same method as in step 1 of Preparative Example 6.

$^1$H NMR (300 MHz, methanol-d$_4$) δ 7.50 (dd, J=8.7, 2.7 Hz, 1H), 7.46 (d, J=2.5 Hz, 1H), 7.15 (d, J=8.8 Hz, 1H), 5.29 (s, 1H), 3.91 (s, 3H), 3.82 (s, 3H).

Step 2: Preparation of methyl 2-(6-bromo-1-oxoisoindole-2-yl)-2-(5-chloro-2-methoxyphenyl)acetate Methyl 2-(6-bromo-1-oxoisoindole-2-yl)-2-(5-chloro-2-methoxyphenyl)acetate was obtained by performing the same method as in step 2 of Preparative Example 6.

LC-MS (M+H$^+$) calcd for C18H15BrClNO4 423.0, found 423.1.

Step 3: Preparation of 2-(6-bromo-1-oxoisoindole-2-yl)-2-(5-chloro-2-methoxyphenyl)acetic acid 2-(6-Bromo-1-oxoisoindole-2-yl)-2-(5-chloro-2-methoxyphenyl)acetic acid was obtained by performing the same method as in step 3 of Preparative Example 6.

LC-MS (M+H$^+$) calcd for C17H13BrClNO4 409.0, found 410.0.

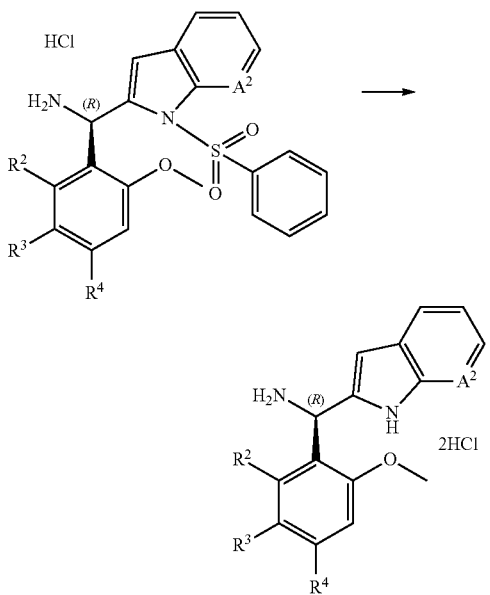

8: R$^2$ = H, R$^3$ = H, R$^4$ = H, A$^2$ = C
9: R$^2$ = H, R$^3$ = F, R$^4$ = H, A$^2$ = C
10: R$^2$ = H, R$^3$ = Cl, R$^4$ = H, A$^2$ = C
11: R$^2$ = H, R$^3$ = CH$_3$, R$^4$ = H, A$^2$ = C
12: R$^2$ = F, R$^3$ = F, R$^4$ = H, A$^2$ = C
13: R$^2$ = H, R$^3$ = F, R$^4$ = F, A$^2$ = C

According to reaction formula c, the compounds of Preparative Examples 8 to 13 were obtained. In reaction formula c, 8 is the compound of Preparative Example 8, 9 is the compound of Preparative Example 9, 10 is the compound of Preparative Example 10, 11 is the compound of Preparative Example 11, 12 is the compound of Preparative Example 12, and 13 is the compound of Preparative Example 13.

<Preparative Example 8> Preparation of (R)-(1H-indole-2-yl)(2-methoxyphenyl)methaneamine

[Reaction Formula c]

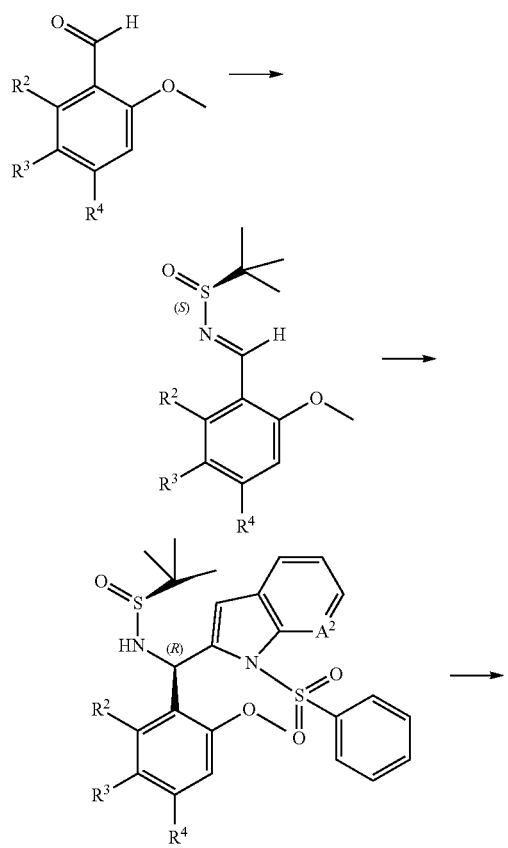

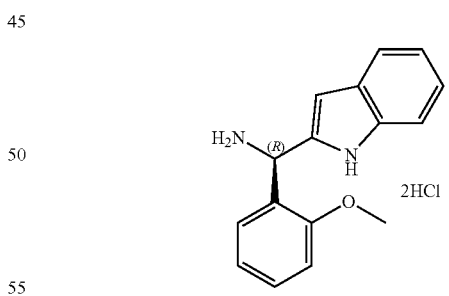

Step 1: Preparation of (S,E)-N-(2-methoxybenzylidene)-2-methylpropane-2-sulfinamide 2-Methoxybenzaldehyde is commercially available. 2-Methoxybenzaldehyde (100 mg, 0.73 mmol), (S)-2-methylpropane-2-sulfinamide (88.5 mg, 0.73 mmol) and titanium (IV) ethoxide (331 mg, 1.45 mmol) were mixed in a reaction flask containing tetrahydrofuran (4 mL). The reaction flask was sealed with a septum, followed by stirring at room temperature for 17 hours. The reaction mixture was extracted with ethyl acetate and water. The ethyl acetate layers were combined, dried over anhydrous magnesium sulfate, and filtered. The solvent was removed using an evaporator under reduced pressure to give (S,E)-N-(2-methoxybenzylidene)-2-methylpropane-2-sulfinamide (157 mg, clear liquid, yield: 90%).

$^1$H NMR (300 MHz, chloroform-d) δ 9.05 (s, 1H), 7.97 (dd, J=7.8, 1.8 Hz, 1H), 7.48-7.41 (m, 1H), 7.02-6.96 (m, 1H), 6.94 (d, J=8.5 Hz, 1H), 3.86 (s, 3H), 1.24 (s, 9H).

Step 2: Preparation of (S)—N—((R)-(2-methoxyphenyl)(1-(phenylsulfonyl)-1H-indole-2-yl)methyl)-2-methylpropane-2-sulfinamide N-butyl lithium was added dropwise to tetrahydrofuran solution (4 mL) of 1-(phenylsulfonyl)-1H-indole (100 mg, 0.29 mmol) at −78° C. After reacting the mixture at −78° C. for 1 hour, THF solution of (S,E)-N-(2-methoxybenzylidene)-2-methylpropane-2-sulfinamide (33.5 mg, 0.09 mmol) was added thereto once (one portion), followed by stirring at −78° C. for 2 hours. The mixture was quenched with saturated NH$_4$Cl aqueous solution, and extracted with ethyl acetate. The ethyl acetate layers were combined, dried over anhydrous magnesium sulfate, and filtered. The solvent was removed using an evaporator under reduced pressure. The residue was purified by silica gel flash column chromatography (CH$_2$Cl$_2$/EtOAc, 10:1) to give (S)—N—((R)-(2-methoxyphenyl)(1-(phenylsulfonyl)-1H-indole-2-yl)methyl)-2-methylpropane-2-sulfinamide (38 mg, white solid, yield: 75%). [Reference: Tetrahedron: *Asymmetry* 2007, 18, 1833.]

$^1$H NMR (300 MHz, chloroform-d) δ 8.11 (d, J=8.2 Hz, 1H), 7.73-7.68 (m, 2H), 7.47-7.45 (m, 1H), 7.37-7.28 (m, 4H), 7.25-7.19 (m, 1H), 7.03-6.93 (m, 2H), 6.82 (q, J=5.4, 4.1 Hz, 2H), 6.71 (s, 1H), 3.91 (s, 3H), 1.24 (s, 9H).

Step 3: Preparation of (R)-(2-methoxyphenyl)(1-(phenylsulfonyl)-1H-indole-2-yl)methaneamine Dioxane (0.16 mL, 0.32 mmol) of 4 N HCl was added to methanol (2 mL) solution of (S)—N—((R)-(2-methoxyphenyl)(1-(phenylsulfonyl)-1H-indole-2-yl)methyl)-2-methylpropane-2-sulfinamide (80 mg, 0.16 mmol) at room temperature. The mixture was concentrated under reduced pressure. The residue was solidified with diethyl ether and filtered to give (R)-(2-methoxyphenyl)(1-(phenylsulfonyl)-1H-indole-2-yl)methaneamine (55.8 mg, pink solid, yield: 89%).

$^1$H NMR (300 MHz, chloroform-d) δ 9.51 (brs, 3H), 7.95 (d, J=8.4 Hz, 1H), 7.81-7.72 (m, 2H), 7.57 (s, 1H), 7.35 (td, J=7.9, 7.5, 1.6 Hz, 1H), 7.15 (td, J=7.5, 3.2 Hz, 3H), 6.99-6.88 (m, 3H), 6.81 (t, J=7.6 Hz, 2H), 6.61 (s, 1H), 3.87 (s, 3H).

Step 4: Preparation of (R)-(1H-indole-2-yl)(2-methoxyphenyl)methaneamine

Water containing 5 NaOH (5 mL, 20 mmol) was added to (R)-(2-methoxyphenyl)(1-(phenylsulfonyl)-1H-indole-2-yl)methaneamine (1100 mg, 2.16 mmol) in methanol (11 mL), followed by refluxing overnight. The mixture was concentrated under reduced pressure. The residue was solidified with ethyl acetate and dioxane containing 4 N HCl (1:1) to give (R)-(1H-indole-2-yl)(2-methoxyphenyl)methaneamine (338 mg, yellow solid, yield: 62%).

$^1$H NMR (300 MHz, methanol-d4) δ 7.58 (d, J=7.8 Hz, 1H), 7.47 (t, J=7.9 Hz, 1H), 7.35 (d, J=8.1 Hz, 1H), 7.26-7.11 (m, 3H), 7.04 (q, J=8.8, 8.4 Hz, 2H), 6.62 (s, 1H), 6.03 (s, 1H), 3.99 (s, J=2.4 Hz, 3H).

<Preparative Example 9> Preparation of (R)-(5-fluoro-2-methoxyphenyl)(1H-indole-2-yl)methaneamine

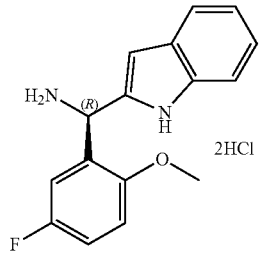

Step 1: Preparation of (S,E)-N-(5-fluoro-2-methoxybenzylidene)-2-methylpropane-2-sulfinamide (S,E)-N-(5-fluoro-2-methoxybenzylidene)-2-methylpropane-2-sulfinamide (157 mg, 90%) was obtained by performing the same method as in step 1 of Preparative Example 8.

$^1$H NMR (500 MHz, chloroform-d) δ 9.03 (d, J=2.4 Hz, 1H), 7.69 (dd, J=8.8, 3.2 Hz, 1H), 7.19 (ddd, J=9.1, 7.7, 3.2 Hz, 1H), 6.94 (dd, J=9.1, 4.1 Hz, 1H), 3.90 (s, 3H), 1.29 (s, 9H).

Step 2: Preparation of (S)—N—((R)-(5-fluoro-2-methoxyphenyl)(1-(phenylsulfonyl)-1H-indole-2-yl)methyl)-2-methylpropane-2-sulfinamide (S)—N—((R)-(5-fluoro-2-methoxyphenyl)(1-(phenylsulfonyl)-1H-indole-2-yl)methyl)-2-methylpropane-2-sulfinamide (4 g, 99%) was obtained by performing the same method as in step 2 of Preparative Example 8.

$^1$H NMR (300 MHz, chloroform-d) δ 8.15 (dd, J=8.3, 1.1 Hz, 1H), 7.76-7.69 (m, 2H), 7.53-7.47 (m, 2H), 7.42-7.30 (m, 3H), 6.98 (ddd, J=8.9, 7.7, 3.0 Hz, 1H), 6.90 (dd, J=9.0, 4.5 Hz, 1H), 6.80 (d, J=5.8 Hz, 1H), 6.76 (d, J=0.9 Hz, 1H), 6.72 (dd, J=9.1, 3.0 Hz, 1H), 3.92 (s, 3H), 1.26 (s, 9H).

Step 3: Preparation of (R)-(5-fluoro-2-methoxyphenyl)(1-(phenylsulfonyl)-1H-indole-2-yl)methaneamine (R)-(5-fluoro-2-methoxyphenyl)(1-(phenylsulfonyl)-1H-indole-2-yl)methaneamine (2.7 g, 84%) was obtained by performing the same method as in step 3 of Preparative Example 8.

$^1$H NMR (300 MHz, chloroform-d) δ 9.69-9.40 (m, 3H), 7.96 (d, J=8.5 Hz, 1H), 7.79 (d, J=7.7 Hz, 2H), 7.58 (s, 1H), 7.26-7.12 (m, 3H), 7.07-6.91 (m, 2H), 6.83 (dd, J=9.1, 4.2 Hz, 1H), 6.71 (s, 1H), 6.57 (d, J=8.5 Hz, 1H), 6.35 (s, 1H), 3.92 (s, 3H).

Step 4: Preparation of (R)-(5-fluoro-2-methoxyphenyl)(1H-indole-2-yl)methaneamine (R)-(5-fluoro-2-methoxyphenyl)(1H-indole-2-yl)methaneamine (1.1 g, 62%) was obtained by performing the same method as in step 4 of Preparative Example 8.

¹H NMR (300 MHz, methanol-d4) δ 7.59 (dt, J=7.8, 1.1 Hz, 1H), 7.40-7.35 (m, 1H), 7.26-7.13 (m, 3H), 7.07 (ddd, J=8.1, 7.1, 1.1 Hz, 1H), 6.99 (dd, J=8.9, 2.7 Hz, 1H), 6.62 (t, J=0.9 Hz, 1H), 6.01 (s, 1H), 3.97 (s, 3H), 3.68 (s, 3H).

<Preparative Example 10> Preparation of (R)-(5-chloro-2-methoxyphenyl)(1H-indole-2-yl)methaneamine

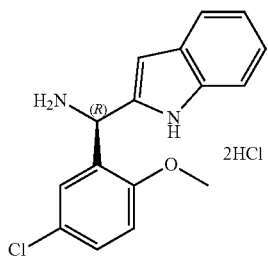

Step 1: Preparation of (S,E)-N-(5-chloro-2-methoxybenzylidene)-2-methylpropane-2-sulfinamide (S,E)-N-(5-chloro-2-methoxybenzylidene)-2-methylpropane-2-sulfinamide (7.2 g, 90%) was obtained by performing the same method as in step 1 of Preparative Example 8.
¹H NMR (500 MHz, chloroform-d) δ 9.01 (s, 1H), 7.96 (d, J=2.7 Hz, 1H), 7.43 (dd, J=8.9, 2.7 Hz, 1H), 6.93 (d, J=8.9 Hz, 1H), 3.91 (s, 3H), 1.29 (s, 9H).

Step 2: Preparation of (S)—N—((R)-(5-chloro-2-methoxyphenyl)(1-(phenylsulfonyl)-1H-indole-2-yl)methyl)-2-methylpropane-2-sulfinamide (S)—N—((R)-(5-chloro-2-methoxyphenyl)(1-(phenylsulfonyl)-1H-indole-2-yl)methyl)-2-methylpropane-2-sulfinamide (15 g, 96%) was obtained by performing the same method as in step 2 of Preparative Example 8. This compound was used in the next step without further purification.

Step 3: Preparation of (R)-(5-chloro-2-methoxyphenyl)(1-(phenylsulfonyl)-1H-indole-2-yl)methaneamine (R)-(5-chloro-2-methoxyphenyl)(1-(phenylsulfonyl)-1H-indole-2-yl)methaneamine (10 g, 80%) was obtained by performing the same method as in step 3 of Preparative Example 8.
¹H NMR (300 MHz, methanol-d4) δ 8.20 (dt, J=8.5, 0.9 Hz, 1H), 7.77-7.70 (m, 2H), 7.64-7.58 (m, 2H), 7.51-7.41 (m, 5H), 7.33 (td, J=7.6, 1.0 Hz, 1H), 7.21 (d, J=8.9 Hz, 1H), 7.13 (d, J=2.6 Hz, 1H), 6.81 (t, J=0.9 Hz, 1H), 6.71 (s, 1H), 3.95 (s, 3H).

Step 4: Preparation of (R)-(5-chloro-2-methoxyphenyl)(1H-indole-2-yl)methaneamine (R)-(5-chloro-2-methoxyphenyl)(1H-indole-2-yl)methaneamine (4 g, 60%) was obtained by performing the same method as in step 4 of Preparative Example 8.
¹H NMR (300 MHz, methanol-d4) δ 7.58 (d, J=7.8 Hz, 1H), 7.43 (dd, J=8.8, 2.6 Hz, 1H), 7.37 (dd, J=8.0, 1.1 Hz, 1H), 7.22 (d, J=2.6 Hz, 1H), 7.19-7.11 (m, 2H), 7.10-7.02 (m, 1H), 6.59 (s, 1H), 5.96 (s, 1H), 3.96 (s, 3H).

<Preparative Example 11> Preparation of (R)-(1H-indole-2-yl)(2-methoxy-5-methylphenyl)methaneamine

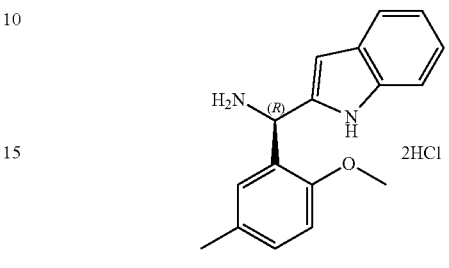

Step 1: Preparation of (S,E)-N-(2-methoxy-5-methylbenzylidene)-2-methylpropane-2-sulfinamide (S,E)-N-(2-methoxy-5-methylbenzylidene)-2-methylpropane-2-sulfinamide (717 mg, 85%) was obtained by performing the same method as in step 1 of Preparative Example 8.
¹H NMR (500 MHz, chloroform-d) δ 9.05 (s, 1H), 7.78 (d, J=2.3 Hz, 1H), 7.30-7.26 (m, 1H), 6.87 (d, J=8.4 Hz, 1H), 3.87 (s, 3H), 2.34 (s, 3H), 1.28 (s, 9H).

Step 2: Preparation of (S)—N—((R)-(2-methoxy-5-methylphenyl)(1-(phenylsulfonyl)-1H-indole-2-yl)methyl)-2-methylpropane-2-sulfinamide (S)—N—((R)-(2-methoxy-5-methylphenyl)(1-(phenylsulfonyl)-1H-indole-2-yl)methyl)-2-methylpropane-2-sulfinamide (3.8 g, 52%) was obtained by performing the same method as in step 2 of Preparative Example 8.
¹H NMR (300 MHz, chloroform-d) δ 8.19-8.13 (m, 1H), 7.70-7.65 (m, 2H), 7.53-7.44 (m, 2H), 7.33 (td, J=7.5, 6.8, 1.6 Hz, 3H), 7.25 (dd, J=7.4, 1.1 Hz, 1H), 7.12-7.05 (m, 1H), 6.88 (d, J=8.3 Hz, 1H), 6.83-6.74 (m, 3H), 3.93 (s, 4H), 2.13 (s, 3H), 1.26 (s, 9H).

Step 3: Preparation of (R)-(2-methoxy-5-methylphenyl)(1-(phenylsulfonyl)-1H-indole-2-yl)methaneamine (R)-(2-methoxy-5-methylphenyl)(1-(phenylsulfonyl)-1H-indole-2-yl)methaneamine (2.5 g, 83%) was obtained by performing the same method as in step 3 of Preparative Example 8.
¹H NMR (300 MHz, chloroform-d) δ 9.41 (s, 3H), 7.98 (d, J=8.4 Hz, 1H), 7.73-7.67 (m, 2H), 7.57 (s, 1H), 7.28 (d, J=3.3 Hz, 2H), 7.17-7.10 (m, 4H), 6.81 (tt, J=16.5, 7.6 Hz, 4H), 6.68 (d, J=2.1 Hz, 1H), 3.86 (s, 3H), 2.09 (s, 3H).

Step 4: Preparation of (R)-(1H-indole-2-yl)(2-methoxy-5-methylphenyl)methaneamine (R)-(1H-indole-2-yl)(2-methoxy-5-methylphenyl)methaneamine (1 g, 61%) was obtained by performing the same method as in step 4 of Preparative Example 8.
¹H NMR (300 MHz, methanol-d4) δ 7.60-7.54 (m, 1H), 7.35 (dd, J=8.1, 1.1 Hz, 1H), 7.26 (dd, J=8.4, 2.2 Hz, 1H), 7.14 (ddd, J=8.2, 7.1, 1.3 Hz, 1H), 7.09-7.05 (m, 2H), 7.03 (d, J=2.0 Hz, 2H), 6.60 (s, 1H), 5.95 (s, 1H), 3.94 (s, 3H).

<Preparative Example 12> Preparation of (R)-(2,3-difluoro-6-methoxyphenyl)(1H-indole-2-yl)methaneamine

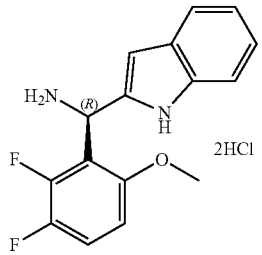

Step 1: Preparation of (S,E)-N-(2,3-difluoro-6-methoxybenzylidene)-2-methylpropane-2-sulfinamide (S,E)-N-(2,3-difluoro-6-methoxybenzylidene)-2-methylpropane-2-sulfinamide (1.4 g, 88%) was obtained by performing the same method as in step 1 of Preparative Example 8.

$^1$H NMR (500 MHz, chloroform-d) δ 8.88 (d, J=2.6, 1H), 7.24 (dd, J=3.5, 2.0 Hz, 1H), 6.66 (ddd, J=9.3, 3.5, 2.0 Hz, 1H), 3.88 (s, 3H), 1.27 (s, 9H).

Step 2: Preparation of (S)—N—((R)-(2,3-difluoro-6-methoxyphenyl)(1-(phenylsulfonyl)-1H-indole-2-yl)methyl)-2-methylpropane-2-sulfinamide (S)—N—((R)-(2,3-difluoro-6-methoxyphenyl)(1-(phenylsulfonyl)-1H-indole-2-yl)methyl)-2-methylpropane-2-sulfinamide (812 mg, 42%) was obtained by performing the same method as in step 2 of Preparative Example 8.

$^1$H NMR (500 MHz, chloroform-d) δ 8.12 (dd, J=8.5, 0.9 Hz, 1H), 7.83-7.79 (m, 2H), 7.53-7.48 (m, 1H), 7.42-7.36 (m, 3H), 7.32 (ddd, J=8.5, 7.3, 1.3 Hz, 1H), 7.23-7.19 (m, 1H), 7.16 (q, J=9.3 Hz, 1H), 6.85 (d, J=10.2 Hz, 1H), 6.77-6.72 (m, 1H), 6.39 (s, 1H), 3.92 (s, 3H), 1.30 (s, 9H).

Step 3: Preparation of (R)-(2,3-difluoro-6-methoxyphenyl)(1-(phenylsulfonyl)-1H-indole-2-yl)methaneamine (R)-(2,3-difluoro-6-methoxyphenyl)(1-(phenylsulfonyl)-1H-indole-2-yl)methaneamine (950 mg, 82%) was obtained by performing the same method as in step 3 of Preparative Example 8.

$^1$H NMR (300 MHz, methanol-d4) δ 8.22 (d, J=8.5 Hz, 1H), 7.90-7.82 (m, 2H), 7.70-7.62 (m, 1H), 7.57-7.42 (m, 5H), 7.35-7.27 (m, 1H), 7.07 (ddd, J=9.5, 3.6, 2.0 Hz, 1H), 6.73 (d, J=1.1 Hz, 1H), 6.66 (s, 1H), 3.94 (s, 3H).

Step 4: Preparation of (R)-(2,3-difluoro-6-methoxyphenyl)(1H-indole-2-yl)methaneamine (R)-(2,3-difluoro-6-methoxyphenyl)(1H-indole-2-yl)methaneamine (266 m g, 60%) was obtained by performing the same method as in step 4 of Preparative Example 8.

$^1$H NMR (300 MHz, methanol-d4) δ 7.54 (d, J=7.9 Hz, 1H), 7.39 (dd, J=11.1, 8.7 Hz, 2H), 7.18-7.11 (m, 1H), 7.06 (d, J=7.6 Hz, 1H), 6.99 (ddd, J=9.4, 5.1, 2.8 Hz, 1H), 6.60 (s, 1H), 6.14 (s, 1H), 3.93 (s, 3H).

<Preparative Example 13> Preparation of (R)-(4,5-difluoro-2-methoxyphenyl)(1H-indole-2-yl)methaneamine

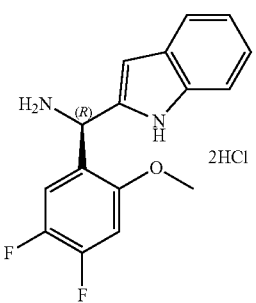

Step 1: Preparation of (S,E)-N-(4,5-difluoro-2-methoxybenzylidene)-2-methylpropane-2-sulfinamide (S,E)-N-(4,5-difluoro-2-methoxybenzylidene)-2-methylpropane-2-sulfinamide (1.6 g, 100%) was obtained by performing the same method as in step 1 of Preparative Example 8.

$^1$H NMR (300 MHz, chloroform-d) δ 8.93 (d, J=2.3 Hz, 1H), 7.80 (dd, J=10.7, 9.2 Hz, 1H), 6.78 (dd, J=11.8, 6.3 Hz, 1H), 3.87 (s, 3H), 1.25 (s, 9H).

Step 2: Preparation of (S)—N—((R)-(4,5-difluoro-2-methoxyphenyl)(1-(phenylsulfonyl)-1H-indole-2-yl)methyl)-2-methylpropane-2-sulfinamide (S)—N—((R)-(4,5-difluoro-2-methoxyphenyl)(1-(phenylsulfonyl)-1H-indole-2-yl)methyl)-2-methylpropane-2-sulfinamide (849 mg, 87%) was obtained by performing the same method as in step 2 of Preparative Example 8.

$^1$H NMR (300 MHz, chloroform-d) δ 8.17 (dd, J=8.2, 1.0 Hz, 1H), 7.73-7.68 (m, 2H), 7.56-7.49 (m, 2H), 7.41-7.35 (m, 2H), 7.32 (dd, J=6.4, 1.4 Hz, 1H), 6.82-6.74 (m, 4H), 3.92 (s, 3H), 1.26 (s, 9H).

Step 3: Preparation of (R)-(4,5-difluoro-2-methoxyphenyl)(1-(phenylsulfonyl)-1H-indole-2-yl)methaneamine (R)-(4,5-difluoro-2-methoxyphenyl)(1-(phenylsulfonyl)-1H-indole-2-yl)methaneamine (660 mg, 95%) was obtained by performing the same method as in step 3 of Preparative Example 8.

$^1$H NMR (300 MHz, methanol-d4) δ 8.21 (dd, J=8.5, 1.0 Hz, 1H), 7.79-7.73 (m, 2H), 7.66-7.59 (m, 2H), 7.52-7.43 (m, 3H), 7.34 (td, J=7.5, 1.0 Hz, 1H), 7.23 (dd, J=12.2, 6.6 Hz, 1H), 7.06 (dd, J=10.8, 8.6 Hz, 1H), 6.83 (t, J=1.0 Hz, 1H), 6.68 (s, 1H), 3.94 (s, 3H).

Step 4: Preparation of (R)-(4,5-difluoro-2-methoxyphenyl)(1H-indole-2-yl)methaneamine (R)-(4,5-difluoro-2-methoxyphenyl)(1H-indole-2-yl)methaneamine (387 mg, 63%) was obtained by performing the same method as in step 4 of Preparative Example 8.

¹H NMR (300 MHz, chloroform-d) δ 8.57 (brs, 1H), 7.60-7.53 (m, 1H), 7.38-7.32 (m, 1H), 7.23-7.06 (m, 3H), 6.76 (dd, J=11.9, 6.5 Hz, 1H), 6.31 (dt, J=2.1, 1.0 Hz, 1H), 5.65 (s, 1H), 3.86 (s, 3H).

<Preparative Example 14> Preparation of (S)-(5-fluoro-2-methoxyphenyl)(1H-indole-2-yl)methaneamine

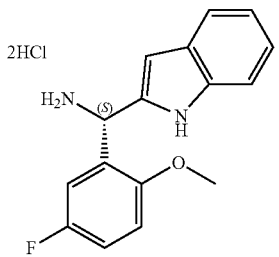

Step 1: Preparation of (R,E)-N-(5-fluoro-2-methoxybenzylidene)-2-methylpropane-2-sulfinamide (R,E)-N-(5-fluoro-2-methoxybenzylidene)-2-methylpropane-2-sulfinamide (7.5 g, 90%) was obtained by performing the same method as in step 1 of Preparative Example 8.
¹H NMR (500 MHz, chloroform-d) δ 9.03 (d, J=2.4 Hz, 1H), 7.69 (dd, J=8.8, 3.2 Hz, 1H), 7.19 (ddd, J=9.1, 7.7, 3.2 Hz, 1H), 6.94 (dd, J=9.1, 4.1 Hz, 1H), 3.90 (s, 3H), 1.29 (s, 9H).

Step 2: Preparation of (S)—N—((S)-(5-fluoro-2-methoxyphenyl)(1-(phenylsulfonyl)-1H-indole-2-yl)methyl)-2-methylpropane-2-sulfinamide (S)—N—((S)-(5-fluoro-2-methoxyphenyl)(1-(phenylsulfonyl)-1H-indole-2-yl)methyl)-2-methylpropane-2-sulfinamide (1.2 g, 50%) was obtained by performing the same method as in step 2 of Preparative Example 8.
¹H NMR (300 MHz, chloroform-d) δ 8.18-8.12 (m, 1H), 7.76-7.68 (m, 2H), 7.51-7.42 (m, 2H), 7.38-7.20 (m, 4H), 6.95 (ddd, J=9.0, 7.7, 3.0 Hz, 1H), 6.87 (dd, J=9.0, 4.5 Hz, 1H), 6.81 (d, J=6.0 Hz, 1H), 6.78-6.72 (m, 2H), 3.99 (d, J=6.0 Hz, 1H), 3.88 (s, 3H), 1.24 (s, 9H).

Step 3: Preparation of (S)-(5-fluoro-2-methoxyphenyl)(1-(phenylsulfonyl)-1H-indole-2-yl)methaneamine (S)-(5-fluoro-2-methoxyphenyl)(1-(phenylsulfonyl)-1H-indole-2-yl)methaneamine (4.1 g, 90%) was obtained by performing the same method as in step 3 of Preparative Example 8.
¹H NMR (300 MHz, methanol-d₄) δ 8.21 (dd, J=8.5, 1.0 Hz, 1H), 7.83-7.76 (m, 2H), 7.69-7.61 (m, 1H), 7.59 (dt, J=7.7, 1.0 Hz, 1H), 7.47 (ddd, J=14.4, 8.4, 7.1 Hz, 3H), 7.33 (td, J=7.6, 0.9 Hz, 1H), 7.28-7.18 (m, 2H), 6.97 (dd, J=8.9, 2.8 Hz, 1H), 6.76-6.71 (m, 2H), 3.93 (s, 3H).

Step 4: Preparation of (S)-(5-fluoro-2-methoxyphenyl)(1H-indole-2-yl)methaneamine (S)-(5-fluoro-2-methoxyphenyl)(1H-indole-2-yl)methaneamine (500 mg, 85%) was obtained by performing the same method as in step 4 of Preparative Example 8.

¹H NMR (500 MHz, chloroform-d) δ 8.84 (s, 1H), 7.60 (d, J=7.8 Hz, 1H), 7.35 (d, J=7.9 Hz, 1H), 7.21-7.16 (m, 1H), 7.15-7.06 (m, 2H), 6.98 (td, J=8.2, 7.7, 3.0 Hz, 1H), 6.88 (dd, J=9.0, 4.3 Hz, 1H), 6.34 (s, 1H), 5.68 (s, 1H), 2.29-2.22 (m, 2H).

<Preparative Example 15> Preparation of (R)-(2-fluoro-6-methoxyphenyl)(1H-indole-2-yl)methaneamine

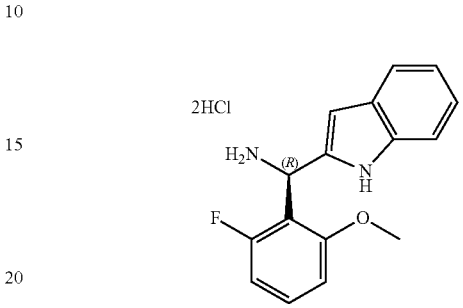

Step 1: Preparation of (S,E)-N-(2-fluoro-6-methoxybenzylidene)-2-methylpropane-2-sulfinamide (S,E)-N-(2-fluoro-6-methoxybenzylidene)-2-methylpropane-2-sulfinamide (1.6 g, 100%) was obtained by performing the same method as in step 1 of Preparative Example 8.
¹H NMR (300 MHz, chloroform-d) δ 8.94 (d, J=1.3 Hz, 1H), 7.42 (td, J=8.5, 6.3 Hz, 1H), 6.78 (dt, J=9.2, 5.1 Hz, 2H), 3.95-3.91 (m, 3H), 1.29 (d, J=1.3 Hz, 9H).

Step 2: Preparation of (S)—N—((R)-(2-fluoro-6-methoxyphenyl)(1-(phenylsulfonyl)-1H-indole-2-yl)methyl)-2-methylpropane-2-sulfinamide (S)—N—((R)-(2-fluoro-6-methoxyphenyl)(1-(phenylsulfonyl)-1H-indole-2-yl)methyl)-2-methylpropane-2-sulfinamide (1.3 g, 42%) was obtained by performing the same method as in step 2 of Preparative Example 8.
¹H NMR (300 MHz, chloroform-d) δ 8.11 (dd, J=8.4, 1.0 Hz, 1H), 7.86-7.79 (m, 2H), 7.53-7.45 (m, 1H), 7.42-7.29 (m, 5H), 7.19 (td, J=7.5, 1.0 Hz, 1H), 6.85 (dd, J=14.8, 9.7 Hz, 3H), 6.38 (q, J=1.0 Hz, 1H), 3.94 (s, 3H), 1.30 (s, 9H).

Step 3: Preparation of (R)-(2-fluoro-6-methoxyphenyl)(1-(phenylsulfonyl)-1H-indole-2-yl)methaneamine (R)-(2-fluoro-6-methoxyphenyl)(1-(phenylsulfonyl)-1H-indole-2-yl)methaneamine (830 mg, 96%) was obtained by performing the same method as in step 3 of Preparative Example 8.
¹H NMR (500 MHz, methanol-d₄) δ 8.22 (dd, J=8.5, 0.9 Hz, 1H), 7.90-7.85 (m, 2H), 7.69-7.64 (m, 1H), 7.60 (td, J=8.5, 6.7 Hz, 1H), 7.55-7.48 (m, 3H), 7.44 (ddd, J=8.5, 7.2, 1.3 Hz, 1H), 7.32-7.27 (m, 1H), 7.12 (d, J=8.5 Hz, 1H), 6.98 (ddd, J=10.3, 8.5, 0.9 Hz, 1H), 6.74 (s, 1H), 6.60-6.57 (m, 1H), 3.97 (s, 3H).

Step 4: Preparation of (R)-(2-fluoro-6-methoxyphenyl)(1H-indole-2-yl)methaneamine (R)-(2-fluoro-6-methoxyphenyl)(1H-indole-2-yl)methaneamine (353 mg, 92%) was obtained by performing the same method as in step 4 of Preparative Example 8.

¹H NMR (500 MHz, methanol-d₄) δ 7.54 (dt, J=7.9, 1.0 Hz, 1H), 7.50 (dd, J=8.5, 6.8 Hz, 1H), 7.38 (dq, J=8.2, 1.1 Hz, 1H), 7.14 (ddd, J=8.2, 7.0, 1.2 Hz, 1H), 7.08-7.00 (m, 2H), 6.93 (ddd, J=9.6, 8.5, 0.9 Hz, 1H), 6.58 (q, J=1.0 Hz, 1H), 6.14 (s, 1H), 3.98 (s, 3H).

¹H NMR (300 MHz, methanol-d₄) δ 8.79 (dd, J=8.0, 1.3 Hz, 1H), 8.50 (dd, J=6.0, 1.3 Hz, 1H), 7.67 (ddd, J=7.4, 5.9, 1.5 Hz, 1H), 7.33-7.18 (m, 2H), 7.14-7.08 (m, 2H), 6.20 (s, 1H), 3.98 (s, 3H).

<Preparative Example 16> Preparation of (S)-(5-fluoro-2-methoxyphenyl)(1H-pyrrolo[2,3-b]pyridine-2-yl)methaneamine

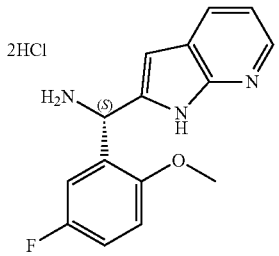

Step 1: Preparation of (S)—N—((S)-(5-fluoro-2-methoxyphenyl)(1-(phenylsulfonyl)-1H-pyrrolo[2,3-b]pyridine-2-yl)methyl)-2-methylpropane-2-sulfinamide (S)—N—((S)-(5-fluoro-2-methoxyphenyl)(1-(phenylsulfonyl)-1H-pyrrolo[2,3-b]pyridine-2-yl)methyl)-2-methylpropane-2-sulfinamide (1.1 g, 50%) was obtained by performing the same method as in step 2 of Preparative Example 8.

¹H NMR (500 MHz, chloroform-d) δ 8.44 (dd, J=4.8, 1.6 Hz, 1H), 7.87-7.84 (m, 2H), 7.82 (dd, J=7.8, 1.6 Hz, 1H), 7.51 (ddt, J=8.8, 7.3, 1.3 Hz, 1H), 7.39-7.34 (m, 2H), 7.21 (dd, J=7.8, 4.8 Hz, 1H), 7.03 (ddd, J=9.0, 7.8, 3.1 Hz, 1H), 6.97 (td, J=9.0, 8.2, 5.1 Hz, 2H), 6.80 (d, J=1.1 Hz, 1H), 6.65 (dd, J=8.9, 3.0 Hz, 1H), 3.97 (s, 3H), 1.29 (s, 9H).

Step 2: Preparation of (S)-(5-fluoro-2-methoxyphenyl)(1-(phenylsulfonyl)-1H-pyrrolo[2,3-b]pyridine-2-yl)methaneamine (R)-(5-fluoro-2-methoxyphenyl)(1H-indole-2-yl)methaneamine (819 mg, 94%) was obtained by performing the same method as in step 3 of Preparative Example 8.

¹H NMR (500 MHz, methanol-d₄) δ 8.80 (dd, J=7.9, 1.2 Hz, 1H), 8.50 (dd, J=6.0, 1.2 Hz, 1H), 7.95-7.90 (m, 1H), 7.81 (dt, J=8.0, 1.5 Hz, 1H), 7.71-7.65 (m, 1H), 7.50 (t, J=7.9 Hz, 1H), 7.45-7.41 (m, 1H), 7.30-7.25 (m, 2H), 7.22 (dd, J=9.2, 4.4 Hz, 1H), 7.12 (s, 1H), 6.85 (s, 1H), 6.20 (s, 1H), 3.97 (s, 3H).

Step 3: Preparation of (S)-(5-fluoro-2-methoxyphenyl)(1H-pyrrolo[2,3-b]pyridine-2-yl)methaneamine (S)-(5-fluoro-2-methoxyphenyl)(1H-pyrrolo[2,3-b]pyridine-2-yl)methaneamine (705 mg, 70%) was obtained by performing the same method as in step 4 of Preparative Example 8.

[Reaction Formula d]

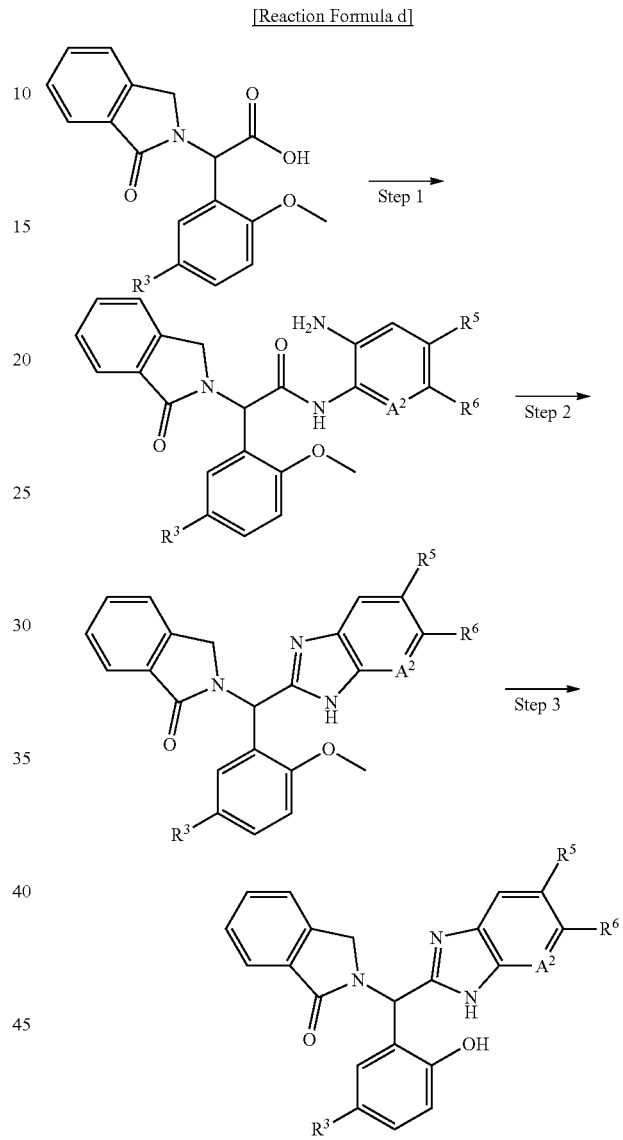

1: R³ = H, A² = C, R⁶ = H, R⁵ = H
2: R³ = H, A² = C, R⁶ = H, R⁵ = H
3: R³ = H, A² = N, R⁶ = H, R⁵ = H
4: R³ = H, A² = C, R⁶ = Cl, R⁵ = H
5: R³ = H, A² = C, R⁶ = Cl, R⁵ = Cl
6: R³ = H, A² = N, R⁶ = Cl, R⁵ = H
7: R³ = F, A² = C, R⁶ = H, R⁵ = H
8: R³ = Cl, A² = C, R⁶ = H, R⁵ = H

According to reaction formula d, the compounds of Examples 1 to 8 were obtained. In reaction formula d, 1 is the compound of Example 1, 2 is the compound of Example 2, 3 is the compound of Example 3, 4 is the compound of Example 4, 5 is the compound of Example 5, 6 is the compound of Example 6, 7 is the compound of Example 7, and 8 is the compound of Example 8.

<Example 1> Preparation of 2-((1H-benzo[d]imidazole-2-yl)(2-hydroxyphenyl)methyl)isoindolin-1-one Step 1: Preparation of N-(2-aminophenyl)-2-(2-methoxyphenyl)-2-(1-oxoisoindole-2-yl)acetamide Diisopropylethylamine (0.26 mL, 1.5 mmol) was added to 2-(2-methoxyphenyl)-2-(1-oxoisoindole-2-yl)acetic acid (150 mg, 0.5 mmol), benzene-1,2-diamine (65 mg, 0.6 mmol) and HATU (380 mg, 1 mmol) in N,N-dimethylformamide (2 mL) solution. After stirring at room temperature for 6 hours, the reaction mixture was diluted with ethyl acetate and washed several times with water. The organic layer was dried over $MgSO_4$, filtered, and concentrated under reduced pressure to give crude N-(2-aminophenyl)-2-(2-methoxyphenyl)-2-(1-oxoisoindole-2-yl)acetamide, which was used in the next step without further purification.

Step 2: Preparation of 2-((1H-benzo[d]imidazole-2-yl)(2-methoxyphenyl)methyl)isoindolin-1-one Crude (2-aminophenyl)-2-(2-methoxyphenyl)-2-(1-oxoisoindole-2-yl)acetamide in acetic acid (5 mL) was refluxed overnight. The reaction mixture was cooled to room temperature and concentrated under reduced pressure. The residue was fractionated as ethyl acetate and water. The combined organic layer was dried over $MgSO_4$, filtered and concentrated under reduced pressure. The residue was triturated with methylene chloride and n-hexane to give 2-((1H-benzo[d]imidazole-2-yl)(2-methoxyphenyl)methyl)isoindolin-1-one (128 mg, yellow oil, 2 steps yield: 69%).
$^1$H NMR (300 MHz, chloroform-d) δ 7.75 (dd, J=7.3, 1.4 Hz, 1H), 7.59 (dd, J=6.1, 3.2 Hz, 2H), 7.52-7.42 (m, 2H), 7.39 (d, J=7.7 Hz, 2H), 7.32-7.19 (m, 4H), 6.94 (td, J=7.6, 1.0 Hz, 1H), 6.79 (d, J=8.2 Hz, 1H), 4.86 (d, J=17.6 Hz, 1H), 4.45 (d, J=17.6 Hz, 1H), 3.54 (s, 3H).

Step 3: Preparation of 2-((1H-benzo[d]imidazole-2-yl)(2-hydroxyphenyl)methyl)isoindolin-1-one Methylene chloride (0.2 mL) containing 1 M boron tribromide was slowly added to 2-((1H-benzo[d]imidazole-2-yl)(2-methoxyphenyl)methyl)isoindolin-1-one (10 mg, 0.027 mmol) at −78° C. The reaction mixture was stirred at room temperature for 20 minutes and quenched with water. The reaction mixture was extracted three times with ethyl acetate and water. The combined organic layer was dried over $MgSO_4$, filtered and concentrated. The residue was purified by reverse-phase semi-prep HPLC to give 2-((1H-benzo[d]imidazole-2-yl)(2-hydroxyphenyl)methyl)isoindolin-1-one (5.5 mg, white solid, yield: 59%).
$^1$H NMR (300 MHz, methanol-$d_4$) δ 7.90 (dd, J=7.3, 1.5 Hz, 1H), 7.73 (dd, J=6.2, 3.2 Hz, 2H), 7.74-7.64 (m, 1H), 7.64-7.55 (m, 4H), 7.44 (dd, J=7.7, 1.7 Hz, 1H), 7.39 (dd, J=8.0, 1.6 Hz, 1H), 7.17 (s, 1H), 7.05 (dd, J=7.6, 1.1 Hz, 1H), 7.06-6.96 (m, 2H), 4.81 (d, J=17.3 Hz, 1H), 4.31 (d, J=17.3 Hz, 1H); LC-MS (M+H$^+$) calcd for $C_{22}H_{17}N_3O_2$ 355.1, found 356.1.

<Example 2> Preparation of 2-((6-fluoro-1H-benzo[d]imidazole-2-yl)(2-hydroxyphenyl)methyl)isoindolin-1-one Step 1: Preparation of N-(2-amino-5-fluorophenyl)-2-(2-methoxyphenyl)-2-(1-oxoisoindole-2-yl)acetamide Crude N-(2-amino-5-fluorophenyl)-2-(2-methoxyphenyl)-2-(1-oxoisoindole-2-yl)acetamide was obtained by performing the same method as in step 1 of Example 1.

Step 2: Preparation of 2-((6-fluoro-1H-benzo[d]imidazole-2-yl)(2-methoxyphenyl)methyl)isoindolin-1-one 2-((6-Fluoro-1H-benzo[d]imidazole-2-yl)(2-methoxyphenyl)methyl)isoindolin-1-one (95 mg, 2 steps yield: 77%) was obtained by performing the same method as in step 2 of Example 1.
$^1$H NMR (500 MHz, chloroform-d) δ 7.58-7.50 (m, 3H), 7.43 (d, J=7.6 Hz, 1H), 7.36 (td, J=7.8, 6.5 Hz, 2H), 7.31 (dd, J=7.7, 1.6 Hz, 1H), 7.21 (dd, J=8.0, 2.4 Hz, 1H), 7.19 (s, 1H), 7.10 (td, J=9.1, 2.4 Hz, 1H), 6.94 (ddd, J=15.1, 8.0, 1.0 Hz, 2H), 4.74 (d, J=17.4 Hz, 1H), 4.54 (d, J=17.4 Hz, 1H), 3.67 (s, 3H).

Step 3: Preparation of 2-((6-fluoro-1H-benzo[d]imidazole-2-yl)(2-hydroxyphenyl)methyl)isoindolin-1-one 2-((6-Fluoro-1H-benzo[d]imidazole-2-yl)(2-hydroxyphenyl)methyl)isoindolin-1-one (8.2 mg, 43%) was obtained by performing the same method as in step 3 of Example 1.
$^1$H NMR (500 MHz, methanol-$d_4$) δ 7.88 (dd, J=7.9, 3.2 Hz, 1H), 7.74-7.66 (m, 2H), 7.61-7.55 (m, 2H), 7.46 (dd, J=8.3, 2.4 Hz, 1H), 7.41 (td, J=7.8, 1.7 Hz, 1H), 7.39-7.32 (m, 2H), 7.16 (s, 1H), 7.04-6.99 (m, 2H), 4.80 (d, J=17.3 Hz, 1H), 4.30 (d, J=17.4 Hz, 1H); LC-MS (M+H$^+$) calcd for $C_{22}H_{16}FN_3O_2$ 373.1, found 374.0.

<Example 3> Preparation of 2-((2-hydroxyphenyl)(3H-imidazo[4,5-b]pyridine-2-yl)methyl)isoindolin-1-one Step 1: Preparation of N-(2-aminopyridine-3-yl)-2-(2-methoxyphenyl)-2-(1-oxoisoindole-2-yl) acetamide Crude N-(3-aminopyridine-2-yl)-2-(2-methoxyphenyl)-2-(1-oxoisoindole-2-yl)acetamide was obtained by performing the same method as in step 1 of Example 1.

Step 2: Preparation of 2-((3H-imidazo[4,5-b]pyridine-2-yl)(2-methoxyphenyl)methyl)isoindolin-1-one 2-((3H-imidazo[4,5-b]pyridine-2-yl)(2-methoxyphenyl)methyl)isoindolin-1-one (92 mg, 2 steps yield 78%) was obtained by performing the same method as in step 2 of Example 1.
$^1$H NMR (500 MHz, chloroform-d) δ 8.38 (d, J=5.5 Hz, 1H), 8.30 (d, J=8.0 Hz, 1H), 7.77 (d, J=7.7 Hz, 1H), 7.56 (td, J=7.6, 1.1 Hz, 1H), 7.43 (dt, J=7.5, 3.6 Hz, 3H), 7.37 (td, J=7.9, 1.6 Hz, 1H), 7.31 (s, 1H), 7.28-7.24 (m, 1H), 6.98-6.89 (m, 2H), 4.86 (d, J=17.2 Hz, 1H), 4.26 (d, J=17.2 Hz, 1H), 3.70 (s, 3H).

Step 3: Preparation of 2-((2-hydroxyphenyl)(3H-imidazo[4,5-b]pyridine-2-yl)methyl)isoindolin-1-one 2-((2-Hydroxyphenyl)(3H-imidazo[4,5-b]pyridine-2-yl)methyl)isoindolin-1-one (12 mg, 66%) was obtained by performing the same method as in step 3 of Example 1.
$^1$H NMR (500 MHz, methanol-$d_4$) δ 8.56 (dd, J=5.6, 1.3 Hz, 1H), 8.39 (dd, J=8.1, 1.2 Hz, 1H), 7.85 (d, J=7.6 Hz, 1H), 7.68-7.63 (m, 2H), 7.59-7.52 (m, 2H), 7.34 (td, J=7.8, 1.7 Hz, 1H), 7.24 (s, 1H), 7.18 (dd, J=7.7, 1.6 Hz, 1H), 6.97 (dd, J=8.2, 1.1 Hz, 1H), 6.94 (td, J=7.5, 1.1 Hz, 1H), 4.90 (d, J=17.4 Hz, 1H), 4.22 (d, J=17.4 Hz, 1H); LC-MS (M+H⁺) calcd for $C_{21}H_{16}N_4O_2$ 356.1, found 357.1.

<Example 4> Preparation of 2-((6-chloro-1H-benzo[d]imidazole-2-yl)(2-hydroxyphenyl)methyl)isoindolin-1-one Step 1: Preparation of N-(2-amino-5-chlorophenyl)-2-(2-methoxyphenyl)-2-(1-oxoisoindole-2-yl)acetamide Crude N-(2-amino-4 or 5-chlorophenyl)-2-(2-methoxyphenyl)-2-(1-oxoisoindole-2-yl)acetamide was obtained by performing the same method as in step 1 of Example 1.

Step 2: Preparation of 2-((6-chloro-1H-benzo[d]imidazole-2-yl)(2-methoxyphenyl)methyl)isoindolin-1-one 2-((6-Chloro-1H-benzo[d]imidazole-2-yl)(2-methoxyphenyl)methyl)isoindolin-1-one (68 mg, 2 steps yield 50%) was obtained by performing the same method as in step 2 of Example 1.
¹H NMR (300 MHz, chloroform-d) δ 7.57 (d, J=7.4 Hz, 1H), 7.40 (q, J=8.4, 6.5 Hz, 4H), 7.33-7.23 (m, 3H), 7.14 (s, 2H), 6.85 (d, J=7.1 Hz, 1H), 6.80 (d, J=8.2 Hz, 1H), 4.84 (d, J=17.0 Hz, 1H), 4.50 (d, J=16.7 Hz, 1H), 3.54 (s, 3H).

Step 3: Preparation of 2-((6-chloro-1H-benzo[d]imidazole-2-yl)(2-hydroxyphenyl)methyl)isoindolin-1-one 2-((6-Chloro-1H-benzo[d]imidazole-2-yl)(2-hydroxyphenyl)methyl)isoindolin-1-one (9.3 mg, 64%) was obtained by performing the same method as in step 3 of Example 1.
¹H NMR (300 MHz, methanol-d₄) δ 7.88 (dt, J=7.5, 1.1 Hz, 1H), 7.71 (dd, J=2.0, 0.7 Hz, 1H), 7.69-7.64 (m, 2H), 7.61-7.57 (m, 2H), 7.53 (dd, J=8.8, 1.9 Hz, 1H), 7.39 (ddd, J=8.1, 7.4, 1.7 Hz, 1H), 7.34-7.29 (m, 1H), 7.16 (s, 1H), 7.00 (t, J=7.2 Hz, 2H), 4.80 (d, J=17.4 Hz, 1H), 4.28 (d, J=17.4 Hz, 1H); LC-MS (M+H⁺) calcd for C22H16ClN3O2 2 389.1, found 390.0.

<Example 5> Preparation of 2-((5,6-dichloro-1H-benzo[d]imidazole-2-yl)(2-hydroxyphenyl)methyl)isoindolin-1-one Step 1: Preparation of N-(2-amino-4,5-dichlorophenyl)-2-(2-methoxyphenyl)-2-(1-oxoisoindole-2-yl)acetamide Crude N-(2-amino-4,5-dichlorophenyl)-2-(2-methoxyphenyl)-2-(1-oxoisoindole-2-yl)acetamide was obtained by performing the same method as in step 1 of Example 1.

Step 2: Preparation of 2-((5,6-dichloro-1H-benzo[d]imidazole-2-yl)(2-methoxyphenyl)methyl)isoindolin-1-one 2-((5,6-Dichloro-1H-benzo[d]imidazole-2-yl)(2-methoxyphenyl)methyl)isoindolin-1-one (44 mg, 2 steps yield 30%) was obtained by performing the same method as in step 2 of Example 1.
¹H NMR (500 MHz, DMSO-d₆) δ 12.92 (s, 1H), 7.89 (s, 1H), 7.75-7.71 (m, 2H), 7.64-7.58 (m, 2H), 7.52 (td, J=7.2, 1.6 Hz, 1H), 7.41 (ddd, J=8.9, 7.2, 2.1 Hz, 1H), 7.13 (dd, J=8.4, 1.0 Hz, 1H), 7.07 (s, 1H), 7.01-6.95 (m, 2H), 4.76 (d, J=17.5 Hz, 1H), 4.02 (d, J=17.5 Hz, 1H), 3.77 (s, 3H).

Step 3: Preparation of 2-((5,6-dichloro-1H-benzo[d]imidazole-2-yl)(2-hydroxyphenyl)methyl)isoindolin-1-one 2-((5,6-Dichloro-1H-benzo[d]imidazole-2-yl)(2-hydroxyphenyl)methyl)isoindolin-1-one (8.7 mg, 60%) was obtained by performing the same method as in step 3 of Example 1.
¹H NMR (500 MHz, methanol-d₄) δ 7.86 (dt, J=7.6, 1.0 Hz, 1H), 7.78 (s, 2H), 7.66 (td, J=7.5, 1.2 Hz, 1H), 7.59-7.54 (m, 2H), 7.34 (ddd, J=8.2, 7.4, 1.7 Hz, 1H), 7.18 (dd, J=7.7, 1.6 Hz, 1H), 7.16 (s, 1H), 6.98-6.93 (m, 2H), 4.79 (d, J=17.4 Hz, 1H), 4.23 (d, J=17.4 Hz, 1H); LC-MS (M+H⁺) calcd for C22H15C12N3O2 423.1, found 424.0.

<Example 6> Preparation of 2-((5-chloro-3H-imidazo[4,5-b]pyridine-2-yl)(2-hydroxyphenyl)methyl)isoindolin-1-one Step 1: Preparation of N-(2-amino-6-chloropyridine-3-yl)-2-(2-methoxyphenyl)-2-(1-oxoisoindole-2-yl)acetamide Crude N-(3-amino-6-chloropyridine-2-yl)-2-(2-methoxyphenyl)-2-(1-oxoisoindole-2-yl)acetamide was obtained by performing the same method as in step 1 of Example 1.

Step 2: Preparation of 2-((5-chloro-3H-imidazo[4,5-b]pyridine-2-yl)(2-methoxyphenyl)methyl)isoindolin-1-one 2-((5-Chloro-3H-imidazo[4,5-b]pyridine-2-yl)(2-methoxyphenyl)methyl)isoindolin-1-one (18 mg, 2 steps yield 13%) was obtained by performing the same method as in step 2 of Example 1.
¹H NMR (500 MHz, DMSO-d₆) δ 8.00 (s, 1H), 7.74 (d, J=7.6 Hz, 1H), 7.66-7.58 (m, 2H), 7.55-7.49 (m, 1H), 7.45-7.40 (m, 1H), 7.30 (d, J=8.3 Hz, 1H), 7.14 (d, J=8.3 Hz, 1H), 7.07 (s, 1H), 7.01 (d, J=7.0 Hz, 1H), 6.97 (t, J=7.4 Hz, 1H), 4.78 (d, J=17.4 Hz, 1H), 4.02 (d, J=17.4 Hz, 1H), 3.78 (s, 3H).

Step 3: Preparation of 2-((5-chloro-3H-imidazo[4,5-b]pyridine-2-yl)(2-hydroxyphenyl)methyl)isoindolin-1-one 2-((5-Chloro-3H-imidazo[4,5-b]pyridine-2-yl)(2-hydroxyphenyl)methyl)isoindolin-1-one (12 mg, 83%) was obtained by performing the same method as in step 3 of Example 1.
¹H NMR (300 MHz, methanol-d₄) δ 7.98 (d, J=8.4 Hz, 1H), 7.85 (dd, J=7.3, 1.5 Hz, 1H), 7.68-7.62 (m, 1H), 7.58-7.51 (m, 2H), 7.39 (d, J=8.4 Hz, 1H), 7.32 (td, J=7.8, 7.1, 1.7 Hz, 1H), 7.18 (s, 1H), 7.12 (dd, J=7.7, 1.6 Hz, 1H), 6.98-6.89 (m, 2H), 4.84 (d, J=17.5 Hz, 1H), 4.19 (d, J=17.5 Hz, 1H); LC-MS (M+H⁺) calcd for C21H15ClN4O2 390.1, found 391.0.

<Example 7> Preparation of 2-((1H-benzo[d]imidazole-2-yl)(5-fluoro-2-hydroxyphenyl)methyl)isoindolin-1-one Step 1: Preparation of N-(2-aminophenyl)-2-(5-fluoro-2-methoxyphenyl)-2-(1-oxoisoindole-2-yl)acetamide Crude N-(2-aminophenyl)-2-(5-fluoro-2-methoxyphenyl)-2-(1-oxoisoindole-2-yl)acetamide was obtained by performing the same method as in step 1 of Example 1.

Step 2: Preparation of 2-((1H-benzo[d]imidazole-2-yl)(5-fluoro-2-methoxyphenyl)methyl)isoindolin-1-one 2-((1H-benzo[d]imidazole-2-yl)(5-fluoro-2-methoxyphenyl)methyl)isoindolin-1-one (106 mg, 2 steps yield 57%) was obtained by performing the same method as in step 2 of Example 1.

$^1$H NMR (500 MHz, DMSO-$d_6$) δ 7.74 (dd, J=7.6, 1.0 Hz, 1H), 7.65-7.57 (m, 3H), 7.52 (td, J=7.2, 1.6 Hz, 1H), 7.45 (dd, J=6.1, 3.5 Hz, 1H), 7.25 (td, J=8.6, 3.2 Hz, 1H), 7.21-7.17 (m, 2H), 7.15 (dd, J=9.1, 4.5 Hz, 1H), 7.07 (s, 1H), 6.91 (dd, J=9.2, 3.1 Hz, 1H), 4.77 (d, J=17.5 Hz, 1H), 4.16 (d, J=17.5 Hz, 1H), 3.77 (s, 3H)

Step 3: Preparation of 2-((1H-benzo[d]imidazole-2-yl)(5-fluoro-2-hydroxyphenyl)methyl)isoindolin-1-one 2-((1H-benzo[d]imidazole-2-yl)(5-fluoro-2-hydroxyphenyl)methyl)isoindolin-1-one (6.4 mg, 33%) was obtained by performing the same method as in step 3 of Example 1.

$^1$H NMR (300 MHz, methanol-$d_4$) δ 7.89 (d, J=7.5 Hz, 1H), 7.71 (ddd, J=9.9, 6.8, 2.2 Hz, 3H), 7.64-7.54 (m, 4H), 7.21-7.13 (m, 3H), 6.99 (dd, J=9.8, 4.6 Hz, 1H), 4.82 (d, J=17.3 Hz, 1H), 4.38 (d, J=17.3 Hz, 1H); LC-MS (M+H$^+$) calcd for C22H16FN3O2 373.1, found 374.1.

<Example 8> Preparation of 2-((1H-benzo[d]imidazole-2-yl)(5-chloro-2-hydroxyphenyl)methyl)isoindolin-1-one Step 1: Preparation of N-(2-aminophenyl)-2-(5-chloro-2-methoxyphenyl)-2-(1-oxoisoindole-2-yl)acetamide Crude N-(2-aminophenyl)-2-(5-chloro-2-methoxyphenyl)-2-(1-oxoisoindole-2-yl)acetamide was obtained by performing the same method as in step 1 of Example 1.

Step 2: Preparation of 2-((1H-benzo[d]imidazole-2-yl)(5-chloro-2-methoxyphenyl)methyl)isoindolin-1-one 2-((1H-benzo[d]imidazole-2-yl)(5-chloro-2-methoxyphenyl)methyl)isoindolin-1-one (78 mg, 2 steps yield 64%) was obtained by performing the same method as in step 2 of Example 1.

$^1$H NMR (500 MHz, chloroform-d) δ 7.75 (d, J=7.6 Hz, 1H), 7.61 (br s, 1H), 7.50 (d, J=3.8 Hz, 2H), 7.44-7.37 (m, 2H), 7.29 (d, J=1.3 Hz, 1H), 7.26 (ddd, J=8.1, 5.5, 2.6 Hz, 3H), 7.18 (s, 1H), 6.71 (d, J=8.7 Hz, 1H), 4.84 (d, J=17.4 Hz, 1H), 4.46 (d, J=17.5 Hz, 1H), 3.52 (s, 2H).

Step 3: Preparation of 2-((1H-benzo[d]imidazole-2-yl)(5-chloro-2-hydroxyphenyl)methyl)isoindolin-1-one 2-((1H-benzo[d]imidazole-2-yl)(5-chloro-2-hydroxyphenyl)methyl)isoindolin-1-one (4.5 mg, 46%) was obtained by performing the same method as in step 3 of Example 1.

$^1$H NMR (500 MHz, methanol-$d_4$) δ 7.90 (d, J=7.6 Hz, 1H), 7.73 (dd, J=6.2, 3.1 Hz, 2H), 7.70 (dd, J=7.5, 1.1 Hz, 1H), 7.64-7.57 (m, 4H), 7.44 (d, J=2.6 Hz, 1H), 7.42 (dd, J=8.6, 2.6 Hz, 1H), 7.16 (s, 1H), 7.00 (d, J=8.6 Hz, 1H), 4.82 (d, J=17.2 Hz, 1H), 4.39 (d, J=17.2 Hz, 1H); LC-MS (M+H$^+$) calcd for C22H16ClN3O2 389.1, found 390.0.

[Reaction Formula e]

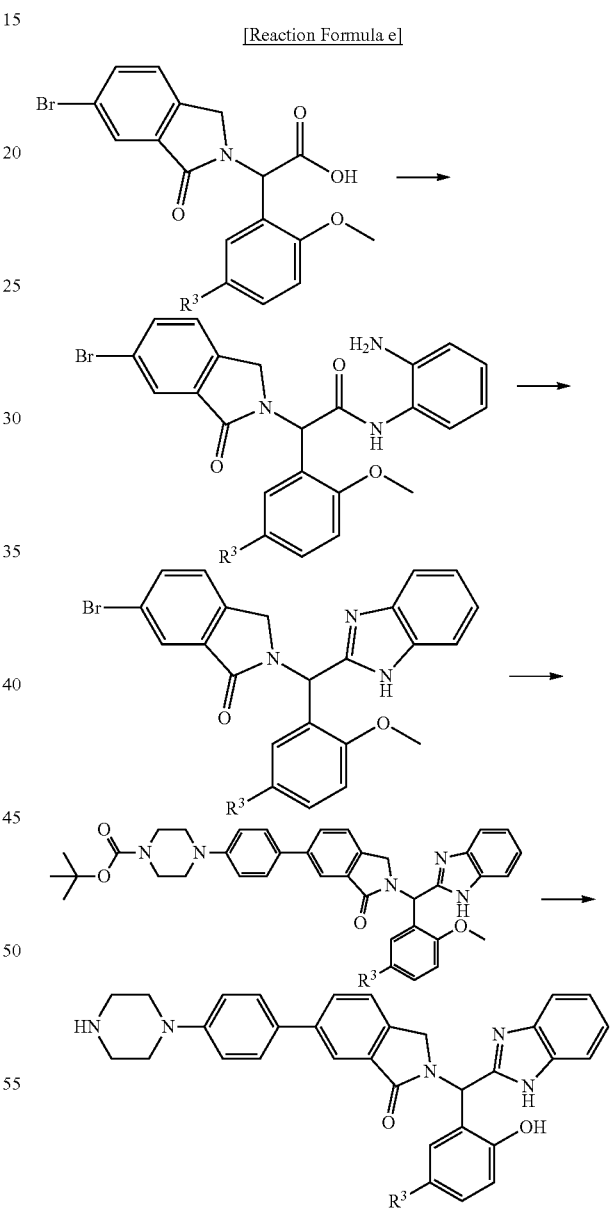

9: $R^3$ = H
10: $R^3$ = F
11: $R^3$ = Cl

According to reaction formula e, the compounds of Examples 9 to 11 were obtained. In reaction formula e, 9 is the compound of Example 9, 10 is the compound of Example 10, and 11 is the compound of Example 11.

<Example 9> Preparation of 2-((1H-benzo[d]imidazole-2-yl)(2-hydroxyphenyl)methyl)-6-(4-(piperazine-1-yl)phenyl)isoindolin-1-one Step 1: Preparation of N-(2-aminophenyl)-2-(6-bromo-1-oxoisoindole-2-yl)-2-(2-methoxyphenyl)acetamide N-(2-aminophenyl)-2-(6-bromo-1-oxoisoindole-2-yl)-2-(2-methoxyphenyl)acetamide was obtained by performing the same method as in step 1 of Example 1.

Step 2: Preparation of 2-((1H-benzo[d]imidazole-2-yl)(2-methoxyphenyl)methyl)-6-bromoisoindolin-1-one 2-((1H-benzo[d]imidazole-2-yl)(2-methoxyphenyl)methyl)-6-bromoisoindolin-1-one (414 mg, 69%) was obtained by performing the same method as in step 2 of Example 1.
$^1$H NMR (500 MHz, DMSO-$d_6$) δ 12.59 (s, 1H), 7.87 (d, J=1.9 Hz, 1H), 7.81 (dd, J=8.0, 2.0 Hz, 1H), 7.59 (d, J=8.1 Hz, 2H), 7.44 (d, J=7.8 Hz, 1H), 7.43-7.38 (m, 1H), 7.22-7.11 (m, 3H), 7.07 (s, 1H), 7.01-6.93 (m, 2H), 4.82 (d, J=17.9 Hz, 1H), 4.00 (d, J=17.9 Hz, 1H), 3.78 (s, 3H).

Step 3: Preparation of tert-butyl 4-(4-(2-((1H-benzo[d]imidazole-2-yl)(2-methoxyphenyl)methyl)-3-oxoisoindole-5-yl)phenyl)piperazine-1-carboxylate Dioxane/water (4/1) solution (0.55 mL) containing 2-((1H-benzo[d]imidazole-2-yl)(2-methoxyphenyl)methyl)-6-bromoisoindolin-1-one (50 mg, 0.11 mmol), commercially available tert-butyl 4-(4-(4,4,5,5-tetramethyl-1,3,2-dioxaborolan-2-yl)phenyl)piperazine-1-carboxylate (43 mg, 0.11 mmol), palladium(II)acetate (1.2 mg, 0.0055 mmol), 2-dicyclohexylphosphino-2',6'-dimethoxybiphenyl (SPhos) (4.5 mg, 0.011 mmol) and cesium carbonate (108 mg, 0.33 mmol) was degassed, and the reaction tube was sealed with a Teflon-lined cap. The reaction mixture was stirred at 110° C. overnight. The mixture was cooled to room temperature and diluted with ethyl acetate. The mixture was washed with water and brine, dried over MgSO$_4$, and concentrated. The residue was purified by silica gel flash column chromatography (n-hexane/EtOAc, 1:1) to give tert-butyl 4-(4-(2-((1H-benzo[d]imidazole-2-yl)(2-methoxyphenyl)methyl)-3-oxoisoindole-5-yl)phenyl)piperazine-1-carboxylate (46 mg, pale yellow solid, yield: 66%).
$^1$H NMR (500 MHz, DMSO-$d_6$) δ 12.59 (s, 1H), 7.87 (d, J=9.0 Hz, 2H), 7.63 (d, J=8.2 Hz, 3H), 7.58 (d, J=7.9 Hz, 1H), 7.46-7.38 (m, 2H), 7.21-7.11 (m, 3H), 7.10 (s, 1H), 7.06 (d, J=8.5 Hz, 2H), 7.02 (d, J=7.4 Hz, 1H), 6.96 (t, J=7.5 Hz, 1H), 4.84 (d, J=17.4 Hz, 1H), 4.03 (d, J=17.5 Hz, 1H), 3.79 (s, 3H), 3.48 (s, 4H), 3.18 (t, J=5.2 Hz, 4H), 1.43 (s, 9H).

Step 4: Preparation of 2-((1H-benzo[d]imidazole-2-yl)(2-hydroxyphenyl)methyl)-6-(4-(piperazine-1-yl)phenyl)isoindolin-1-one 2-((1H-benzo[d]imidazole-2-yl)(2-hydroxyphenyl)methyl)-6-(4-(piperazine-1-yl)phenyl)isoindolin-1-one (6.1 mg, 62%) was obtained by performing the same method as in step 3 of Example 1.

$^1$H NMR (500 MHz, methanol-$d_4$) δ 8.08 (d, J=1.7 Hz, 1H), 7.94 (dd, J=8.0, 1.8 Hz, 1H), 7.74 (dt, J=6.7, 3.4 Hz, 2H), 7.70-7.66 (m, 2H), 7.65 (d, J=8.1 Hz, 1H), 7.61 (dt, J=6.2, 3.3 Hz, 2H), 7.44 (td, J=7.8, 1.7 Hz, 1H), 7.40 (dd, J=7.7, 1.7 Hz, 1H), 7.20 (s, 1H), 7.19-7.16 (m, 2H), 7.06 (dd, J=7.6, 1.1 Hz, 1H), 7.04-7.01 (m, 1H), 4.85 (d, J=17.4 Hz, 1H), 4.35 (d, J=17.4 Hz, 1H), 3.51 (dd, J=6.7, 3.7 Hz, 5H), 3.43 (dd, J=6.6, 3.8 Hz, 5H); LC-MS (M+H$^+$) calcd for C$_{32}$H$_{29}$N$_5$O$_2$ 515.2, found 516.1.

<Example 10> Preparation of 2-((1H-benzo[d]imidazole-2-yl)(5-fluoro-2-hydroxyphenyl)methyl)-6-(4-(piperazine-1-yl)phenyl)isoindolin-1-one Step 1: Preparation of N-(2-aminophenyl)-2-(6-bromo-1-oxoisoindole-2-yl)-2-(5-fluoro-2-methoxyphenyl) acetamide N-(2-aminophenyl)-2-(6-bromo-1-oxoisoindole-2-yl)-2-(5-fluoro-2-methoxyphenyl)acetamide was obtained by performing the same method as in step 1 of Example 1.

Step 2: Preparation of 2-((1H-benzo[d]imidazole-2-yl)(5-fluoro-2-methoxyphenyl)methyl)-6-bromoisoindolin-1-one 2-((1H-benzo[d]imidazole-2-yl)(5-fluoro-2-methoxyphenyl)methyl)-6-bromoisoindolin-1-one was obtained by performing the same method as in step 2 of Example 1.
$^1$H NMR (500 MHz, DMSO-$d_6$) δ 12.64 (s, 1H), 7.87 (d, J=1.9 Hz, 1H), 7.82 (dd, J=8.1, 1.9 Hz, 1H), 7.62-7.58 (m, 2H), 7.47-7.45 (m, 1H), 7.28-7.13 (m, 4H), 7.04 (s, 1H), 6.90 (dd, J=9.1, 3.2 Hz, 1H), 4.75 (d, J=17.9 Hz, 1H), 4.14 (d, J=17.9 Hz, 1H), 3.76 (s, 3H).

Step 3: Preparation of tert-butyl 4-(4-(2-((1H-benzo[d]imidazole-2-yl)(5-fluoro-2-methoxyphenyl)methyl)-3-oxoisoindole-5-yl)phenyl)piperazine-1-carboxylate The same method as in step 3 of Example 9 was performed, but the purification step was omitted due to the solubility to give tert-butyl 4-(4-(2-((1H-benzo[d]imidazole-2-yl)(5-fluoro-2-methoxyphenyl)methyl)-3-oxoisoindole-5-yl)phenyl)piperazine-1-carboxylate. The reaction mixture was extracted with ethyl acetate and water. The residue was triturated with methylene chloride and n-hexane to give tert-butyl 4-(4-(2-((1H-benzo[d]imidazole-2-yl)(5-fluoro-2-methoxyphenyl)methyl)-3-oxoisoindole-5-yl)phenyl)piperazine-1-carboxylate containing impurities.
LC-MS (M+H$^+$) calcd for C38H38ClN5O4 647.3, found 648.1.

Step 4: Preparation of 2-((1H-benzo[d]imidazole-2-yl)(5-fluoro-2-hydroxyphenyl)methyl)-6-(4-(piperazine-1-yl)phenyl)isoindolin-1-one 2-((1H-benzo[d]imidazole-2-yl)(5-fluoro-2-hydroxyphenyl)methyl)-6-(4-(piperazine-1-yl)phenyl)isoindolin-1-one (3.1 mg, 39%) was obtained by performing the same method as in step 3 of Example 1.
$^1$H NMR (500 MHz, methanol-$d_4$) δ 6.53 (s, 1H), 6.40 (d, J=8.0 Hz, 1H), 6.20-6.18 (m, 2H), 6.12 (t, J=7.9 Hz, 3H), 6.06-5.99 (m, 2H), 5.63 (d, J=8.5 Hz, 5H), 5.45 (dd, J=9.8, 4.6 Hz, 1H), 3.30 (d, J=17.5 Hz, 2H), 2.88 (d, J=17.2 Hz, 1H), 1.97 (t, J=5.0 Hz, 4H), 1.88 (t, J=5.1 Hz, 4H); LC-MS (M+H⁺) calcd for C32H28FN5O2 533.2, found 534.1.

<Example 11> Preparation of 2-((1H-benzo[d]imidazole-2-yl)(5-chloro-2-hydroxyphenyl)methyl)-6-(4-(piperazine-1-yl)phenyl)isoindolin-1-one Step 1: Preparation of N-(2-aminophenyl)-2-(6-bromo-1-oxoisoindole-2-yl)-2-(5-chloro-2-methoxyphenyl)acetamide N-(2-aminophenyl)-2-(6-bromo-1-oxoisoindole-2-yl)-2-(5-chloro-2-methoxyphenyl)acetamide was obtained by performing the same method as in step 1 of Example 1.

Step 2: Preparation of 2-((1H-benzo[d]imidazole-2-yl)(5-chloro-2-methoxyphenyl)methyl)-6-bromoisoindolin-1-one 2-((1H-benzo[d]imidazole-2-yl)(5-chloro-2-methoxyphenyl)methyl)-6-bromoisoindolin-1-one was obtained by performing the same method as in step 2 of Example 1.

¹H NMR (500 MHz, DMSO-d₆) δ 12.65 (s, 1H), 7.87 (d, J=1.9 Hz, 1H), 7.81 (dd, J=9.8, 8.0 Hz, 2H), 7.60 (dt, J=12.4, 6.0 Hz, 2H), 7.49-7.45 (m, 2H), 7.36-7.32 (m, 1H), 7.17 (d, J=8.8 Hz, 2H), 7.06 (d, J=2.6 Hz, 1H), 7.04 (s, 1H), 4.78 (d, J=17.8 Hz, 1H), 4.12 (d, J=17.8 Hz, 1H), 3.78 (s, 3H).

Step 3: Preparation of tert-butyl 4-(4-(2-((1H-benzo[d]imidazole-2-yl)(5-chloro-2-methoxyphenyl)methyl)-3-oxoisoindole-5-yl)phenyl)piperazine-1-carboxylate Tert-butyl 4-(4-(2-((1H-benzo[d]imidazole-2-yl)(5-chloro-2-methoxyphenyl)methyl)-3-oxoisoindole-5-yl)phenyl)piperazine-1-carboxylate was obtained by performing the same method as in step 3 of Example 9.
LC-MS (M+H⁺) calcd for C38H38ClN5O4 663.3, found 664.1.

Step 4: Preparation of 2-((1H-benzo[d]imidazole-2-yl)(5-chloro-2-hydroxyphenyl)methyl)-6-(4-(piperazine-1-yl)phenyl)isoindolin-1-one 2-((1H-benzo[d]imidazole-2-yl)(5-chloro-2-hydroxyphenyl)methyl)-6-(4-(piperazine-1-yl)phenyl)isoindolin-1-one (3.5 mg, 22%) was obtained by performing the same method as in step 3 of Example 1.

¹H NMR (500 MHz, methanol-d₄) δ 8.07 (s, 1H), 7.95-7.92 (m, 1H), 7.72 (dd, J=6.3, 3.1 Hz, 2H), 7.67 (t, J=8.3 Hz, 3H), 7.55 (d, J=5.7 Hz, 2H), 7.42-7.37 (m, 2H), 7.18 (s, 2H), 7.16 (s, 1H), 7.00 (d, J=8.6 Hz, 1H), 4.84 (d, J=17.6 Hz, 2H), 4.41 (d, J=17.3 Hz, 1H), 3.51 (t, J=5.1 Hz, 4H), 3.42 (t, J=5.1 Hz, 4H); LC-MS (M−H⁺) calcd for C32H28ClN5O2 549.2, found 548.0.

[Reaction Formula f]

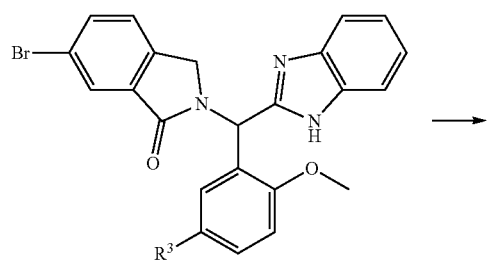

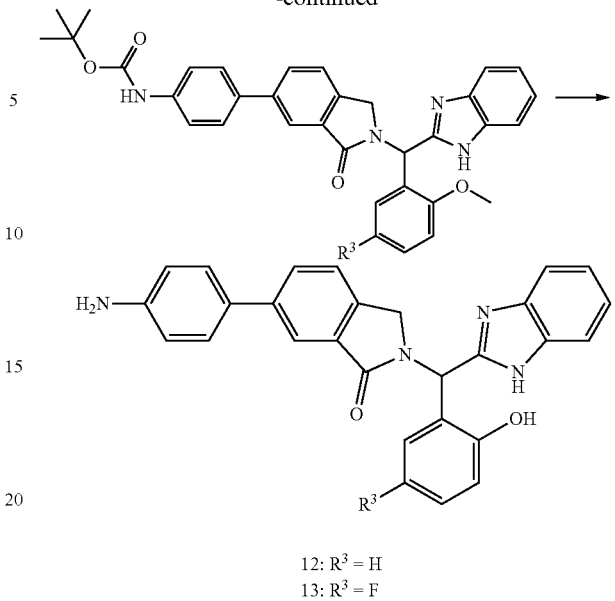

12: R³ = H
13: R³ = F
14: R³ = Cl

According to reaction formula f, the compounds of Examples 12 to 14 were obtained. In reaction formula f, 12 is the compound of Example 12, 13 is the compound of Example 13, and 14 is the compound of Example 14.

<Example 12> Preparation of 2-((1H-benzo[d]imidazole-2-yl)(2-hydroxyphenyl)methyl)-6-(4-aminophenyl)isoindolin-1-one Step 1: Preparation of tert-butyl 4-(2-((1H-benzo[d]imidazole-2-yl)(2-methoxyphenyl)methyl)-3-oxoisoindole-5-yl)phenylcarbamate Tert-butyl 4-(2-((1H-benzo[d]imidazole-2-yl)(2-methoxyphenyl)methyl)-3-oxoisoindole-5-yl)phenylcarbamate (34 mg, 56%) was obtained by performing the same method as in step 3 of Example 9.

¹H NMR (500 MHz, methanol-d₄) δ 8.08 (d, J=1.7 Hz, 1H), 7.95 (dd, J=8.0, 1.8 Hz, 1H), 7.74 (dd, J=6.2, 3.2 Hz, 2H), 7.66-7.59 (m, 6H), 7.56 (d, J=8.6 Hz, 2H), 7.43 (dd, J=7.7, 1.6 Hz, 1H), 7.27 (s, 1H), 7.25 (dd, J=8.4, 1.0 Hz, 1H), 7.16 (td, J=7.5, 1.0 Hz, 1H), 4.75 (d, J=17.3 Hz, 1H), 4.29 (d, J=17.4 Hz, 1H), 3.80 (s, 3H), 1.56 (s, 9H)

Step 2: Preparation of 2-((1H-benzo[d]imidazole-2-yl)(2-hydroxyphenyl)methyl)-6-(4-aminophenyl)isoindolin-1-one 2-((1H-benzo[d]imidazole-2-yl)(2-hydroxyphenyl)methyl)-6-(4-aminophenyl)isoindolin-1-one (2.4 mg, 30%) was obtained by performing the same method as in step 3 of Example 1.

¹H NMR (300 MHz, methanol-d₄) δ 8.14 (d, J=1.7 Hz, 1H), 8.00 (dd, J=8.0, 1.7 Hz, 1H), 7.90-7.83 (m, 2H), 7.73 (td, J=7.6, 7.0, 3.4 Hz, 3H), 7.61 (dd, J=6.3, 3.2 Hz, 2H), 7.48 (d, J=8.5 Hz, 2H), 7.45-7.39 (m, 2H), 7.20 (s, 1H), 7.09-7.00 (m, 2H), 4.85 (s, 1H), 4.38 (d, J=17.6 Hz, 1H); LC-MS (M+H⁺) calcd for C28H22N4O2 446.2, found 447.1.

<Example 13> Preparation of 2-((1H-benzo[d]imidazole-2-yl)(5-fluoro-2-hydroxyphenyl)methyl)-6-(4-aminophenyl)isoindolin-1-one Step 1: Preparation of tert-butyl 4-(2-((1H-benzo[d]imidazole-2-yl)(5-fluoro-2-methoxyphenyl)methyl)-3-oxoisoindole-5-yl)phenylcarbamate Tert-butyl 4-(2-((1H-benzo[d]imidazole-2-yl)(5-fluoro-2-methoxyphenyl)methyl)-3-oxoisoindole-5-yl)phenylcarbamate was obtained by performing the same method as in step 3 of Example 9.
LC-MS (M+H$^+$) calcd for C34H31FN4O4 578.2, found 579.1.

Step 2: Preparation of 2-((1H-benzo[d]imidazole-2-yl)(5-fluoro-2-hydroxyphenyl)methyl)-6-(4-aminophenyl)isoindolin-1-one 2-((1H-benzo[d]imidazole-2-yl)(5-fluoro-2-hydroxyphenyl)methyl)-6-(4-aminophenyl)isoindolin-1-one (2.6 mg, 33%) was obtained by performing the same method as in step 3 of Example 1.
$^1$H NMR (500 MHz, methanol-d$_4$) δ 8.10 (d, J=1.7 Hz, 1H), 7.96 (dd, J=8.0, 1.8 Hz, 1H), 7.77-7.71 (m, 4H), 7.69 (d, J=8.0 Hz, 1H), 7.59-7.54 (m, 2H), 7.29 (d, J=8.5 Hz, 2H), 7.21-7.15 (m, 3H), 7.00 (dd, J=9.9, 4.5 Hz, 1H), 4.86 (d, J=17.5 Hz, 1H), 4.43 (d, J=17.4 Hz, 1H); LC-MS (M+H$^+$) calcd for C28H21FN4O2 464.2, found 465.0.

<Example 14> Preparation of 2-((1H-benzo[d]imidazole-2-yl)(5-chloro-2-hydroxyphenyl)methyl)-6-(4-aminophenyl)isoindolin-1-one Step 1: Preparation of tert-butyl 4-(2-((1H-benzo[d]imidazole-2-yl)(5-chloro-2-methoxyphenyl)methyl)-3-oxoisoindole-5-yl)phenylcarbamate Tert-butyl 4-(2-((1H-benzo[d]imidazole-2-yl)(5-chloro-2-methoxyphenyl)methyl)-3-oxoisoindole-5-yl)phenylcarbamate was obtained by performing the same method as in step 3 of Example 9.
LC-MS (M+H$^+$) calcd for C34H31ClN4O4 594.2, found 595.1.

Step 2: Preparation of 2-((1H-benzo[d]imidazole-2-yl)(5-chloro-2-hydroxyphenyl)methyl)-6-(4-aminophenyl)isoindolin-1-one 2-((1H-benzo[d]imidazole-2-yl)(5-chloro-2-hydroxyphenyl)methyl)-6-(4-aminophenyl)isoindolin-1-one (3.0 mg, 21%) was obtained by performing the same method as in step 3 of Example 1.
$^1$H NMR (500 MHz, methanol-d$_4$) δ 8.08 (s, 1H), 7.95 (d, J=8.3 Hz, 1H), 7.74-7.65 (m, 5H), 7.55 (s, 2H), 7.43-7.35 (m, 2H), 7.22 (d, J=8.2 Hz, 2H), 7.18 (s, 1H), 6.99 (d, J=8.5 Hz, 1H), 4.85 (d, J=17.8 Hz, 1H), 4.41 (d, J=17.4 Hz, 1H); LC-MS (M+H$^+$) calcd for C28H21ClN4O2 480.1, found 481.0

[Reaction Formula g]

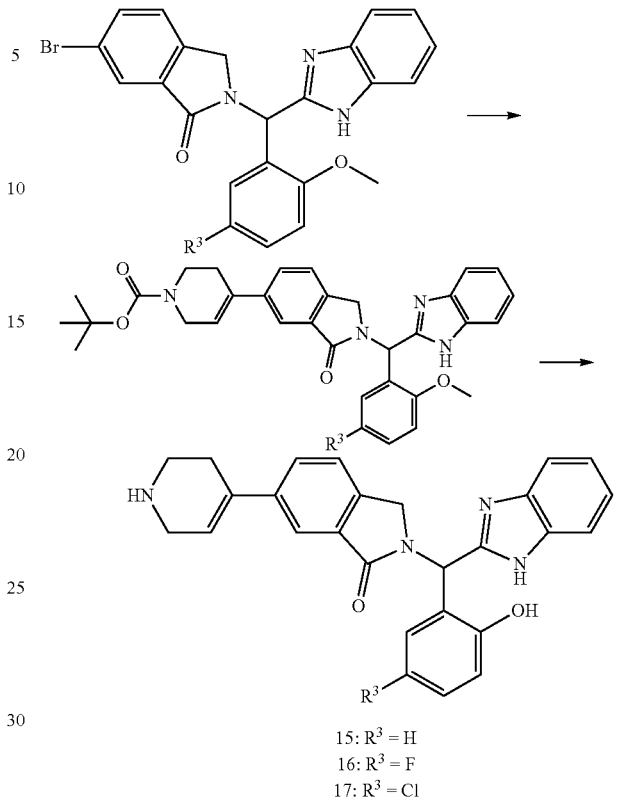

15: R$^3$ = H
16: R$^3$ = F
17: R$^3$ = Cl

According to reaction formula g, the compounds of Examples 15 to 17 were obtained. In reaction formula f, 15 is the compound of Example 15, 16 is the compound of Example 16, and 17 is the compound of Example 17.

<Example 15> Preparation of 2-((1H-benzo[d]imidazole-2-yl)(2-hydroxyphenyl)methyl)-6-(1,2,3,6-tetrahydropyridine-4-yl)isoindolin-1-one Step 1: Preparation of tert-butyl 4-(2-((1H-benzo[d]imidazole-2-yl)(2-methoxyphenyl)methyl)-3-oxoisoindole-5-yl)-5,6-dihydropyridine-1(2H)-carboxylate Tert-butyl 4-(2-((1H-benzo[d]imidazole-2-yl)(2-methoxyphenyl)methyl)-3-oxoisoindole-5-yl)-5,6-dihydropyridine-1(2H)-carboxylate (38 mg, 63%) was obtained by performing the same method as in step 3 of Example 9.
$^1$H NMR (500 MHz, DMSO-d$_6$) δ 12.58 (s, 1H), 7.71 (d, J=7.8 Hz, 2H), 7.57 (t, J=6.6 Hz, 2H), 7.43 (d, J=7.8 Hz, 1H), 7.40 (t, J=8.2 Hz, 1H), 7.16 (dq, J=23.4, 8.5, 7.9 Hz, 3H), 7.08 (s, 1H), 7.00 (d, J=7.4 Hz, 1H), 6.95 (t, J=7.5 Hz, 1H), 6.27 (s, 1H), 4.81 (d, J=17.6 Hz, 1H), 4.00 (d, J=18.5 Hz, 3H), 3.78 (s, 3H), 3.56 (s, 2H), 1.44 (s, 9H)

Step 2: Preparation of 2-((1H-benzo[d]imidazole-2-yl)(2-hydroxyphenyl)methyl)-6-(1,2,3,6-tetrahydropyridine-4-yl)isoindolin-1-one 2-((1H-benzo[d]imidazole-2-yl)(2-hydroxyphenyl)methyl)-6-(1,2,3,6-tetrahydropyridine-4-yl)isoindolin-1-one (5.6 mg, 64%) was obtained by performing the same method as in step 3 of Example 1.

¹H NMR (300 MHz, methanol-d₄) δ 7.95 (d, J=1.6 Hz, 1H), 7.82 (dd, 7=8.1, 1.7 Hz, 1H), 7.69 (dd, J=6.2, 3.2 Hz, 2H), 7.61 (d, J=8.0 Hz, 1H), 7.52 (dt, J=6.4, 3.6 Hz, 2H), 7.39 (td, J=7.8, 1.6 Hz, 1H), 7.28 (dd, J=8.0, 1.7 Hz, 1H), 7.18 (s, 1H), 6.99 (dt, J=7.4, 3.2 Hz, 2H), 6.30 (s, 1H), 4.82 (d, J=17.7 Hz, 1H), 4.29 (d, J=17.7 Hz, 1H), 3.91 (q, J=2.6 Hz, 2H), 3.53 (t, J=6.1 Hz, 2H), 2.91 (d, J=6.6 Hz, 2H); LC-MS (M+H⁺) calcd for $C_{27}H_{24}N_4O_2$ 436.2 found 437.1.

<Example 16> Preparation of 2-((1H-benzo[d]imidazole-2-yl)(5-fluoro-2-methoxyphenyl)methyl)-6-(1,2,3,6-tetrahydropyridine-4-yl)isoindolin-1-one Step 1: Preparation of tert-butyl 4-(2-((1H-benzo[d]imidazole-2-yl)(5-fluoro-2-methoxyphenyl)methyl)-3-oxoisoindole-5-yl)-5,6-dihydropyridine-1(2H)-carboxylate Tert-butyl 4-(2-((1H-benzo[d]imidazole-2-yl)(5-fluoro-2-methoxyphenyl)methyl)-3-oxoisoindole-5-yl)-5,6-dihydropyridine-1(2H)-carboxylate was obtained by performing the same method as in step 3 of Example 9.
LC-MS (M+H⁺) calcd for C33H33FN4O4 568.3 found 569.1.

Step 2: Preparation of 2-((1H-benzo[d]imidazole-2-yl)(5-fluoro-2-methoxyphenyl)methyl)-6-(1,2,3,6-tetrahydropyridine-4-yl)isoindolin-1-one 2-((1H-benzo[d]imidazole-2-yl)(5-fluoro-2-methoxyphenyl)methyl)-6-(1,2,3,6-tetrahydropyridine-4-yl)isoindolin-1-one (3.6 mg, 44%) was obtained by performing the same method as in step 3 of Example 1.
¹H NMR (500 MHz, methanol-d₄) δ 7.96 (d, J=1.6 Hz, 1H), 7.84 (dd, J=8.0, 1.7 Hz, 1H), 7.71 (dt, J=7.1, 3.5 Hz, 2H), 7.64 (d, J=8.1 Hz, 1H), 7.55 (dt, J=6.2, 3.6 Hz, 2H), 7.19-7.14 (m, 2H), 7.12 (dd, J=8.8, 3.1 Hz, 1H), 6.98 (dd, J=8.9, 4.5 Hz, 1H), 6.31 (mf, 1H), 4.83 (d, J=17.5 Hz, 1H), 4.39 (d, J=17.6 Hz, 1H), 3.92 (d, J=3.2 Hz, 2H), 3.53 (t, J=6.1 Hz, 2H), 2.90 (s, 2H); LC-MS (M–H⁺) calcd for C27H23FN4O2 454.2 found 453.1.

<Example 17> Preparation of 2-((1H-benzo[d]imidazole-2-yl)(5-chloro-2-methoxyphenyl)methyl)-6-(1,2,3,6-tetrahydropyridine-4-yl)isoindolin-1-one Step 1: Preparation of tert-butyl 4-(2-((1H-benzo[d]imidazole-2-yl)(5-chloro-2-methoxyphenyl)methyl)-3-oxoisoindole-5-yl)-5,6-dihydropyridine-1(2H)-carboxylate Tert-butyl 4-(2-((1H-benzo[d]imidazole-2-yl)(5-chloro-2-methoxyphenyl)methyl)-3-oxoisoindole-5-yl)-5,6-dihydropyridine-1(2H)-carboxylate was obtained by performing the same method as in step 3 of Example 9.
LC-MS (M+H⁺) calcd for C33H33ClN4O4 584.2 found 585.0.

Step 2: Preparation of 2-((1H-benzo[d]imidazole-2-yl)(5-chloro-2-methoxyphenyl)methyl)-6-(1,2,3,6-tetrahydropyridine-4-yl)isoindolin-1-one 2-((1H-benzo[d]imidazole-2-yl)(5-chloro-2-methoxyphenyl)methyl)-6-(1,2,3,6-tetrahydropyridine-4-yl)isoindolin-1-one (3.1 mg, 22%) was obtained by performing the same method as in step 3 of Example 1.
¹H NMR (500 MHz, methanol-d₄) δ 7.95 (s, 1H), 7.83 (d, J=8.0 Hz, 1H), 7.69 (s, 2H), 7.63 (d, J=8.1 Hz, 1H), 7.51 (s, 2H), 7.38 (d, J=8.7 Hz, 1H), 7.31 (s, 1H), 7.16 (s, 1H), 6.98 (d, J=8.7 Hz, 1H), 6.31 (s, 1H), 4.82 (d, J=17.8 Hz, 1H), 4.38 (d, J=17.5 Hz, 1H), 3.92 (s, 2H), 3.53 (t, J=6.1 Hz, 2H), 2.90 (s, 2H); LC-MS (M+H⁺) calcd for C27H23ClN4O2 470.2 found 471.0.

<Example 18> Preparation of 2-((1H-benzo[d]imidazole-2-yl)(5-fluoro-2-hydroxyphenyl)methyl)-6-(4-(4-methylpiperazine-1-yl)phenyl)isoindolin-1-one

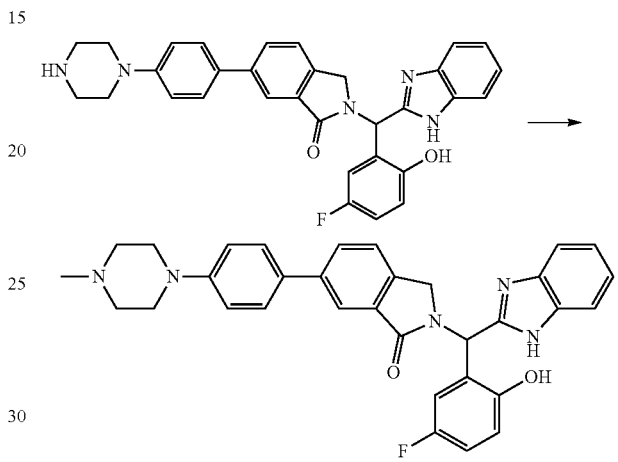

Water (0.2 mL) containing 37% formaldehyde was added to methanol (0.25 mL) containing 2-((1H-benzo[d]imidazole-2-yl)(5-fluoro-2-hydroxyphenyl)methyl)-6-(4-(piperazine-1-yl)phenyl)isoindolin-1-one (30 mg, 0.06 mmol) of Example 10 and acetic acid (70 μL, 0.072 mmol). The reaction mixture was stirred at room temperature for 1 hour. The suspension was cooled to 0° C. in an ice bath, to which a small amount of sodium cyanoborohydride was added. The reaction mixture was stirred at room temperature for 18 hours, then quenched with ammonium chloride, and extracted with methylene chloride. The combined organic layer was dried over MgSO₄, filtered, and evaporated to give 2-((1H-benzo[d]imidazole-2-yl)(5-fluoro-2-hydroxyphenyl)methyl)-6-(4-(4-methylpiperazine-1-yl)phenyl)isoindolin-1-one (2.7 mg, white solid, yield: 8.2%).
LC-MS (M+H⁺) calcd for C33H30FN5O2 547.2 found 548.1.

[Reaction Formula h]

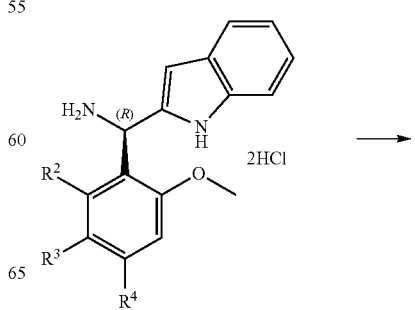

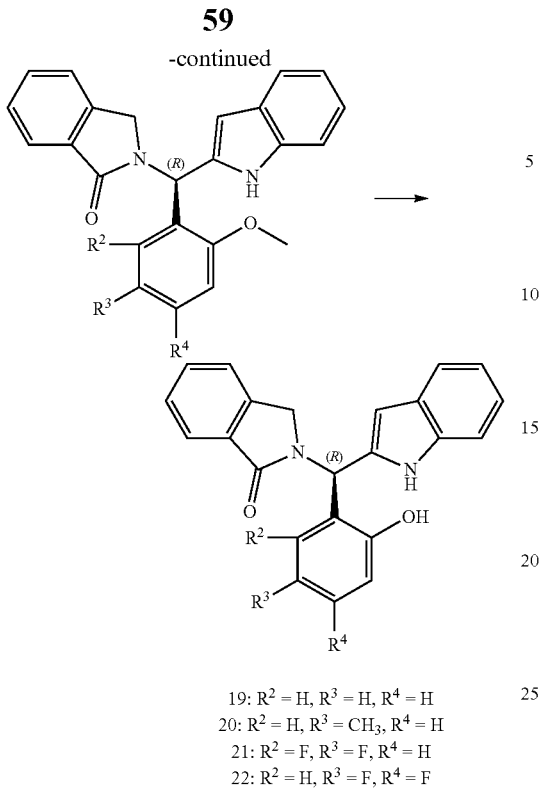

19: $R^2 = H, R^3 = H, R^4 = H$
20: $R^2 = H, R^3 = CH_3, R^4 = H$
21: $R^2 = F, R^3 = F, R^4 = H$
22: $R^2 = H, R^3 = F, R^4 = F$

According to reaction formula h, the compounds of Examples 19 to 22 were obtained. In reaction formula f, 19 is the compound of Example 19, 20 is the compound of Example 20, 21 is the compound of Example 21, and 22 is the compound of Example 22.

<Example 19> Preparation of (R)-2-((2-hydroxyphenyl)(1H-indole-2-yl)methyl)isoindolin-1-one Step 1: Preparation of (R)-2-((1H-indole-2-yl)(2-methoxyphenyl)methyl)isoindolin-1-one N,N-diisopropylethylamine (0.17 mL, 1 mmol) was added to tetrahydrofuran (1 mL) containing (R)-(1H-indole-2-yl)(2-methoxyphenyl)methaneamine (50 mg, 0.20 mmol) and methyl-2-bromomethylbenzoate (55 mg, 0.24 mmol), followed by stirring at 80° C. overnight. The mixture was extracted with ethyl acetate and water. The ethyl acetate layers were combined, dried over anhydrous magnesium sulfate, and filtered. The solvent was removed using an evaporator under reduced pressure. The residue was purified by silica gel flash column chromatography (CH$_2$Cl$_2$/EtOAc, 1:0 to 1:1) to give (R)-2-((1H-indole-2-yl)(2-methoxyphenyl)methyl)isoindolin-1-one (59 mg, white solid, yield: 80%).

$^1$H NMR (500 MHz, chloroform-d) δ 7.84 (d, J=7.6 Hz, 1H), 7.55 (d, J=7.8 Hz, 1H), 7.51 (td, J=7.5, 1.2 Hz, 1H), 7.44 (t, J=7.5 Hz, 1H), 7.40-7.34 (m, 4H), 7.18 (ddd, J=8.1, 7.0, 1.2 Hz, 1H), 7.13-7.08 (m, 2H), 7.01-6.94 (m, 2H), 6.34-6.30 (m, 1H), 4.49 (d, J=17.3 Hz, 1H), 4.32 (d, J=17.3 Hz, 1H), 3.80 (s, 3H).

Step 2: Preparation of (R)-2-((2-hydroxyphenyl)(1H-indole-2-yl)methyl)isoindolin-1-one (R)-2-((2-hydroxyphenyl)(1H-indole-2-yl)methyl)isoindolin-1-one (8 mg, 9%) was obtained by performing the same method as in step 3 of Example 1.

$^1$H NMR (500 MHz, DMSO-d6) δ 11.18 (s, 1H), 9.73 (s, 1H), 7.73 (d, J=7.5 Hz, 1H), 7.63-7.55 (m, 2H), 7.51 (t, J=7.3 Hz, 1H), 7.44 (d, J=7.8 Hz, 1H), 7.29 (d, J=8.1 Hz, 1H), 7.19 (td, J=7.7, 1.8 Hz, 1H), 7.07-7.02 (m, 1H), 7.01-6.93 (m, 3H), 6.89 (dd, J=8.1, 1.2 Hz, 1H), 6.80 (t, J=7.5 Hz, 1H), 6.09 (t, J=1.3 Hz, 1H), 4.38 (d, J=17.8 Hz, 1H), 4.19 (d, J=17.8 Hz, 1H).

<Example 20> Preparation of (R)-2-((2-hydroxy-5-methylphenyl)(1H-indole-2-yl)methyl)isoindolin-1-one Step 1: Preparation of (R)-2-((1H-indole-2-yl)(2-methoxy-5-methylphenyl)methyl)isoindolin-1-one (R)-2-((1H-indole-2-yl)(2-methoxy-5-methylphenyl)methyl)isoindolin-1-one (23 mg, 75%) was obtained by performing the same method as in step 1 of Example 19.

$^1$H NMR (300 MHz, chloroform-d) δ 9.21 (s, 1H), 7.81 (d, J=7.7 Hz, 1H), 7.55 (t, J=7.6 Hz, 1H), 7.48 (dd, J=7.4, 1.3 Hz, 1H), 7.45-7.40 (m, 1H), 7.39-7.33 (m, 2H), 7.21-7.12 (m, 3H), 7.11-7.07 (m, 2H), 6.89-6.80 (m, 1H), 6.35-6.27 (m, 1H), 4.47 (d, J=17.4 Hz, 1H), 4.33 (d, J=17.3 Hz, 1H), 3.75 (s, 3H), 2.29 (s, 3H).

Step 2: Preparation of (R)-2-((2-hydroxy-5-methylphenyl)(1H-indole-2-yl)methyl)isoindolin-1-one (R)-2-((2-hydroxy-5-methylphenyl)(1H-indole-2-yl)methyl)isoindolin-1-one (7 mg, 73%) was obtained by performing the same method as in step 3 of Example 1.

$^1$H NMR (300 MHz, methanol-d4) δ 7.84 (d, J=7.6 Hz, 1H), 7.65-7.58 (m, 1H), 7.57-7.51 (m, 2H), 7.46 (d, J=7.7 Hz, 1H), 7.35-7.29 (m, 1H), 7.14-6.95 (m, 4H), 6.88 (s, 1H), 6.78 (d, J=8.1 Hz, 1H), 6.17 (s, 1H), 4.54 (d, J=17.9 Hz, 1H), 4.22 (d, J=18.0 Hz, 1H); LC-MS (M+H$^+$) calcd for C$_{24}$H$_{20}$N$_2$O$_2$, 368.4 found 367.1.

<Example 21> Preparation of (R)-2-((2,3-difluoro-6-hydroxyphenyl)(1H-indole-2-yl)methyl)isoindolin-1-one Step 1: Preparation of (R)-2-((2,3-difluoro-6-methoxyphenyl)(1H-indole-2-yl)methyl)isoindolin-1-one ((R)-2-((2,3-difluoro-6-methoxyphenyl)(1H-indole-2-yl)methyl)isoindolin-1-one (18 mg, 62%) was obtained by performing the same method as in step 1 of Example 19.

LC-MS (M−H$^+$) calcd for C24H18F2N2O2 404.1 found 403.0.

Step 2: Preparation of (R)-2-((2,3-difluoro-6-hydroxyphenyl)(1H-indole-2-yl)methyl)isoindolin-1-one (R)-2-((2,3-difluoro-6-hydroxyphenyl)(1H-indole-2-yl)methyl)isoindolin-1-one (9 mg, 58%) was obtained by performing the same method as in step 3 of Example 1.

$^1$H NMR (300 MHz, methanol-d4) δ 7.84-7.79 (m, 1H), 7.65-7.58 (m, 1H), 7.55-7.45 (m, 3H), 7.34 (d, J=8.1 Hz, 1H), 7.26 (s, 1H), 7.16-7.05 (m, 2H), 7.03-6.96 (m, 1H), 6.68 (ddd, J=9.2, 4.0, 1.9 Hz, 1H), 6.21 (s, 1H), 4.65 (d, J=17.9 Hz, 1H), 4.46 (d, J=17.9 Hz, 1H); LC-MS (M−H$^+$) calcd for C23H16F2N2O2, 390 found 389.0.

<Example 22> Preparation of (R)-2-((4,5-difluoro-2-hydroxyphenyl)(1H-indole-2-yl)methyl)isoindolin-1-one Step 1: Preparation of (R)-2-((4,5-difluoro-2-methoxyphenyl)(1H-indole-2-yl)methyl)isoindolin-1-one (R)-2-((4,5-difluoro-2-methoxyphenyl)(1H-indole-2-yl)methyl)isoindolin-1-one (18 mg, 62%) was obtained by performing the same method as in step 1 of Example 19.
LC-MS (M−H+) calcd for C24H18F2N2O2 404.1 found 403.0.

Step 2: Preparation of (R)-2-((4,5-difluoro-2-hydroxyphenyl)(1H-indole-2-yl)methyl)isoindolin-1-one (R)-2-((4,5-difluoro-2-hydroxyphenyl)(1H-indole-2-yl)methyl)isoindolin-1-one (10 mg, 64%) was obtained by performing the same method as in step 3 of Example 1.
$^1$H NMR (500 MHz, methanol-d4) δ 7.84 (dt, J=7.5, 1.0 Hz, 1H), 7.64 (td, J=7.5, 1.2 Hz, 1H), 7.58-7.54 (m, 2H), 7.51-7.47 (m, 1H), 7.33 (dd, J=8.2, 1.0 Hz, 1H), 7.10 (ddd, J=8.1, 7.0, 1.1 Hz, 1H), 7.04 (s, 1H), 7.01 (ddd, J=8.0, 7.0, 1.0 Hz, 1H), 6.94 (dd, J=11.4, 9.0 Hz, 1H), 6.77 (dd, J=11.8, 6.8 Hz, 1H), 6.21-6.19 (m, 1H), 4.53 (d, J=17.8 Hz, 1H), 4.29 (d, J=17.8 Hz, 1H); LC-MS (M−H+) calcd for C23H16F2N2O2, 390 found 389.0.

<Example 23> Preparation of (R)-2-((5-fluoro-2-hydroxyphenyl)(1H-indole-2-yl)methyl)isoindolin-1-one Step 1: Preparation of (R)-2-((5-fluoro-2-methoxyphenyl)(1H-indole-2-yl)methyl)isoindolin-1-one (R)-2-((5-fluoro-2-methoxyphenyl)(1H-indole-2-yl)methyl)isoindolin-1-one (35 mg, 56%) was obtained by performing the same method as in step 1 of Example 19.
$^1$H NMR (300 MHz, chloroform-d) δ 10.16 (s, 1H), 7.59 (dd, J=11.4, 7.6 Hz, 2H), 7.44-7.36 (m, 2H), 7.30-7.16 (m, 3H), 7.13 (d, J=8.3 Hz, 2H), 7.02 (dd, J=8.6, 2.2 Hz, 2H), 6.88-6.80 (m, 1H), 6.24 (d, J=2.0 Hz, 1H), 4.39 (d, J=17.5 Hz, 1H), 4.24 (d, J=17.5 Hz, 1H), 3.66 (s, 3H).

Step 2: Preparation of (R)-2-((5-fluoro-2-hydroxyphenyl)(1H-indole-2-yl)methyl)isoindolin-1-one (R)-2-((5-fluoro-2-hydroxyphenyl)(1H-indole-2-yl)methyl)isoindolin-1-one (2.6 mg, 27%) was obtained by performing the same method as in step 3 of Example 1.
$^1$H NMR (300 MHz, methanol-d$_4$) δ 7.84 (d, J=7.6 Hz, 1H), 7.66-7.59 (m, 1H), 7.57-7.45 (m, 3H), 7.33 (d, J=8.1 Hz, 1H), 7.09 (d, J=4.2 Hz, 2H), 7.03-6.93 (m, 2H), 6.86 (dd, J=8.8, 4.7 Hz, 1H), 6.78 (dd, J=9.4, 3.0 Hz, 1H), 6.22-6.17 (m, 1H), 4.52 (d, J=17.8 Hz, 1H), 4.28 (d, J=17.9 Hz, 1H).

<Example 24> Preparation of (S)-2-((5-fluoro-2-hydroxyphenyl)(1H-indole-2-yl)methyl)isoindolin-1-one Step 1: Preparation of (S)-2-((5-fluoro-2-methoxyphenyl)(1H-indole-2-yl)methyl)isoindolin-1-one (S)-2-((5-fluoro-2-methoxyphenyl)(1H-indole-2-yl)methyl)isoindolin-1-one (52 mg, 48%) was obtained by performing the same method as in step 1 of Example 19.
$^1$H NMR (300 MHz, chloroform-d) δ 10.16 (s, 1H), 7.59 (dd, J=11.4, 7.6 Hz, 2H), 7.44-7.36 (m, 2H), 7.30-7.16 (m, 3H), 7.13 (d, J=8.3 Hz, 2H), 7.02 (dd, J=8.6, 2.2 Hz, 2H), 6.88-6.80 (m, 1H), 6.24 (d, J=2.0 Hz, 1H), 4.39 (d, J=17.5 Hz, 1H), 4.24 (d, J=17.5 Hz, 1H), 3.66 (s, 3H).

Step 2: Preparation of (S)-2-((5-fluoro-2-hydroxyphenyl)(1H-indole-2-yl)methyl)isoindolin-1-one (S)-2-((5-fluoro-2-hydroxyphenyl)(1H-indole-2-yl)methyl)isoindolin-1-one (84.6 mg, 35%) was obtained by performing the same method as in step 3 of Example 1.
$^1$H NMR (300 MHz, methanol-d$_4$) δ 7.84 (d, J=7.6 Hz, 1H), 7.66-7.59 (m, 1H), 7.57-7.45 (m, 3H), 7.33 (d, J=8.1 Hz, 1H), 7.09 (d, J=4.2 Hz, 2H), 7.03-6.93 (m, 2H), 6.86 (dd, J=8.8, 4.7 Hz, 1H), 6.78 (dd, J=9.4, 3.0 Hz, 1H), 6.22-6.17 (m, 1H), 4.52 (d, J=17.8 Hz, 1H), 4.28 (d, J=17.9 Hz, 1H).

<Example 25> Preparation of (R)-2-((2-fluoro-6-hydroxyphenyl)(1H-indole-2-yl)methyl)isoindolin-1-one Step 1: Preparation of (R)-2-((5-chloro-2-methoxyphenyl)(1H-indole-2-yl)methyl)isoindolin-1-one (R)-2-((5-chloro-2-methoxyphenyl)(1H-indole-2-yl)methyl)isoindolin-1-one (34 mg, 56%) was obtained by performing the same method as in step 1 of Example 19.
$^1$H NMR (300 MHz, chloroform-d) δ 10.19 (s, 1H), 7.57 (d, J=6.9 Hz, 2H), 7.51-7.46 (m, 1H), 7.44-7.39 (m, 1H), 7.37-7.26 (m, 2H), 7.23-7.07 (m, 4H), 6.80 (dd, J=10.3, 8.5 Hz, 1H), 6.73 (d, J=8.4 Hz, 1H), 6.35 (s, 1H), 4.52 (d, J=17.6 Hz, 1H), 4.30 (d, J=17.6 Hz, 1H), 3.67 (s, 3H).

Step 2: Preparation of (R)-2-((2-fluoro-6-hydroxyphenyl)(1H-indole-2-yl)methyl)isoindolin-1-one (R)-2-((5-chloro-2-hydroxyphenyl)(1H-indole-2-yl)methyl)isoindolin-1-one (2.9 mg, 30%) was obtained by performing the same method as in step 3 of Example 1.
$^1$H NMR (300 MHz, DMSO-d$_6$) δ 11.33 (s, 1H), 10.32 (d, J=1.6 Hz, 1H), 7.74 (d, J=7.5 Hz, 1H), 7.63 (d, J=4.2 Hz, 2H), 7.52 (dt, J=8.1, 4.2 Hz, 1H), 7.40-7.30 (m, 2H), 7.23 (q, J=8.0 Hz, 1H), 7.13 (q, J=8.3, 7.6 Hz, 3H), 6.73 (d, J=8.3 Hz, 1H), 6.71-6.62 (m, 1H), 4.68 (d, J=17.4 Hz, 1H), 4.24 (d, J=17.3 Hz, 1H).

<Example 26> Preparation of (R)-2-((5-chloro-2-hydroxyphenyl)(1H-indole-2-yl)methyl)isoindolin-1-one Step 1: Preparation of (R)-2-((2-fluoro-6-methoxyphenyl)(1H-indole-2-yl)methyl)isoindolin-1-one (R)-2-((2-fluoro-6-methoxyphenyl)(1H-indole-2-yl)methyl)isoindolin-1-one (46 mg, 65%) was obtained by performing the same method as in step 1 of Example 19.
$^1$H NMR (300 MHz, chloroform-d) δ 10.38 (s, 1H), 7.61-7.53 (m, 2H), 7.39 (ddd, J=16.0, 7.7, 1.1 Hz, 2H), 7.34-7.27 (m, 1H), 7.27-7.09 (m, 6H), 6.82 (d, J=8.8 Hz, 1H), 6.21 (dt, J=2.0, 0.9 Hz, 1H), 4.39 (d, J=17.5 Hz, 1H), 4.19 (d, J=17.6 Hz, 1H), 3.63 (s, 3H).

Step 2: Preparation of (R)-2-((5-chloro-2-hydroxyphenyl)(1H-indole-2-yl)methyl)isoindolin-1-one (R)-2-((5-chloro-2-hydroxyphenyl)(1H-indole-2-yl)methyl)isoindolin-1-one (4.4 mg, 23%) was obtained by performing the same method as in step 3 of Example 1.

¹H NMR (300 MHz, methanol-d₄) δ 7.87-7.81 (m, 1H), 7.67-7.59 (m, 1H), 7.57-7.46 (m, 3H), 7.37-7.31 (m, 1H), 7.21 (dd, J=8.6, 2.6 Hz, 1H), 7.13-7.05 (m, 2H), 7.05-6.97 (m, 2H), 6.87 (d, J=8.6 Hz, 1H), 6.19 (d, J=1.4 Hz, 1H), 4.52 (d, J=17.9 Hz, 1H), 4.26 (d, J=17.9 Hz, 1H).

<Example 27> Preparation of (S)-2-((5-fluoro-2-hydroxyphenyl)(1H-pyrrolo[2,3-b]pyridine-2-yl)methyl)isoindolin-1-one Step 1: Preparation of (S)-2-((5-fluoro-2-methoxyphenyl)(1H-pyrrolo[2,3-b]pyridine-2-yl)methyl)isoindolin-1-one (S)-2-((5-fluoro-2-methoxyphenyl)(1H-pyrrolo[2,3-b]pyridine-2-yl)methyl)isoindolin-1-one (48 mg, 80%) was obtained by performing the same method as in step 1 of Example 19.
¹H NMR (300 MHz, chloroform-d) δ 12.05 (s, 1H), 7.94 (dd, J=4.9, 1.5 Hz, 1H), 7.91-7.87 (m, 1H), 7.79 (dd, J=7.8, 1.5 Hz, 1H), 7.55-7.41 (m, 2H), 7.34 (d, J=7.4 Hz, 1H), 7.28 (d, J=1.5 Hz, 1H), 7.08-6.88 (m, 4H), 6.18 (t, J=1.4 Hz, 1H), 4.39 (d, J=17.2 Hz, 1H), 4.28 (d, J=17.2 Hz, 1H).

Step 2: Preparation of (S)-2-((5-fluoro-2-hydroxyphenyl)(1H-pyrrolo[2,3-b]pyridine-2-yl)methyl)isoindolin-1-one (S)-2-((5-fluoro-2-hydroxyphenyl)(1H-pyrrolo[2,3-b]pyridine-2-yl)methyl)isoindolin-1-one (5.4 mg, 25%) was obtained by performing the same method as in step 3 of Example 1.
¹H NMR (500 MHz, methanol-d₄) δ 8.47 (dt, J=8.7, 2.1 Hz, 1H), 8.33 (d, J=5.7 Hz, 1H), 7.85 (d, J=7.6 Hz, 1H), 7.66 (td, J=7.5, 1.1 Hz, 1H), 7.60-7.55 (m, 2H), 7.50-7.46 (m, 1H), 7.13 (s, 1H), 7.04 (td, J=8.5, 3.1 Hz, 1H), 6.92 (dd, J=8.9, 4.5 Hz, 1H), 6.80 (dd, J=9.1, 3.1 Hz, 1H), 6.61 (t, 7=1.1 Hz, 1H), 4.62 (d, J=17.6 Hz, 1H), 4.28 (d, J=17.6 Hz, 1H).

[Reaction Formula i]

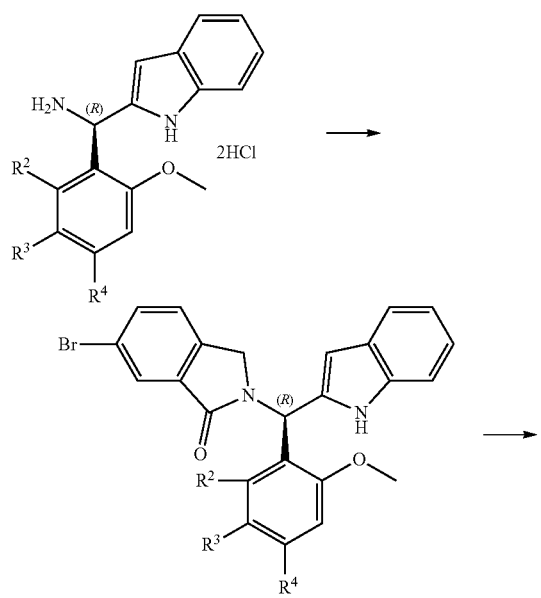

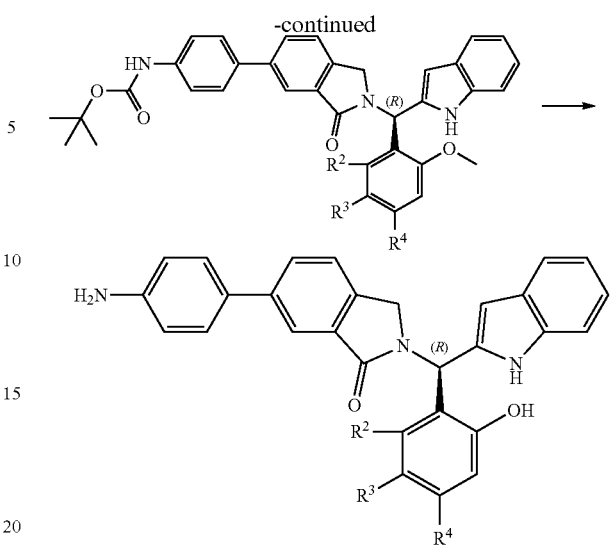

28: R² = H, R³ = H, R⁴ = H,
29: R² = H, R³ = F, R⁴ = H
30: R² = H, R³ = Cl, R⁴ = H

According to reaction formula i, the compounds of Examples 28 to 30 were obtained. In reaction formula i, 28 is the compound of Example 28, 29 is the compound of Example 29, and 30 is the compound of Example 30.

<Example 28> Preparation of (R)-6-(4-aminophenyl)-2-((2-hydroxyphenyl)(1H-indole-2-yl)methyl)isoindolin-1-one Step 1: Preparation of (R)-2-((1H-indole-2-yl)(2-methoxyphenyl)methyl)-6-bromoisoindolin-1-one N,N-diisopropylethylamine (4 mL, 19.8 mmol) was added to tetrahydrofuran solution (20 mL) containing (R)-(1H-indole-2-yl)(2-methoxyphenyl)methaneamine (1 g, 3.96 mmol) and methyl 5-bromo-2-(bromomethyl)benzoate (1.6 g, 5.14 mmol), followed by stirring at 80° C. overnight. The mixture was extracted with ethyl acetate and water. The ethyl acetate layers were combined, dried over anhydrous magnesium sulfate, and filtered. The solvent was removed using an evaporator under reduced pressure. The residue was purified by silica gel flash column chromatography (CH₂Cl₂/EtOAc, 1:0 to 1:1) to give (R)-2-((1H-indole-2-yl)(2-methoxyphenyl)methyl)-6-bromoisoindolin-1-one (1.1 mg, green solid, yield: 62%).
¹H NMR (300 MHz, methanol-d₄) δ 7.97-7.89 (m, 1H), 7.74 (dd, J=8.1, 1.8 Hz, 1H), 7.48-7.36 (m, 3H), 7.35-7.26 (m, 1H), 7.09 (ddd, J=15.2, 7.0, 2.4 Hz, 5H), 7.03-6.93 (m, 2H), 6.13 (d, J=1.1 Hz, 1H), 4.43 (d, J=18.2 Hz, 1H), 4.18 (d, J=18.3 Hz, 1H), 3.80 (s, 3H).

Step 2: Preparation of tert-butyl (R)-(4-(2-((1H-indole-2-yl)(2-methoxyphenyl)methyl)-3-oxoisoindole-5-yl)phenyl)carbamate 4-Tert-butoxycarbonylaminophenylboronic acid (64 mg, 0.201 mmol), (R)-2-((1H-indole-2-yl)(2-methoxyphenyl)methyl)-6-bromoisoindolin-1-one (30 mg, 0.067 mmol), Pd(OAc)₂ (0.7 mg, 0.003 mmol), Sphos (2.5 mg, 0.006 mmol) and sodium carbonate (21.3 mg, 0.201 mmol) were degassed in 1,4-dioxane/H₂O (0.268/0.067 mL) for 10 minutes, followed by stirring at 100° C. overnight. The reaction mixture was diluted with ethyl acetate and washed with water and brine. The organic layer was dried over anhydrous magnesium sulfate and concentrated. The residue was purified by silica gel flash column chromatography (10% to 25% EtOAc/CH$_2$Cl$_2$) to give tert-butyl (R)-(4-(2-((1H-indole-2-yl)(2-methoxyphenyl)methyl)-3-oxoisoindole-5-yl)phenyl)carbamate (30 mg, yellow solid, yield: 80%).

$^1$H NMR (300 MHz, methanol-d4) δ 8.00 (d, J=1.6 Hz, 1H), 7.81 (dd, J=7.9, 1.7 Hz, 1H), 7.62-7.41 (m, 7H), 7.44-7.31 (m, 1H), 7.31 (d, J=8.0 Hz, 1H), 7.18-6.93 (m, 7H), 6.14 (s, 1H), 4.46 (d, J=18.1 Hz, 1H), 4.22 (d, J=18.1 Hz, 1H), 3.80 (s, 3H), 1.55 (s, 9H).

Step 3: Preparation of (R)-6-(4-aminophenyl)-2-((2-hydroxyphenyl)(1H-indole-2-yl)methyl)isoindolin-1-one (R)-6-(4-aminophenyl)-2-((2-hydroxyphenyl)(1H-indole-2-yl)methyl)isoindolin-1-one (0.96 mg, 12%) was obtained by performing the same method as in step 3 of Example 1.

$^1$H NMR (300 MHz, methanol-d4) δ 8.06 (d, J=1.7 Hz, 1H), 7.89 (dd, J=8.0, 1.8 Hz, 1H), 7.81-7.75 (m, 2H), 7.62 (d, J=8.0 Hz, 1H), 7.47 (d, J=7.8 Hz, 1H), 7.39-7.29 (m, 3H), 7.23 (td, J=7.8, 7.4, 1.7 Hz, 1H), 7.17 (s, 1H), 7.12-7.04 (m, 2H), 6.99 (td, J=7.5, 7.0, 1.1 Hz, 1H), 6.93-6.82 (m, 2H), 6.19 (d, J=1.0 Hz, 1H), 4.59 (d, J=18.2 Hz, 1H), 4.27 (d, J=18.3 Hz, 1H); LC-MS (M+H$^+$) calcd for C$_{29}$H$_{23}$N$_3$O$_2$, 445.2 found 446.0.

<Example 29> Preparation of (R)-6-(4-aminophenyl)-2-((5-fluoro-2-hydroxyphenyl)(1H-indole-2-yl)methyl)isoindolin-1-one Step 1: Preparation of (R)-6-bromo-2-((5-fluoro-2-methoxyphenyl)(1H-indole-2-yl)methyl)isoindolin-1-one (R)-6-bromo-2-((5-fluoro-2-methoxyphenyl)(1H-indole-2-yl)methyl)isoindolin-1-one (3.3 g, 63%) was obtained by performing the same method as in step 1 of Example 28.

$^1$H NMR (300 MHz, chloroform-d) δ 7.76 (s, 1H), 7.66-7.53 (m, 2H), 7.34 (d, J=8.0 Hz, 1H), 7.25 (s, 1H), 7.22-7.16 (m, 1H), 7.15-7.00 (m, 5H), 6.84 (dd, J=10.1, 4.2 Hz, 1H), 6.28 (s, 1H), 4.37 (d, J=3.1 Hz, 2H), 3.70-3.64 (m, 3H).

Step 2: Preparation of tert-butyl (R)-(4-(2-((5-fluoro-2-methoxyphenyl)(1H-indole-2-yl)methyl)-3-oxoisoindole-5-yl)phenyl)carbamate Tert-butyl (R)-(4-(2-((5-fluoro-2-methoxyphenyl)(1H-indole-2-yl)methyl)-3-oxoisoindole-5-yl)phenyl)carbamate (27.9 mg, 75%) was obtained by performing the same method as in step 2 of Example 28.

$^1$H NMR (500 MHz, chloroform-d) δ 7.84 (d, J=1.6 Hz, 1H), 7.62-7.56 (m, 2H), 7.42 (d, J=8.2 Hz, 1H), 7.40-7.32 (m, 4H), 7.24 (d, J=8.0 Hz, 1H), 7.22-7.18 (m, 1H), 7.15-7.12 (m, 1H), 7.11 (d, J=2.6 Hz, 1H), 7.04 (td, J=8.0, 2.6 Hz, 2H), 6.87-6.83 (m, 1H), 6.80 (d, J=8.8 Hz, 0H), 6.59 (s, 1H), 6.29-6.24 (m, 1H), 4.39 (d, J=17.4 Hz, 1H), 4.24 (d, J=17.5 Hz, 1H), 3.70 (s, 3H), 1.57 (s, 9H).

Step 3: Preparation of (R)-6-(4-aminophenyl)-2-((5-fluoro-2-hydroxyphenyl)(1H-indole-2-yl)methyl)isoindolin-1-one (R)-6-(4-aminophenyl)-2-((5-fluoro-2-hydroxyphenyl)(1H-indole-2-yl)methyl)isoindolin-1-one (3.6 mg, 2%) was obtained by performing the same method as in step 3 of Example 1.

$^1$H NMR (300 MHz, methanol-d4) δ 8.04 (d, J=1.7 Hz, 1H), 7.88 (dd, J=7.9, 1.8 Hz, 1H), 7.70 (d, J=8.2 Hz, 2H), 7.61 (d, J=8.0 Hz, 1H), 7.49 (d, J=7.8 Hz, 1H), 7.34 (d, J=8.1 Hz, 1H), 7.21 (d, J=8.1 Hz, 2H), 7.09 (d, J=7.6 Hz, 2H), 7.05-6.94 (m, 2H), 6.87 (dd, J=8.9, 4.7 Hz, 1H), 6.80 (dd, J=9.4, 3.1 Hz, 1H), 6.22 (s, 1H), 4.57 (d, J=18.0 Hz, 1H), 4.32 (d, J=18.0 Hz, 1H)); LC-MS (M+H$^+$) calcd for C29H22FN3O2, 463 found 464.1.

<Example 30> Preparation of (R)-6-(4-aminophenyl)-2-((5-chloro-2-hydroxyphenyl)(1H-indole-2-yl)methyl)isoindolin-1-one Step 1: Preparation of (R)-6-bromo-2-((5-chloro-2-methoxyphenyl)(1H-indole-2-yl)methyl)isoindolin-1-one (R)-6-bromo-2-((5-chloro-2-methoxyphenyl)(1H-indole-2-yl)methyl)isoindolin-1-one (1.2 g, 67%) was obtained by performing the same method as in step 1 of Example 28.

$^1$H NMR (300 MHz, DMSO-d6) δ 11.25 (s, 1H), 7.86 (d, J=1.8 Hz, 1H), 7.81 (dd, J=8.1, 1.9 Hz, 1H), 7.55 (d, J=8.1 Hz, 1H), 7.50-7.41 (m, 2H), 7.31 (d, J=8.1 Hz, 1H), 7.14 (d, J=8.8 Hz, 2H), 7.07 (dd, J=5.7, 2.1 Hz, 2H), 6.98 (t, J=7.3 Hz, 1H), 6.89 (s, 1H), 6.11 (s, 1H), 4.29 (s, 2H), 3.76 (s, 3H).

Step 2: Preparation of tert-butyl (R)-(4-(2-((5-chloro-2-methoxyphenyl)(1H-indole-2-yl)methyl)-3-oxoisoindole-5-yl)phenyl)carbamate Tert-butyl (R)-(4-(2-((5-chloro-2-methoxyphenyl)(1H-indole-2-yl)methyl)-3-oxoisoindole-5-yl)phenyl)carbamate (42 mg, 71%) was obtained by performing the same method as in step 2 of Example 28.

$^1$H NMR (300 MHz, methanol-d4) δ 8.03 (d, J=1.6 Hz, 1H), 7.88 (dd, J=8.0, 1.8 Hz, 1H), 7.68-7.56 (m, 3H), 7.54 (d, J=8.7 Hz, 2H), 7.49 (d, J=7.9 Hz, 1H), 7.39 (dd, J=8.8, 2.5 Hz, 1H), 7.37-7.32 (m, 1H), 7.17-7.07 (m, 4H), 7.07-6.98 (m, 1H), 6.19 (d, J=1.1 Hz, 1H), 4.51 (d, J=18.0 Hz, 1H), 4.30 (d, J=18.0 Hz, 1H), 3.83 (s, 3H).

Step 3: Preparation of (R)-6-(4-aminophenyl)-2-((5-chloro-2-hydroxyphenyl)(1H-indole-2-yl)methyl)isoindolin-1-one (R)-6-(4-aminophenyl)-2-((5-chloro-2-hydroxyphenyl)(1H-indole-2-yl)methyl)isoindolin-1-one (0.57 mg, 12%) was obtained by performing the same method as in step 3 of Example 1.

$^1$H NMR (500 MHz, methanol-d4) δ 6.51 (s, 1H), 6.36-6.34 (m, 1H), 6.19 (d, J=8.5 Hz, 2H), 6.09 (d, J=8.0 Hz, 1H), 5.96 (d, J=7.9 Hz, 1H), 5.82 (d, J=8.2 Hz, 1H), 5.71-5.68 (m, 3H), 5.60-5.55 (m, 2H), 5.49-5.46 (m, 2H), 5.36 (d, J=8.6 Hz, 1H), 4.69 (s, 1H), 3.05 (d, J=17.9 Hz, 1H), 2.79 (d, J=18.0 Hz, 1H); LC-MS (M+H$^+$) calcd for C29H22ClN3O2, 479.14 found 480.0.

[Reaction Formula j]

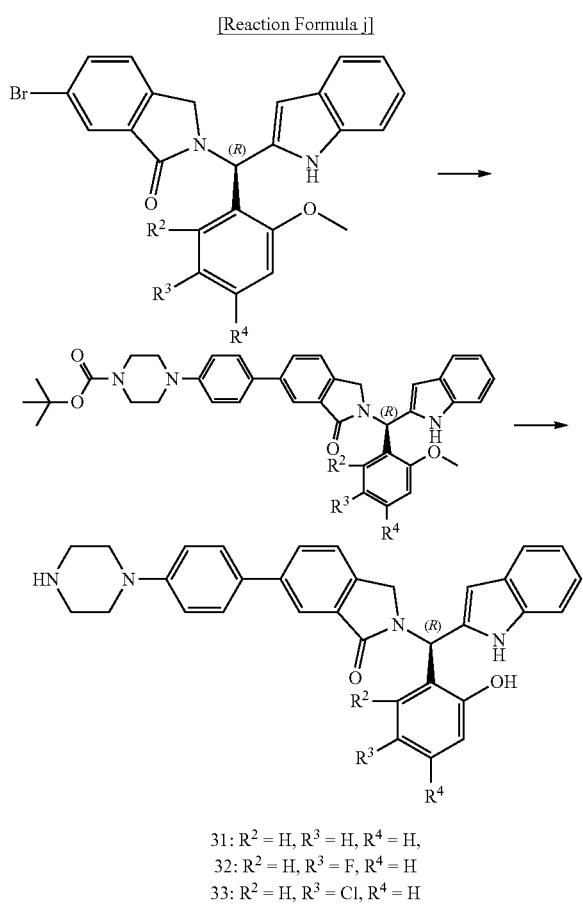

31: R² = H, R³ = H, R⁴ = H,
32: R² = H, R³ = F, R⁴ = H
33: R² = H, R³ = Cl, R⁴ = H

According to reaction formula j, the compounds of Examples 31 to 33 were obtained. In reaction formula j, 31 is the compound of Example 31, 32 is the compound of Example 32, and 33 is the compound of Example 33.

<Example 31> Preparation of (R)-2-((2-hydroxyphenyl)(1H-indole-2-yl)methyl)-6-(4-(piperazine-1-yl)phenyl)isoindolin-1-one Step 1: Preparation of tert-butyl (R)-4-(4-(2-((1H-indole-2-yl)(2-methoxyphenyl)methyl)-3-oxoisoindole-5-yl)phenyl)piperazine-1-carboxylate 4-(4-Boc-piperazinyl)phenylboronic acid pinacol ester (78 mg, 0.201 mmol), (R)-2-((1H-indole-2-yl)(2-methoxyphenyl)methyl)-6-bromoisoindolin-1-one (30 mg, 0.067 mmol), Pd(OAc)$_2$ (0.7 mg, 0.003 mmol), Sphos (2.5 mg, 0.006 mmol) and sodium carbonate (21.3 mg, 0.201 mmol) were degassed in 1,4-dioxane/H$_2$O (0.268/0.067 mL) for 10 minutes, followed by stirring at 100° C. overnight. The reaction mixture was diluted with ethyl acetate and washed with water and brine. The organic layer was dried over anhydrous magnesium sulfate and concentrated. The residue was purified by silica gel flash column chromatography (10% to 25% EtOAc/CH$_2$Cl$_2$) to give tert-butyl (R)-4-(4-(2-((1H-indole-2-yl)(2-methoxyphenyl)methyl)-3-oxoisoindole-5-yl)phenyl)piperazine-1-carboxylate (25 mg, yellow solid, yield: 59%).

$^1$H NMR (300 MHz, methanol-d4) δ 7.99 (d, J=1.6 Hz, 1H), 7.82 (dd, J=8.0, 1.7 Hz, 1H), 7.58 (d, J=8.7 Hz, 2H), 7.51 (d, J=8.1 Hz, 1H), 7.46 (dd, J=7.7, 1.2 Hz, 1H), 7.39 (td, J=7.9, 7.4, 1.7 Hz, 1H), 7.32 (dd, J=8.1, 1.0 Hz, 1H), 7.16 (s, 1H), 7.15-7.05 (m, 5H), 7.02-6.94 (m, 2H), 6.14 (d, J=0.9 Hz, 1H), 4.47 (d, J=18.0 Hz, 1H), 4.22 (d, J=18.0 Hz, 1H), 3.81 (s, 3H), 3.60 (t, J=5.1 Hz, 4H), 3.20 (dd, J=6.3, 4.1 Hz, 4H), 1.51 (s, 9H).

Step 2: Preparation of (R)-2-((2-hydroxyphenyl)(1H-indole-2-yl)methyl)-6-(4-(piperazine-1-yl)phenyl)isoindolin-1-one (R)-2-((2-hydroxyphenyl)(1H-indole-2-yl)methyl)-6-(4-(piperazine-1-yl)phenyl)isoindolin-1-one (1 mg, 13%) was obtained by performing the same method as in step 3 of Example 1.

$^1$H NMR (300 MHz, methanol-d4) δ 8.03 (d, J=0.9 Hz, 1H), 7.86 (dd, J=8.0, 1.8 Hz, 1H), 7.67 (d, J=8.7 Hz, 2H), 7.58 (d, J=8.0 Hz, 1H), 7.47 (d, J=7.8 Hz, 1H), 7.32 (d, J=8.0 Hz, 1H), 7.27-7.20 (m, 1H), 7.19-7.14 (m, 3H), 7.08 (dq, J=7.2, 3.9, 3.3 Hz, 2H), 7.02-6.95 (m, 1H), 6.93-6.83 (m, 2H), 6.19 (s, 1H), 4.57 (d, J=18.1 Hz, 1H), 4.26 (d, J=18.1 Hz, 1H), 3.53-3.48 (m, 5H), 3.45-3.39 (m, 4H); LC-MS (M+H$^+$) calcd for C$_{33}$H$_{30}$N$_4$O$_2$, 514.2 found 515.1.

<Example 32> Preparation of (R)-2-((5-fluoro-2-hydroxyphenyl)(1H-indole-2-yl)methyl)-6-(4-(piperazine-1-yl)phenyl)isoindolin-1-one Step 1: Preparation of tert-butyl (R)-4-(4-(2-((5-fluoro-2-methoxyphenyl)(1H-indole-2-yl)methyl)-3-oxoisoindole-5-yl)phenyl)piperazine-1-carboxylate Tert-butyl (R)-4-(4-(2-((5-fluoro-2-methoxyphenyl)(1H-indole-2-yl)methyl)-3-oxoisoindole-5-yl)phenyl)piperazine-1-carboxylate (20.6 mg, 50%) was obtained by performing the same method as in step 1 of Example 31.

$^1$H NMR (300 MHz, methanol-d4) δ 8.02 (s, 1H), 7.85 (dd, J=8.0, 1.7 Hz, 1H), 7.63 (d, J=8.7 Hz, 2H), 7.56 (d, J=8.0 Hz, 1H), 7.48 (d, J=7.8 Hz, 1H), 7.34 (d, J=8.1 Hz, 1H), 7.11 (td, J=8.0, 7.3, 5.3 Hz, 5H), 7.01 (t, J=7.3 Hz, 1H), 6.87 (dd, J=9.1, 2.9 Hz, 1H), 6.18 (d, J=1.0 Hz, 1H), 4.49 (d, J=17.9 Hz, 1H), 4.31 (d, J=17.9 Hz, 1H), 3.81 (s, 3H), 3.62 (d, J=5.4 Hz, 4H), 3.24 (t, J=5.2 Hz, 4H), 1.51 (s, 8H).

Step 2: Preparation of (R)-2-((5-fluoro-2-hydroxyphenyl)(1H-indole-2-yl)methyl)-6-(4-(piperazine-1-yl)phenyl)isoindolin-1-one (R)-2-((5-fluoro-2-hydroxyphenyl)(1H-indole-2-yl)methyl)-6-(4-(piperazine-1-yl)phenyl)isoindolin-1-one (1.1 mg, 9.3%) was obtained by performing the same method as in step 3 of Example 1.

1H NMR (300 MHz, methanol-d4) δ 8.04-8.00 (m, 1H), 7.86 (dd, J=8.0, 1.7 Hz, 1H), 7.66 (d, J=8.7 Hz, 2H), 7.59 (d, J=8.0 Hz, 1H), 7.49 (d, J=7.7 Hz, 1H), 7.34 (d, J=8.1 Hz, 1H), 7.16 (d, J=8.7 Hz, 2H), 7.13-7.07 (m, 2H), 7.04-6.94 (m, 2H), 6.87 (dd, J=8.8, 4.6 Hz, 1H), 6.80 (dd, J=9.4, 3.1 Hz, 1H), 6.22 (t, J=0.9 Hz, 1H), 4.56 (d, J=18.0 Hz, 1H), 4.31 (d, J=17.9 Hz, 1H), 3.50 (dd, J=7.0, 3.6 Hz, 4H), 3.44-3.38 (m, 4H); LC-MS (M+H$^+$) calcd for C33H29FN4O2, 532.23 found 533.1.

<Example 33> Preparation of (R)-2-((5-chloro-2-hydroxyphenyl)(1H-indole-2-yl)methyl)-6-(4-(piperazine-1-yl)phenyl)isoindolin-1-one Step 1: Preparation of tert-butyl (R)-4-(4-(2-((5-chloro-2-methoxyphenyl)(1H-indole-2-yl)methyl)-3-oxoisoindole-5-yl)phenyl)piperazine-1-carboxylate Tert-butyl (R)-4-(4-(2-((5-chloro-2-methoxyphenyl)(1H-indole-2-yl)methyl)-3-oxoisoindole-5-yl)phenyl)piperazine-1-carboxylate (38 mg, 57%) was obtained by performing the same method as in step 1 of Example 31.

¹H NMR (300 MHz, methanol-d4) δ 8.01 (d, J=1.6 Hz, 1H), 7.84 (dd, J=8.0, 1.7 Hz, 1H), 7.60 (d, J=8.7 Hz, 2H), 7.55 (d, J=8.0 Hz, 1H), 7.49 (d, J=7.8 Hz, 1H), 7.42-7.31 (m, 2H), 7.09 (td, J=5.3, 4.5, 3.1 Hz, 6H), 7.04-6.98 (m, 1H), 6.18 (s, 1H), 4.48 (d, J=17.9 Hz, 1H), 4.28 (d, J=17.9 Hz, 1H), 3.82 (s, 3H), 3.61 (t, J=5.2 Hz, 4H), 3.21 (t, J=5.2 Hz, 4H).

Step 2: Preparation of (R)-2-((5-chloro-2-hydroxyphenyl)(1H-indole-2-yl)methyl)-6-(4-(piperazine-1-yl)phenyl)isoindolin-1-one (R)-2-((5-chloro-2-hydroxyphenyl)(1H-indole-2-yl)methyl)-6-(4-(piperazine-1-yl)phenyl)isoindolin-1-one (1 mg, 12%) was obtained by performing the same method as in step 3 of Example 1.

¹H NMR (300 MHz, methanol-d4) δ 8.04-7.99 (m, 1H), 7.86 (dd, J=8.0, 1.7 Hz, 1H), 7.66 (d, J=8.6 Hz, 2H), 7.59 (d, J=8.0 Hz, 1H), 7.49 (d, J=7.8 Hz, 1H), 7.35 (d, J=8.1 Hz, 1H), 7.22 (dd, J=8.6, 2.6 Hz, 1H), 7.15 (d, J=8.8 Hz, 2H), 7.10 (d, J=5.9 Hz, 2H), 7.06-6.98 (m, 2H), 6.89 (d, J=8.5 Hz, 1H), 6.22 (d, J=1.0 Hz, 1H), 4.56 (d, J=17.9 Hz, 1H), 4.29 (d, J=17.9 Hz, 1H), 3.50 (dd, J=6.9, 3.7 Hz, 4H), 3.41 (dd, J=6.9, 3.7 Hz, 4H); LC-MS (M+H⁺) calcd for C33H29ClN4O2, 548.2 found 549.1.

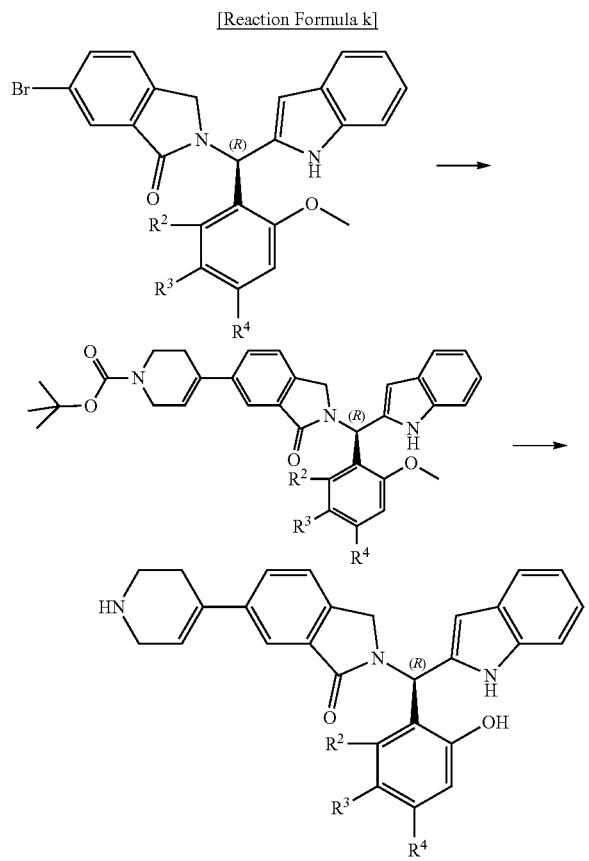

34: R² = H, R³ = H, R⁴ = H,
35: R² = H, R³ = F, R⁴ = H
36: R² = H, R³ = Cl, R⁴ = H

According to reaction formula k, the compounds of Examples 34 to 36 were obtained. In reaction formula k, 34 is the compound of Example 34, 35 is the compound of Example 35, and 36 is the compound of Example 36.

<Example 34> Preparation of (R)-2-((2-hydroxyphenyl)(1H-indole-2-yl)methyl)-6-(1,2,3,6-tetrahydropyridine-4-yl)isoindolin-1-one Step 1: Preparation of tert-butyl (R)-4-(2-((1H-indole-2-yl)(2-methoxyphenyl)methyl)-3-oxoisoindole-5-yl)-3,6-dihydropyridine-1(2H)-carboxylate Tert-butyl 4-(4,4,5,5-tetramethyl-1,3,2-dioxaborolan-2-yl)-5,6-dihydropyridine-1(2H)-carboxylate (63 mg, 0.201 mmol), (R)-2-((1H-indole-2-yl)(2-methoxyphenyl)methyl)-6-bromoisoindolin-1-one (30 mg, 0.067 mmol), Pd(OAc)₂ (0.7 mg, 0.003 mmol), Sphos (2.5 mg, 0.006 mmol) and sodium carbonate (21.3 mg, 0.201 mmol) were degassed in 1,4-dioxane/H₂O (0.268/0.067 mL) for 10 minutes, followed by stirring at 100° C. overnight. The reaction mixture was diluted with ethyl acetate and washed with water and brine. The organic layer was dried over anhydrous magnesium sulfate and concentrated. The residue was purified by silica gel flash column chromatography (10% to 25% EtOAc/CH₂Cl₂) to give tert-butyl (R)-4-(2-((1H-indole-2-yl)(2-methoxyphenyl)methyl)-3-oxoisoindole-5-yl)-3,6-dihydropyridine-1(2H)-carboxylate (20 mg, yellow solid, yield: 56%).

¹H NMR (300 MHz, methanol-d4) δ 7.83 (s, 1H), 7.71-7.64 (m, 1H), 7.45 (d, J=7.8 Hz, 2H), 7.38 (td, J=7.9, 1.7 Hz, 1H), 7.31 (d, J=8.1 Hz, 1H), 7.17-7.04 (m, 4H), 7.02-6.93 (m, 2H), 6.19 (s, 1H), 6.12 (d, J=1.0 Hz, 1H), 4.43 (d, J=18.1 Hz, 1H), 4.20 (d, J=18.1 Hz, 1H), 4.12-4.07 (m, 2H), 3.80 (s, 3H), 3.67 (t, J=5.7 Hz, 2H), 2.57 (s, 2H).

Step 2: Preparation of (R)-2-((2-hydroxyphenyl)(1H-indole-2-yl)methyl)-6-(1,2,3,6-tetrahydropyridine-4-yl)isoindolin-1-one (R)-2-((2-hydroxyphenyl)(1H-indole-2-yl)methyl)-6-(1,2,3,6-tetrahydropyridine-4-yl)isoindolin-1-one (0.9 mg, 11%) was obtained by performing the same method as in step 3 of Example 1.

¹H NMR (300 MHz, methanol-d4) δ 7.91 (s, 1H), 7.76 (dd, J=8.0, 1.8 Hz, 1H), 7.55 (d, J=8.0 Hz, 1H), 7.46 (d, J=7.7 Hz, 1H), 7.31 (d, J=8.0 Hz, 1H), 7.23 (t, J=6.9 Hz, 1H), 7.14 (s, 1H), 7.08 (t, J=8.0 Hz, 2H), 6.99 (t, J=7.2 Hz, 1H), 6.92-6.82 (m, 2H), 6.29 (s, 1H), 6.16 (s, 1H), 4.56 (d, J=18.3 Hz, 1H), 4.24 (d, J=18.2 Hz, 1H), 3.87 (s, 2H), 3.48 (d, J=5.8 Hz, 1H), 2.87 (s, 2H); LC-MS (M+H⁺) calcd for C28H25N3O2, 435.2 found 436.1.

<Example 35> Preparation of (R)-2-((5-fluoro-2-hydroxyphenyl)(1H-indole-2-yl)methyl)-6-(1,2,3,6-tetrahydropyridine-4-yl)isoindolin-1-one Step 1: Preparation of tert-butyl (R)-4-(2-((5-fluoro-2-methoxyphenyl)(1H-indole-2-yl)methyl)-3-oxoisoindole-5-yl)-3,6-dihydropyridine-1(2H)-carboxylate Tert-butyl (R)-4-(2-((5-fluoro-2-methoxyphenyl)(1H-indole-2-yl)methyl)-3-oxoisoindole-5-yl)-3,6-dihydropyridine-1(2H)-carboxylate (21 mg, 57%) was obtained by performing the same method as in step 1 of Example 34.

¹H NMR (300 MHz, chloroform-d) δ 7.63 (s, 1H), 7.56 (d, J=7.8 Hz, 1H), 7.43 (t, J=7.4 Hz, 2H), 7.21 (t, J=7.5 Hz, 1H), 7.12 (t, J=6.9 Hz, 1H), 7.08-6.93 (m, 3H), 6.86 (dd, J=8.9, 4.4 Hz, 1H), 6.24 (s, 1H), 5.85 (s, 1H), 4.35 (d, J=17.6 Hz, 1H), 4.05 (d, J=29.1 Hz, 3H), 3.72 (s, 3H), 3.56 (s, 2H), 2.33 (s, 2H), 1.52 (s, 9H).

Step 2: Preparation of (R)-2-((5-fluoro-2-hydroxyphenyl)(1H-indole-2-yl)methyl)-6-(1,2,3,6-tetrahydropyridine-4-yl)isoindolin-1-one (R)-2-((5-fluoro-2-hydroxyphenyl)(1H-indole-2-yl)methyl)-6-(1,2,3,6-tetrahydropyridine-4-yl)isoindolin-1-one (1 mg, 12%) was obtained by performing the same method as in step 3 of Example 1.

¹H NMR (300 MHz, methanol-d4) δ 7.91 (d, J=1.6 Hz, 1H), 7.77 (dd, J=8.0, 1.7 Hz, 1H), 7.57 (d, J=8.0 Hz, 1H), 7.48 (d, J=7.8 Hz, 1H), 7.34 (d, J=8.1 Hz, 1H), 7.12-7.06 (m, 2H), 7.04-6.93 (m, 2H), 6.87 (dd, J=8.8, 4.6 Hz, 1H), 6.77 (dd, J=9.4, 3.1 Hz, 1H), 6.29 (s, 1H), 6.20 (s, 1H), 4.55 (d, J=18.1 Hz, 1H), 4.29 (d, J=18.2 Hz, 1H), 3.90 (d, J=3.2 Hz, 2H), 3.52 (t, J=6.1 Hz, 2H), 2.89 (s, 2H); LC-MS (M+H⁺) calcd for C28H24FN3O2, 453.2 found 454.0.

<Example 36> Preparation of (R)-2-((5-chloro-2-hydroxyphenyl)(1H-indole-2-yl)methyl)-6-(1,2,3,6-tetrahydropyridine-4-yl)isoindolin-1-one Step 1: Preparation of tert-butyl (R)-4-(2-((5-chloro-2-methoxyphenyl)(1H-indole-2-yl)methyl)-3-oxoisoindole-5-yl)-3,6-dihydropyridine-1(2H)-carboxylate Tert-butyl (R)-4-(2-((5-fluoro-2-methoxyphenyl)(1H-indole-2-yl)methyl)-3-oxoisoindole-5-yl)-3,6-dihydropyridine-1(2H)-carboxylate (40 mg, 57%) was obtained by performing the same method as in step 1 of Example 34.

¹H NMR (300 MHz, methanol-d4) δ 7.86 (d, J=1.6 Hz, 1H), 7.72 (dd, J=8.0, 1.7 Hz, 1H), 7.49 (t, J=7.6 Hz, 2H), 7.38 (dd, J=8.8, 2.5 Hz, 1H), 7.36-7.31 (m, 1H), 7.14-7.05 (m, 4H), 7.01 (td, J=7.5, 1.1 Hz, 1H), 6.23 (s, 1H), 6.17 (d, J=1.6 Hz, 1H), 4.46 (d, J=17.9 Hz, 1H), 4.26 (d, J=18.0 Hz, 1H), 4.12 (s, 2H), 3.81 (s, 3H), 3.69 (t, J=5.7 Hz, 2H), 2.61 (s, 2H).

Step 2: Preparation of (R)-2-((5-chloro-2-hydroxyphenyl)(1H-indole-2-yl)methyl)-6-(1,2,3,6-tetrahydropyridine-4-yl)isoindolin-1-one (R)-2-((5-fluoro-2-hydroxyphenyl)(1H-indole-2-yl)methyl)-6-(1,2,3,6-tetrahydropyridine-4-yl)isoindolin-1-one (0.8 mg, 8%) was obtained by performing the same method as in step 3 of Example 1.

¹H NMR (300 MHz, methanol-d4) δ 10.68 (s, 1H), 7.91 (d, J=1.6 Hz, 1H), 7.77 (dd, J=8.0, 1.7 Hz, 1H), 7.58 (d, J=8.0 Hz, 1H), 7.48 (d, J=7.8 Hz, 1H), 7.34 (d, J=8.0 Hz, 1H), 7.22 (dd, J=8.7, 2.6 Hz, 1H), 7.15-7.07 (m, 1H), 7.07-6.97 (m, 3H), 6.88 (d, J=8.6 Hz, 1H), 6.29 (s, 1H), 6.20 (d, J=1.4 Hz, 1H), 4.55 (d, J=18.1 Hz, 1H), 4.29 (d, J=18.1 Hz, 1H), 3.90 (d, J=3.1 Hz, 2H), 3.52 (t, J=6.1 Hz, 2H), 2.89 (s, 2H); LC-MS (M+H⁺) calcd for C28H24FN3O2, 469.2 found 470.0.

[Reaction Formula 1]

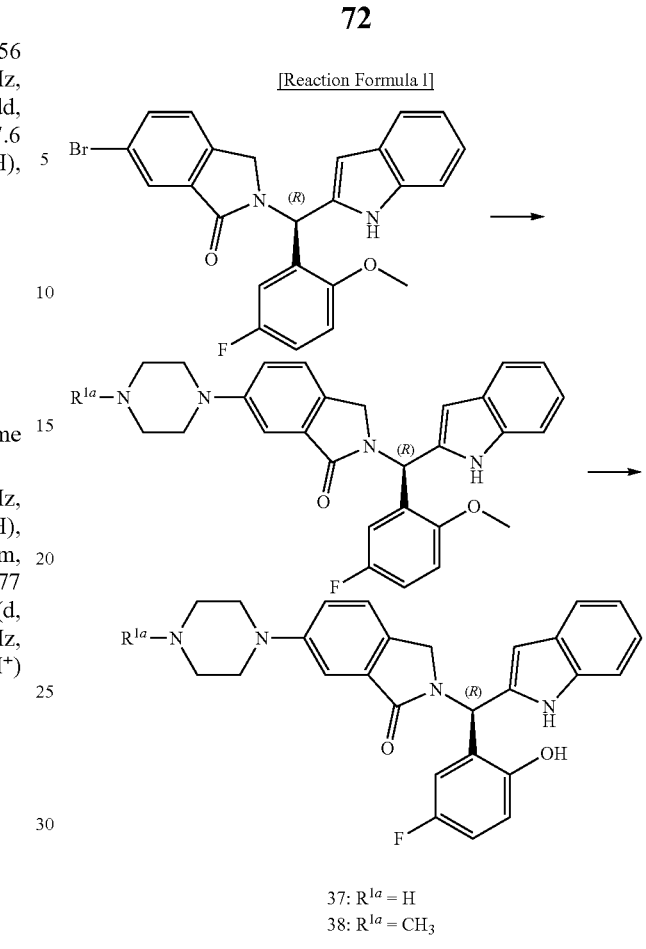

37: R¹ᵃ = H
38: R¹ᵃ = CH3

According to reaction formula 1, the compounds of Examples 37 and 38 were obtained. In reaction formula 1, 37 is the compound of Example 37, and 38 is the compound of Example 38.

<Example 37> Preparation of (R)-2-((5-fluoro-2-hydroxyphenyl)(1H-indole-2-yl)methyl)-6-(piperazine-1-yl)isoindolin-1-one Step 1: Preparation of (R)-2-((5-fluoro-2-methoxyphenyl)(1H-indole-2-yl)methyl)-6-(piperazine-1-yl)isoindolin-1-one Piperazine (5.12 mg, 0.06 mmol), (R)-6-bromo-2-((5-fluoro-2-methoxyphenyl)(1H-indole-2-yl)methyl)isoindolin-1-one (10 mg, 0.022 mmol), tBuXPhos Pd G1 (0.21 mg, 0.0003 mmol), sodium tert-butoxide (5.8 mg, 0.06 mmol) were degassed in toluene (0.11 mL) for 10 minutes. The stirred suspension was heated at 100° C. overnight, diluted in ethyl acetate, which was washed with water and brine. The organic layer was dried over anhydrous magnesium sulfate and concentrated. The residue was purified by HPLC to give (R)-2-((5-fluoro-2-methoxyphenyl)(1H-indole-2-yl)methyl)-6-(piperazine-1-yl)isoindolin-1-one (2 mg, white solid, yield: 19%).

¹H NMR (300 MHz, methanol-d4) δ 7.50-7.40 (m, 3H), 7.38-7.30 (m, 2H), 7.14-7.05 (m, 4H), 7.00 (t, J=7.7 Hz, 1H), 6.82 (dd, J=9.1, 2.8 Hz, 1H), 6.15 (s, 1H), 4.40 (d, J=17.6 Hz, 1H), 4.21 (d, J=17.8 Hz, 1H), 3.80 (s, 3H), 3.48 (s, 4H), 3.41 (s, 4H); LC-MS (M+H⁺) calcd for C28H27FN4O2, 470.2 found 471.1.

Step 2: Preparation of (R)-2-((5-fluoro-2-hydroxyphenyl)(1H-indole-2-yl)methyl)-6-(piperazine-1-yl)isoindolin-1-one (R)-2-((5-fluoro-2-hydroxyphenyl)(1H-indole-2-yl)methyl)-6-(piperazine-1-yl)isoindolin-1-one (0.5 mg, 27%) was obtained by performing the same method as in step 3 of Example 1.
LC-MS (M+H$^+$) calcd for C27H25FN4O2, 456.2 found 457.0.

<Example 38> Preparation of (R)-2-((5-fluoro-2-hydroxyphenyl)(1H-indole-2-yl)methyl)-6-(4-methylpiperazine-1-yl)isoindolin-1-one Step 1: Preparation of (R)-2-((5-fluoro-2-methoxyphenyl)(1H-indole-2-yl)methyl)-6-(4-methylpiperazine-1-yl)isoindolin-1-one (R)-2-((5-fluoro-2-methoxyphenyl)(1H-indole-2-yl)methyl)-6-(4-methylpiperazine-1-yl)isoindolin-1-one (5 mg, 16%) was obtained by performing the same method as in step 1 of Example 37.
LC-MS (M+H$^+$) calcd for C29H30FN4O2, 484.2 found 485.0.

Step 2: Preparation of (R)-2-((5-fluoro-2-hydroxyphenyl)(1H-indole-2-yl)methyl)-6-(4-methylpiperazine-1-yl)isoindolin-1-one (R)-2-((5-fluoro-2-hydroxyphenyl)(1H-indole-2-yl)methyl)-6-(4-methylpiperazine-1-yl)isoindolin-1-one (0.4 mg, 17%) was obtained by performing the same method as in step 3 of Example 1.
LC-MS (M+H$^+$) calcd for C28H27FN4O2, 470.2 found 471.1.

The compounds of Examples 38 to 71 were prepared by performing the method similar to reaction formulas d to m.

<Example 39> Preparation of 2-((1H-benzo[d]imidazole-2-yl)(5-fluoro-2-hydroxyphenyl)methyl)-6-(4-morpholinophenyl)isoindolin-1-one 1H NMR (300 MHz, Methanol-d4) δ 8.08 (d, J=1.7 Hz, 1H), 7.95 (dd, J=8.0, 1.8 Hz, 1H), 7.76 (dd, J=6.2, 3.2 Hz, 2H), 7.70-7.59 (m, 5H), 7.26-7.16 (m, 5H), 7.01 (dd, J=8.8, 4.4 Hz, 1H), 4.83 (s, 1H), 4.43 (d, J=17.4 Hz, 1H), 3.93-3.89 (m, 6H), 3.31-3.27 (m, 4H).

<Example 40> Preparation of 2-((1H-benzo[d]imidazole-2-yl)(5-chloro-2-hydroxyphenyl)methyl)-6-(4-morpholinophenyl)isoindolin-1-one $^1$H NMR (300 MHz, Methanol-d$_4$) δ 8.02 (dd, J=1.8, 0.7 Hz, 1H), 7.86 (dd, J=8.0, 1.8 Hz, 1H), 7.62 (d, J=8.8 Hz, 2H), 7.57 (d, J=8.0 Hz, 1H), 7.49 (d, J=7.8 Hz, 1H), 7.35 (dd, J=8.1, 1.0 Hz, 1H), 7.22 (dd, J=8.6, 2.6 Hz, 1H), 7.13-7.07 (m, 4H), 7.05-7.00 (m, 2H), 6.88 (d, J=8.6 Hz, 1H), 4.55 (d, J=17.9 Hz, 1H), 4.29 (d, J=17.9 Hz, 1H), 3.91-3.84 (m, 4H), 3.26-3.20 (m, 4H).

<Example 41> Preparation of 2-((1H-benzo[d]imidazole-2-yl)(5-fluoro-2-hydroxyphenyl)methyl)-6-(4-(pyridine-4-yl)phenyl)isoindolin-1-one $^1$H NMR (300 MHz, Methanol-d$_4$) δ 8.87 (d, J=5.6 Hz, 2H), 8.45-8.38 (m, 2H), 8.24 (s, 1H), 8.18-8.07 (m, 3H), 8.01 (dd, J=8.4, 2.1 Hz, 2H), 7.75 (qd, J=5.7, 3.7, 2.3 Hz, 3H), 7.60 (dt, J=6.0, 2.8 Hz, 2H), 7.26-7.16 (m, 3H), 7.01 (t, J=6.5 Hz, 1H), 4.48 (d, J=17.5 Hz, 1H).

<Example 42> Preparation of 2-((1H-benzo[d]imidazole-2-yl)(5-chloro-2-hydroxyphenyl)methyl)-6-(4-(pyridine-4-yl)phenyl)isoindolin-1-one $^1$H NMR (300 MHz, Methanol-d$_4$) δ 8.85 (d, J=6.0 Hz, 2H), 8.36 (d, J=6.1 Hz, 2H), 8.23 (d, J=1.7 Hz, 1H), 8.17-8.05 (m, 3H), 8.00 (d, J=8.6 Hz, 2H), 7.79-7.70 (m, 3H), 7.57 (dd, J=6.2, 3.2 Hz, 2H), 7.46-7.38 (m, 2H), 7.20 (s, 1H), 7.04-6.97 (m, 1H), 4.46 (d, J=17.5 Hz, 1H).

<Example 43> Preparation of (R)-2-((5-fluoro-2-hydroxyphenyl)(1H-indole-2-yl)methyl)-6-(4-(4-methylpiperazine-1-yl)phenyl)isoindolin-1-one $^1$H NMR (400 MHz, Methanol-d$_4$) δ 8.02 (dd, J=1.7, 0.7 Hz, 1H), 7.86 (dd, J=8.0, 1.8 Hz, 1H), 7.69-7.63 (m, 2H), 7.59 (d, J=8.0 Hz, 1H), 7.49 (d, J=7.8 Hz, 1H), 7.34 (dd, J=8.2, 1.1 Hz, 1H), 7.16 (d, J=8.7 Hz, 2H), 7.12-7.07 (m, 2H), 7.04-6.94 (m, 2H), 6.87 (dd, J=8.8, 4.6 Hz, 1H), 6.80 (dd, J=9.3, 3.1 Hz, 1H), 6.22 (t, J=0.9 Hz, 1H), 4.56 (d, J=18.0 Hz, 1H), 4.31 (d, J=18.0 Hz, 1H), 3.96 (s, 2H), 3.63 (d, J=10.8 Hz, 2H), 3.14 (d, J=12.6 Hz, 2H), 3.00 (s, 3H).

<Example 44> Preparation of (R)-2-((5-chloro-2-hydroxyphenyl)(1H-indole-2-yl)methyl)-6-(4-(4-methylpiperazine-1-yl)phenyl)isoindolin-1-one $^1$H NMR (400 MHz, Methanol-d$_4$) δ 7.90 (s, 1H), 7.75 (d, J=7.9 Hz, 1H), 7.55 (d, J=8.5 Hz, 2H), 7.48 (d, J=8.0 Hz, 1H), 7.37 (d, J=7.9 Hz, 1H), 7.23 (d, J=8.1 Hz, 1H), 7.10 (dd, J=8.6, 2.6 Hz, 1H), 7.04 (d, J=8.6 Hz, 2H), 6.98 (d, J=8.1 Hz, 2H), 6.92-6.86 (m, 2H), 6.77 (d, J=8.6 Hz, 1H), 6.10 (s, 1H), 4.45 (d, J=17.9 Hz, 1H), 4.19 (d, J=18.0 Hz, 1H), 3.85 (s, 2H), 3.51 (d, J=11.6 Hz, 2H), 3.03 (d, J=1.8 Hz, 0H), 2.89 (s, 3H).

<Example 45> Preparation of (R)-2-((5-fluoro-2-hydroxyphenyl)(1H-indole-2-yl)methyl)-6-(4-morpholinophenyl)isoindolin-1-one $^1$H NMR (300 MHz, Methanol-d$_4$) δ 8.01 (dd, J=1.8, 0.7 Hz, 1H), 7.85 (dd, J=8.0, 1.8 Hz, 1H), 7.65-7.54 (m, 3H), 7.49 (dd, J=7.8, 1.1 Hz, 1H), 7.37-7.32 (m, 1H), 7.13-7.06 (m, 3H), 7.04-6.93 (m, 2H), 6.88 (dd, J=8.8, 4.6 Hz, 1H), 6.80 (dd, J=9.4, 3.1 Hz, 1H), 6.22 (t, J=1.0 Hz, 1H), 4.54 (d, J=18.0 Hz, 1H), 4.29 (d, J=17.9 Hz, 1H), 3.91-3.84 (m, 4H), 3.26-3.19 (m, 4H).

<Example 46> Preparation of (R)-2-((5-chloro-2-hydroxyphenyl)(1H-indole-2-yl)methyl)-6-(4-morpholinophenyl)isoindolin-1-one $^1$H NMR (300 MHz, Methanol-d$_4$) δ 8.02 (dd, J=1.8, 0.7 Hz, 1H), 7.86 (dd, J=8.0, 1.8 Hz, 1H), 7.65-7.60 (m, 2H), 7.57 (d, J=8.0 Hz, 1H), 7.49 (d, J=7.8 Hz, 1H), 7.35 (dd, J=8.1, 1.0 Hz, 1H), 7.22 (dd, J=8.6, 2.6 Hz, 1H), 7.14-7.06 (m, 4H), 7.04-7.00 (m, 2H), 6.88 (d, J=8.6 Hz, 1H), 6.22 (t, J=1.0 Hz, 1H), 4.55 (d, J=17.9 Hz, 1H), 4.29 (d, J=17.9 Hz, 1H), 3.93-3.83 (m, 4H), 3.26-3.20 (m, 4H).

<Example 47> Preparation of (R)-2-((5-fluoro-2-hydroxyphenyl)(1H-indole-2-yl)methyl)-6-(4-(pyridine-4-yl)phenyl)isoindolin-1-one $^1$H NMR (300 MHz, Methanol-d$_4$) δ 8.80 (d, J=5.8 Hz, 2H), 8.26 (d, J=5.9 Hz, 2H), 8.17 (d, J=1.6 Hz, 1H), 8.08 (d, J=8.4 Hz, 2H), 8.04-7.93 (m, 3H), 7.69 (d, J=7.9 Hz, 1H), 7.49 (d, J=7.8 Hz, 1H), 7.35 (d, J=8.1 Hz, 1H), 7.14-7.07 (m, 2H), 7.04-6.95 (m, 2H), 6.88 (dd, J=8.9, 4.6 Hz, 1H), 6.81 (dd, J=9.3, 3.1 Hz, 1H), 6.23 (d, J=1.1 Hz, 1H), 4.61 (d, J=18.1 Hz, 1H), 4.36 (d, J=18.1 Hz, 1H).

<Example 48> Preparation of (R)-2-((5-chloro-2-hydroxyphenyl)(1H-indole-2-yl)methyl)-6-(4-(pyridine-4-yl)phenyl)isoindolin-1-one LC-MS (M+H$^+$) calcd for $C_{34}H_{24}ClN_3O_2$ 541.16 found 542.0.

<Example 49> Preparation of (R)-2-((5-fluoro-2-hydroxyphenyl)(1H-pyrrolo[2,3-b]pyridine-2-yl)methyl)-6-(4-(piperazine-4-yl)phenyl)isoindolin-1-one 1H NMR (300 MHz, Methanol-d4) δ 8.39 (dd, J=7.9, 1.3 Hz, 1H), 8.31 (dd, J=5.6, 1.3 Hz, 1H), 8.03 (dd, J=1.7, 0.7 Hz, 1H), 7.89 (dd, J=8.0, 1.8 Hz, 1H), 7.66 (d, J=8.7 Hz, 2H), 7.62 (d, J=8.0 Hz, 1H), 7.42 (dd, J=7.9, 5.6 Hz, 1H), 7.20-7.13 (m, 3H), 7.04 (td, J=8.5, 3.1 Hz, 1H), 6.92 (dd, J=8.8, 4.6 Hz, 1H), 6.81 (dd, J=9.1, 3.1 Hz, 1H), 6.56 (d, J=1.2 Hz, 1H), 4.64 (d, J=17.8 Hz, 1H), 4.31 (d, J=17.7 Hz, 1H), 3.51 (dd, J=6.8, 3.7 Hz, 4H), 3.45-3.39 (m, 4H).

<Example 50> Preparation of (R)-2-((5-chloro-2-hydroxyphenyl)(1H-pyrrolo[2,3-b]pyridine-2-yl)methyl)-6-(4-(piperazine-4-yl)phenyl)isoindolin-1-one 1H NMR (300 MHz, Methanol-d4) δ 8.30-8.24 (m, 1H), 8.03 (d, J=1.8 Hz, 1H), 7.89 (dd, J=8.0, 1.8 Hz, 1H), 7.64 (dd, J=14.6, 8.3 Hz, 3H), 7.34 (dd, J=7.8, 5.4 Hz, 1H), 7.27 (dd, J=8.6, 2.6 Hz, 1H), 7.20-7.11 (m, 3H), 7.01 (d, J=2.6 Hz, 1H), 6.92 (d, J=8.6 Hz, 1H), 6.49 (d, J=1.1 Hz, 1H), 4.63 (d, J=17.8 Hz, 1H), 4.30 (d, J=17.7 Hz, 1H), 3.54-3.48 (m, 4H), 3.46-3.39 (m, 4H).

<Example 51> Preparation of (R)-2-((5-fluoro-1H-indole-2-yl)(5-fluoro-2-hydroxyphenyl)methyl)-6-(4-(piperazine-1-yl)phenyl)isoindolin-1-one 1H NMR (500 MHz, Methanol-d4) δ 6.49 (s, 1H), 6.33 (d, J=8.0 Hz, 1H), 6.13 (d, J=8.2 Hz, 2H), 6.06 (d, J=8.0 Hz, 1H), 5.79-5.74 (m, 1H), 5.63 (d, J=8.8 Hz, 3H), 5.56 (s, 1H), 5.45 (t, J=8.9 Hz, 1H), 5.37-5.31 (m, 2H), 5.26 (d, J=9.2 Hz, 1H), 4.69 (s, 1H), 3.02 (d, J=17.6 Hz, 1H), 2.77 (d, J=17.9 Hz, 1H), 1.97 (d, J=5.5 Hz, 4H), 1.88 (t, J=5.0 Hz, 4H).

<Example 52> Preparation of (R)-2-((5-fluoro-1H-indole-2-yl)(5-fluoro-2-hydroxyphenyl)methyl)-6-(4-(1,2,3,6-tetrahydropyridine-4-yl)phenyl)isoindolin-1-one 1H NMR (400 MHz, Methanol-d4) δ 7.88 (d, J=1.6 Hz, 1H), 7.74 (dd, J=8.0, 1.7 Hz, 1H), 7.54 (d, J=8.0 Hz, 1H), 7.29 (dd, J=8.8, 4.4 Hz, 1H), 7.14 (dd, J=9.8, 2.5 Hz, 1H), 7.07 (s, 1H), 6.97 (td, J=8.4, 3.1 Hz, 1H), 6.90-6.83 (m, 2H), 6.77 (dd, J=9.3, 3.1 Hz, 1H), 6.27-6.23 (m, 1H), 6.20 (d, J=1.1 Hz, 1H), 4.53 (d, J=18.1 Hz, 1H), 4.27 (d, J=18.1 Hz, 1H), 3.89 (d, J=3.0 Hz, 1H), 3.51 (t, J=6.1 Hz, 2H), 2.90-2.82 (m, 2H).

<Example 53> Preparation of (S)-2-((5-fluoro-2-hydroxyphenyl)(1H-indole-2-yl)methyl)-6-(4-(piperazine-1-yl)phenyl)isoindolin-1-one 1H NMR (400 MHz, Methanol-d4) δ 8.02 (d, J=1.7 Hz, 1H), 7.86 (dd, J=8.0, 1.7 Hz, 1H), 7.66 (d, J=8.7 Hz, 2H), 7.59 (d, J=8.0 Hz, 1H), 7.49 (dt, J=7.9, 1.0 Hz, 1H), 7.34 (dd, J=8.2, 1.0 Hz, 1H), 7.16 (d, J=8.7 Hz, 2H), 7.13-7.07 (m, 2H), 7.03-6.94 (m, 2H), 6.87 (dd, J=8.9, 4.6 Hz, 1H), 6.80 (dd, J=9.3, 3.1 Hz, 1H), 6.22 (t, J=1.0 Hz, 1H), 4.56 (d, J=17.8 Hz, 1H), 4.31 (d, J=18.0 Hz, 1H), 3.50 (dd, J=6.7, 3.5 Hz, 4H), 3.41 (dd, J=6.6, 3.5 Hz, 4H).

<Example 54> Preparation of (R)-6-(4-(4-acetylpiperazine-1-yl)phenyl)-2-((5-fluoro-2-hydroxyphenyl)(1H-indole-2-yl)methyl)-isoindolin-1-one LC-MS (M−H+) calcd for C35H31FN4O3 574.24, found 573.0.

<Example 55> Preparation of (R)-6-(4-(4-aminopiperazine-1-yl)phenyl)-2-((5-fluoro-2-hydroxyphenyl)(1H-indole-2-yl)methyl)-isoindolin-1-one 1H NMR (300 MHz, Methanol-d4) δ 8.01 (d, J=1.6 Hz, 1H), 7.85 (dd, J=8.0, 1.8 Hz, 1H), 7.62 (d, J=8.8 Hz, 2H), 7.58 (d, J=8.0 Hz, 1H), 7.49 (d, J=7.8 Hz, 1H), 7.38-7.32 (m, 1H), 7.17-7.06 (m, 3H), 7.04-6.94 (m, 2H), 6.87 (dd, J=8.9, 4.6 Hz, 1H), 6.80 (dd, J=9.3, 3.1 Hz, 1H), 6.22 (d, J=1.4 Hz, 1H), 4.55 (d, J=17.9 Hz, 1H), 4.30 (d, J=17.9 Hz, 1H), 3.91 (d, J=13.0 Hz, 2H), 2.91 (t, J=11.8 Hz, 2H), 2.12 (d, J=12.5 Hz, 2H), 1.80 (td, J=12.1, 4.0 Hz, 2H), 1.43-1.36 (m, 1H).

<Example 56> Preparation of (R)-6-(4-(4-aminopiperazine-1-yl)phenyl)-2-((5-chloro-2-hydroxyphenyl)(1H-indole-2-yl)methyl)-isoindolin-1-one 1H NMR (300 MHz, Methanol-d4) δ 8.01 (d, J=1.6 Hz, 1H), 7.85 (dd, J=8.0, 1.8 Hz, 1H), 7.60 (dd, J=12.0, 8.4 Hz, 3H), 7.49 (d, J=7.8 Hz, 1H), 7.35 (d, J=8.1 Hz, 1H), 7.22 (dd, J=8.6, 2.6 Hz, 1H), 7.16-7.07 (m, 3H), 7.05-7.00 (m, 2H), 6.88 (d, J=8.6 Hz, 1H), 6.22 (t, J=1.0 Hz, 1H), 4.56 (d, J=17.9 Hz, 1H), 4.30 (d, J=17.9 Hz, 1H), 3.92 (d, J=12.8 Hz, 2H), 2.92 (t, J=12.3 Hz, 2H), 2.11 (d, J=12.5 Hz, 2H), 1.89-1.70 (m, 2H), 1.44 15-1.26 (m, 1H).

<Example 57> Preparation of (R)-2-((5-fluoro-2-hydroxyphenyl)(1H-indole-2-yl)methyl)-6-(4-(4-(4-methylpiperazine-1-yl)piperidine-1-yl)phenyl)isoindolin-1-one 1H NMR (300 MHz, Methanol-d4) δ 8.07-8.01 (m, 1H), 7.88 (dd, J=8.0, 1.8 Hz, 1H), 7.73 (d, J=8.8 Hz, 2H), 7.61 (d, J=7.9 Hz, 1H), 7.49 (dt, J=7.7, 1.2 Hz, 1H), 7.39-7.32 (m, 3H), 7.15-7.06 (m, 3H), 7.05-6.94 (m, 2H), 6.88 (dd, J=8.8, 4.6 Hz, 1H), 6.80 (dd, J=9.3, 3.0 Hz, 1H), 6.22 (t, J=1.0 Hz, 1H), 4.57 (d, J=18.1 Hz, 1H), 4.32 (d, J=18.1 Hz, 1H), 3.90 (d, J=12.8 Hz, 2H), 3.18 (t, J=11.6 Hz, 6H), 2.89 (s, 3H), 2.18 (d, J=12.8 Hz, 2H), 1.91 (q, J=12.8, 12.1 Hz, 2H), 1.62 (s, 2H), 1.33-1.10 (m, 2H).

<Example 58> Preparation of (R)-2-((5-chloro-2-hydroxyphenyl)(1H-indole-2-yl)methyl)-6-(4-(4-(4-methylpiperazine-1-yl)piperidine-1-yl)phenyl)isoindolin-1-one 1H NMR (300 MHz, Methanol-d4) δ 8.03 (d, J=1.6 Hz, 1H), 7.88 (dd, J=8.0, 1.8 Hz, 1H), 7.71 (d, J=8.6 Hz, 2H), 7.61 (d, J=8.0 Hz, 1H), 7.49 (d, J=7.8 Hz, 1H), 7.33 (dd, J=10.9, 8.6 Hz, 3H), 7.23 (dd, J=8.6, 2.7 Hz, 1H), 7.14-7.08 (m, 2H), 7.05-6.98 (m, 2H), 6.89 (d, J=8.6 Hz, 1H), 6.22 (t, J=0.9 Hz, 1H), 4.58 (d, J=18.0 Hz, 1H), 4.30 (d, J=18.0 Hz, 1H), 3.91 (d, J=12.5 Hz, 2H), 3.11 (t, J=11.7 Hz, 5H), 2.87 (s, 3H), 2.16 (d, J=11.6 Hz, 2H), 1.96-1.80 (m, 3H), 1.63 (s, 1H), 1.21 (s, 2H), 0.91 (s, 1H).

<Example 59> Preparation of (R)-2-((5-fluoro-2-hydroxyphenyl)(1H-indole-2-yl)methyl)-6-(4-(4-(piperazine-1-yl)piperidine-1-yl)phenyl)isoindolin-1-one 1H NMR (300 MHz, Methanol-d4) δ 8.03 (d, J=1.7 Hz, 1H), 7.87 (dd, J=8.0, 1.7 Hz, 1H), 7.69 (d, J=8.7 Hz, 2H), 7.60 (d, J=8.0 Hz, 1H), 7.49 (d, J=7.8 Hz, 1H), 7.34 (d, J=8.1 Hz, 1H), 7.26 (d, J=8.7 Hz, 2H), 7.14-7.07 (m, 2H), 7.04-6.97 (m, 1H), 6.87 (dd, J=8.8, 4.6 Hz, 1H), 6.79 (dd, J=9.4, 3.1 Hz, 1H), 6.22 (t, J=0.9 Hz, 1H), 4.57 (d, J=18.0 Hz, 1H), 4.31 (d, J=18.0 Hz, 1H), 3.92 (d, J=12.4 Hz, 2H), 3.37 (d, J=5.3 Hz, 4H), 3.14 (s, 3H), 3.05 (t, J=12.7 Hz, 2H), 2.14 (d, J=12.5 Hz, 2H), 1.86 (d, J=12.6 Hz, 1H), 1.63 (s, 1H), 1.20 (s, 1H).

<Example 60> Preparation of (R)-2-((5-chloro-2-hydroxyphenyl)(1H-indole-2-yl)methyl)-6-(4-(4-(piperazine-1-yl)piperidine-1-yl)phenyl)isoindolin-1-one 1H NMR (300 MHz, Methanol-d4) δ 8.03-8.00 (m, 1H), 7.85 (dd, J=8.0, 1.7 Hz, 1H), 7.65 (d, J=8.7 Hz, 2H), 7.59 (d, J=8.0 Hz, 1H), 7.53-7.47 (m, 1H), 7.43-7.35 (m, 2H), 7.35-7.27 (m, 3H), 7.23 (dd, J=8.6, 2.6 Hz, 1H), 7.17-7.09 (m, 4H), 7.05-6.98 (m, 2H), 6.89 (d, J=8.6 Hz, 1H), 6.22 (t, J=1.0 Hz, 1H), 4.57 (d, J=17.9 Hz, 1H), 4.29 (d, J=18.0 Hz, 1H), 3.73 (d, J=13.1 Hz, 3H), 3.55 (s, 8H), 3.12 (d, J=12.6 Hz, 2H), 2.93 (s, 3H), 2.51 (d, J=13.6 Hz, 3H), 2.13 (d, J=13.2 Hz, 2H).

<Example 61> Preparation of (R)-6-(4-(4-(dimethylamino)piperidine-1-yl)phenyl)-2-((5-fluoro-2-hydroxyphenyl)(1H-indole-2-yl)methyl)-isoindolin-1-one 1H NMR (300 MHz, Methanol-d4) δ 8.03-8.00 (m, 1H), 7.85 (dd, J=8.0, 1.8 Hz, 1H), 7.62 (d, J=8.7 Hz, 2H), 7.58 (d, J=8.1 Hz, 1H), 7.49 (d, J=7.7 Hz, 1H), 7.37-7.27 (m, 2H), 7.15-7.07 (m, 3H), 7.04-6.94 (m, 2H), 6.87 (dd, J=8.8, 4.6 Hz, 1H), 6.80 (dd, J=9.3, 3.1 Hz, 1H), 6.22 (t, J=1.0 Hz, 1H), 4.56 (d, J=17.9 Hz, 1H), 4.30 (d, J=17.9 Hz, 1H), 4.00 (d, J=12.9 Hz, 2H), 3.46-3.39 (m, 1H), 2.93 (s, 6H), 2.86 (d, J=12.2 Hz, 2H), 2.20 (d, J=11.9 Hz, 2H), 1.96-1.76 (m, 3H).

<Example 62> Preparation of (R)-2-((5-chloro-2-hydroxyphenyl)(1H-indole-2-yl)methyl)-6-(4-(4-(dimethylamino)piperidine-1-yl)phenyl)-isoindolin-1-one LC-MS (M+H+) calcd for C36H35ClN4O2 590.24, found 591.1.

<Example 63> Preparation of (R)-2-((5-fluoro-2-hydroxyphenyl)(1H-indole-2-yl)methyl)-6-(4-(4-(piperidine-4-yl)piperazine-1-yl)phenyl)isoindolin-1-one 1H NMR (300 MHz, Methanol-d4) δ 8.04-7.98 (m, 1H), 7.86 (dd, J=8.0, 1.8 Hz, 1H), 7.71-7.64 (m, 2H), 7.59 (d, J=8.0 Hz, 1H), 7.49 (d, J=7.7 Hz, 1H), 7.34 (dd, J=8.1, 1.0 Hz, 1H), 7.16 (d, J=8.8 Hz, 2H), 7.13-7.06 (m, 1H), 7.05-6.94 (m, 2H), 6.87 (dd, J=8.9, 4.6 Hz, 1H), 6.80 (dd, J=9.3, 3.1 Hz, 1H), 6.22 (t, J=1.0 Hz, 1H), 4.56 (d, J=18.1 Hz, 1H), 4.31 (d, J=18.0 Hz, 1H), 3.70-3.49 (m, 11H), 3.20-3.07 (m, 2H), 2.48 (d, J=13.4 Hz, 2H), 2.11-1.93 (m, 1H), 1.65-1.20 (m, 2H).

<Example 64> Preparation of (R)-2-((5-chloro-2-hydroxyphenyl)(1H-indole-2-yl)methyl)-6-(4-(4-(piperidine-4-yl)piperazine-1-yl)phenyl)isoindolin-1-one 1H NMR (300 MHz, Methanol-d4) δ 8.05-7.98 (m, 1H), 7.86 (dd, J=8.0, 1.8 Hz, 1H), 7.66 (d, J=8.6 Hz, 2H), 7.59 (d, J=8.0 Hz, 1H), 7.49 (d, J=7.8 Hz, 1H), 7.35 (dd, J=8.1, 1.0 Hz, 1H), 7.22 (dd, J=8.6, 2.6 Hz, 1H), 7.19-7.07 (m, 4H), 7.05-6.98 (m, 2H), 6.89 (d, J=8.6 Hz, 1H), 6.26-6.16 (m, 1H), 4.57 (d, J=18.0 Hz, 1H), 4.29 (d, J=18.0 Hz, 1H), 3.71-3.48 (m, 11H), 3.13 (t, J=12.9 Hz, 2H), 2.48 (d, J=13.2 Hz, 2H), 2.10-1.95 (m, 2H).

<Example 65> Preparation of (R)-2-((5-fluoro-2-hydroxyphenyl)(1H-indole-2-yl)methyl)-6-(4-(4-(1-methylpiperidine-4-yl)piperazine-1-yl)phenyl)isoindolin-1-one 1H NMR (400 MHz, Methanol-d4) δ 7.99 (d, J=1.6 Hz, 1H), 7.83 (dd, J=8.0, 1.7 Hz, 1H), 7.62 (d, J=8.5 Hz, 2H), 7.56 (d, J=8.0 Hz, 1H), 7.49 (d, J=7.9 Hz, 1H), 7.35 (d, J=8.1 Hz, 1H), 7.11 (d, J=7.8 Hz, 4H), 7.04-6.94 (m, 2H), 6.88 (dd, J=8.9, 4.6 Hz, 1H), 6.79 (dd, J=9.3, 3.1 Hz, 1H), 6.22 (t, J=1.0 Hz, 1H), 4.54 (d, J=17.9 Hz, 1H), 4.28 (d, J=18.0 Hz, 1H), 3.71 (d, J=12.7 Hz, 2H), 3.53 (d, J=18.4 Hz, 9H), 3.13 (d, J=13.2 Hz, 2H), 2.92 (s, 3H), 2.48 (d, J=13.4 Hz, 2H), 2.16 (d, J=13.4 Hz, 2H).

<Example 66> Preparation of (R)-2-((5-chloro-2-hydroxyphenyl)(1H-indole-2-yl)methyl)-6-(4-(4-(1-methylpiperidine-4-yl)piperazine-1-yl)phenyl)isoindolin-1-one 1H NMR (300 MHz, Methanol-d4) δ 8.03-8.00 (m, 1H), 7.85 (dd, J=8.0, 1.7 Hz, 1H), 7.65 (d, J=8.7 Hz, 2H), 7.59 (d, J=8.0 Hz, 1H), 7.52-7.48 (m, 1H), 7.43-7.36 (m, 2H), 7.35-7.27 (m, 3H), 7.23 (dd, J=8.6, 2.6 Hz, 1H), 7.12 (ddd, J=12.6, 7.3, 1.9 Hz, 4H), 7.05-6.98 (m, 2H), 6.89 (d, J=8.6 Hz, 1H), 6.22 (t, J=1.0 Hz, 1H), 4.57 (d, J=17.9 Hz, 1H), 4.29 (d, J=18.0 Hz, 1H), 3.73 (d, J=13.1 Hz, 3H), 3.55 (s, 9H), 3.12 (d, J=12.6 Hz, 2H), 2.93 (s, 3H), 2.51 (d, J=13.6 Hz, 3H), 2.13 (d, J=13.2 Hz, 2H).

<Example 67> Preparation of (R)-2-((5-fluoro-2-hydroxyphenyl)(1H-indole-2-yl)methyl)-6-(4-(pyrrolidine-1-yl)phenyl)isoindolin-1-one 1H NMR (300 MHz, Methanol-d4) δ 8.03-7.97 (m, 1H), 7.84 (dd, J=8.0, 1.8 Hz, 1H), 7.60 (d, J=8.7 Hz, 2H), 7.55 (d, J=8.0 Hz, 1H), 7.51-7.45 (m, 1H), 7.34 (dd, J=8.1, 1.0 Hz, 1H), 7.13-7.06 (m, 2H), 7.04-6.99 (m, 1H), 6.99-6.93 (m, 1H), 6.87 (dd, J=8.8, 4.7 Hz, 1H), 6.80 (dd, J=9.2, 2.7 Hz, 3H), 6.22 (d, J=1.0 Hz, 1H), 4.54 (d, J=17.8 Hz, 1H), 4.29 (d, J=17.9 Hz, 1H), 3.46-3.37 (m, 4H), 2.17-2.05 (m, 4H).

<Example 68> Preparation of (R)-2-((5-chloro-2-hydroxyphenyl)(1H-indole-2-yl)methyl)-6-(4-(pyrrolidine-1-yl)phenyl)isoindolin-1-one 1H NMR (300 MHz, Methanol-d4) δ 8.03-7.97 (m, 1H), 7.84 (dd, J=8.0, 1.8 Hz, 1H), 7.60 (d, J=8.7 Hz, 2H), 7.55 (d, J=8.0 Hz, 1H), 7.51-7.45 (m, 1H), 7.34 (dd, J=8.1, 1.0 Hz, 1H), 7.13-7.06 (m, 2H), 7.04-6.99 (m, 1H), 6.99-6.93 (m, 1H), 6.87 (dd, J=8.8, 4.7 Hz, 1H), 6.80 (dd, J=9.2, 2.7 Hz, 3H), 6.22 (d, J=1.0 Hz, 1H), 4.54 (d, J=17.8 Hz, 1H), 4.29 (d, J=17.9 Hz, 1H), 3.46-3.37 (m, 4H), 2.17-2.05 (m, 4H).

<Example 69> Preparation of 6-(4-((R)-3-aminopyrrolidine-1-yl)phenyl)-2-((R)-(5-fluoro-2-hydroxyphenyl)(1H-indole-2-yl)methyl)isoindolin-1-one 1H NMR (300 MHz, Methanol-d4) δ 7.99 (d, J=1.6 Hz, 1H), 7.83 (dd, J=8.0, 1.7 Hz, 1H), 7.64-7.58 (m, 2H), 7.51 (dd, J=17.7, 7.9 Hz, 2H), 7.34 (d, J=8.1 Hz, 1H), 7.09 (d, J=7.2 Hz, 2H), 7.05-6.93 (m, 2H), 6.87 (dd, J=8.8, 4.6 Hz, 1H), 6.79 (td, J=6.1, 2.7 Hz, 2H), 6.21 (s, 1H), 4.54 (d, J=17.9 Hz, 1H), 4.29 (d, J=17.9 Hz, 1H), 4.07 (s, 1H), 3.71-3.59 (m, 2H), 3.47 (ddd, J=20.7, 10.0, 3.8 Hz, 2H), 2.51 (dq, J=14.8, 7.1 Hz, 1H), 2.20 (ddt, J=12.8, 8.1, 4.5 Hz, 1H).

<Example 70> Preparation of 6-(4-((R)-3-aminopyrrolidine-1-yl)phenyl)-2-((R)-(5-chloro-2-hydroxyphenyl)(1H-indole-2-yl)methyl)isoindolin-1-one 1H NMR (300 MHz, Methanol-d4) δ 8.00 (d, J=1.6 Hz, 1H), 7.84 (dd, J=8.0, 1.7 Hz, 1H), 7.62 (d, J=8.6 Hz, 2H), 7.57 (d, J=8.0 Hz, 1H), 7.49 (d, J=7.8 Hz, 1H), 7.35 (d, J=8.1 Hz, 1H), 7.22 (dd, J=8.6, 2.6 Hz, 1H), 7.14-7.07 (m, 2H), 7.05-6.98 (m, 2H), 6.88 (d, J=8.6 Hz, 1H), 6.79 (d, J=8.7 Hz, 2H), 6.22 (s, 1H), 4.55 (d, J=17.9 Hz, 1H), 4.28 (d, J=17.9 Hz, 1H), 4.08 (s, 1H), 3.66 (t, J=5.6 Hz, 2H), 3.56-3.41 (m, 2H), 2.53 (dd, J=14.8, 7.4 Hz, 1H), 2.21 (s, 1H).

<Example 71> Preparation of 6-(4-((S)-3-aminopyrrolidine-1-yl)phenyl)-2-((R)-(5-fluoro-2-hydroxyphenyl)(1H-indole-2-yl)methyl)isoindolin-1-one 1H NMR (300 MHz, Methanol-d4) δ 8.01-7.97 (m, 1H), 7.83 (dd, J=8.0, 1.8 Hz, 1H), 7.64-7.58 (m, 2H), 7.55 (d, J=8.0 Hz, 1H), 7.49 (dt, J=7.8, 1.1 Hz, 1H), 7.34 (dd, J=8.1, 1.0 Hz, 1H), 7.14-7.07 (m, 2H), 7.04-6.93 (m, 2H), 6.87 (dd, J=8.8, 4.6 Hz, 1H), 6.82-6.76 (m, 3H), 6.21 (t, J=1.0 Hz, 1H), 4.54 (d, J=17.9 Hz, 1H), 4.29 (d, J=17.9 Hz, 1H), 4.06 (d, J=3.4 Hz, 1H), 3.70-3.60 (m, 2H), 3.47 (ddd, J=19.7, 10.1, 3.8 Hz, 2H), 2.52 (ddt, J=13.6, 8.8, 6.7 Hz, 1H), 2.20 (ddt, J=12.9, 8.4, 4.7 Hz, 1H).

The chemical formulas of the compounds prepared in Examples 1-38 are summarized and shown in Table 1 below.

TABLE 1

| Example | Chemical Formula |
|---|---|
| 1 | 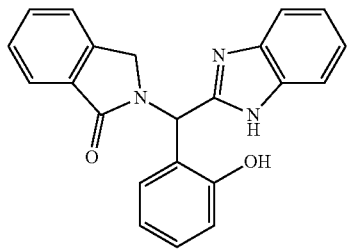 [SMILES: O=C1c2ccccc2CN1C(c1nc2ccccc2[nH]1)c1ccccc1O] |
| 2 | 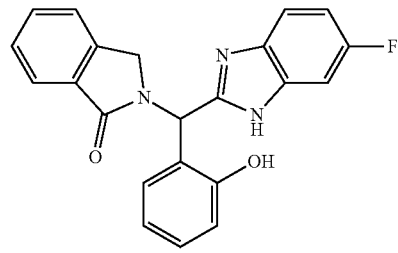 [SMILES: O=C1c2ccccc2CN1C(c1nc2ccc(F)cc2[nH]1)c1ccccc1O] |
| 3 | 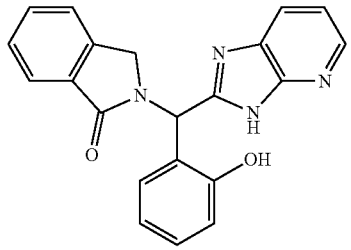 [SMILES: O=C1c2ccccc2CN1C(c1nc2cccnc2[nH]1)c1ccccc1O] |

TABLE 1-continued

| Example | Chemical Formula |
|---|---|
| 4 | |
| 5 | |
| 6 | |
| 7 | |
| 8 | |
| 9 | |

TABLE 1-continued
| Example | Chemical Formula |
|---|---|
| 10 | 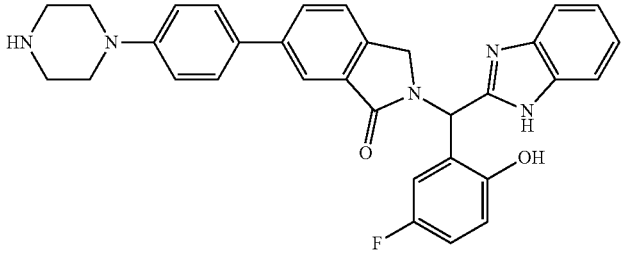 |
| 11 | 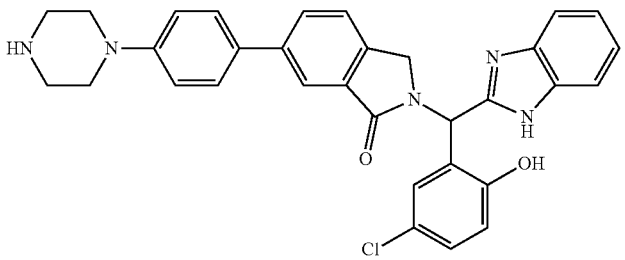 [SMILES: O=C1c2cc(-c3ccc(N4CCNCC4)cc3)ccc2CN1C(c1nc2ccccc2[nH]1)c1cc(F)ccc1O] |
| 12 | 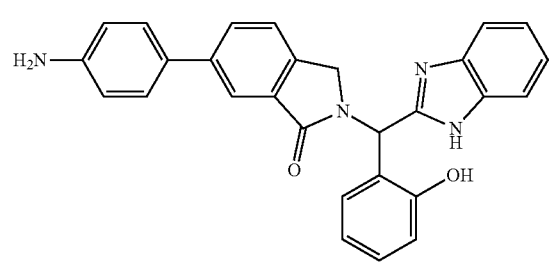 [SMILES: Nc1ccc(-c2ccc3c(c2)C(=O)N(C(c2nc4ccccc4[nH]2)c2ccccc2O)C3)cc1] |
| 13 | 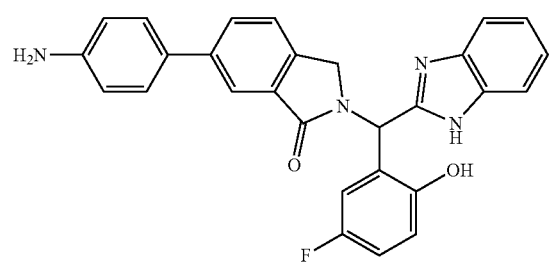 [SMILES: Nc1ccc(-c2ccc3c(c2)C(=O)N(C(c2nc4ccccc4[nH]2)c2cc(F)ccc2O)C3)cc1] |
| 14 | 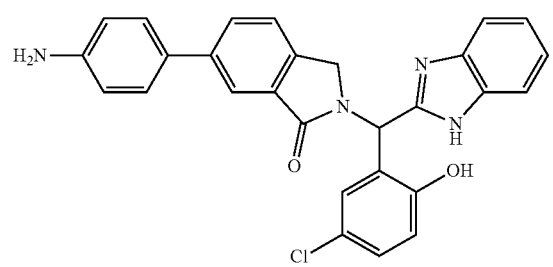 [SMILES: Nc1ccc(-c2ccc3c(c2)C(=O)N(C(c2nc4ccccc4[nH]2)c2cc(Cl)ccc2O)C3)cc1] |
| 15 | 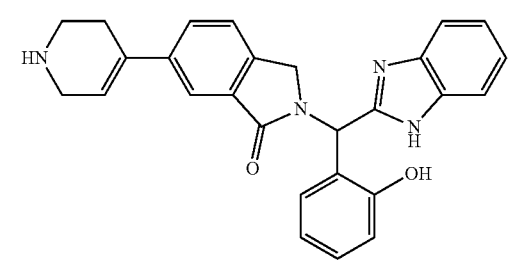 [SMILES: O=C1c2cc(C3=CCNCC3)ccc2CN1C(c1nc2ccccc2[nH]1)c1ccccc1O] |

TABLE 1-continued
| Example | Chemical Formula |
|---|---|
| 16 | 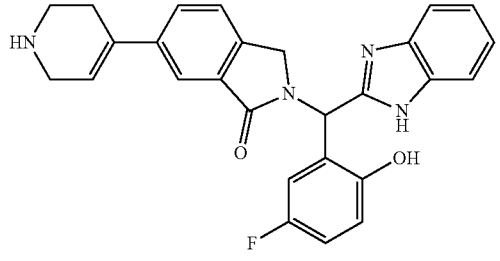 [SMILES: O=C1c2cc(C3=CCNCC3)ccc2CN1C(c1nc2ccccc2[nH]1)c1cc(F)ccc1O] |
| 17 | 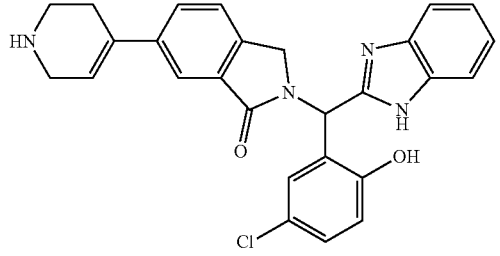 [SMILES: O=C1c2cc(C3=CCNCC3)ccc2CN1C(c1nc2ccccc2[nH]1)c1cc(Cl)ccc1O] |
| 18 | 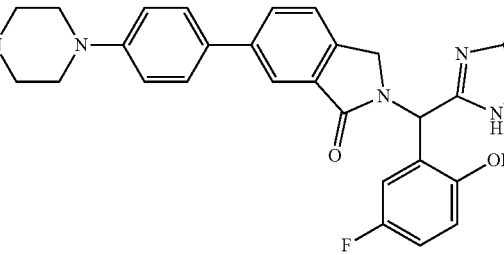 |
| 19 | 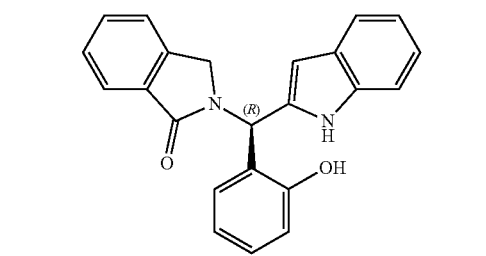 |
| 20 | 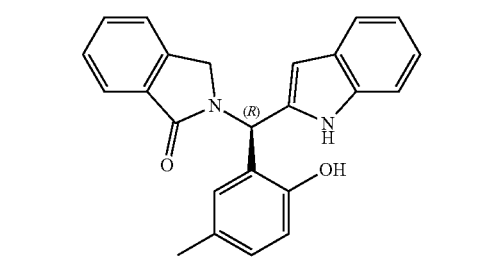 |
| 21 | 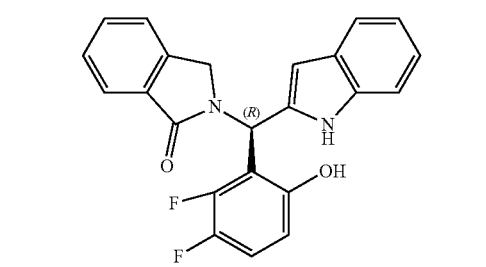 |

TABLE 1-continued

| Example | Chemical Formula |
|---|---|
| 22 | |
| 23 | |
| 24 | |
| 25 | |
| 26 | |
| 27 | |

TABLE 1-continued

| Example | Chemical Formula |
|---|---|
| 28 | |
| 29 | |
| 30 | |
| 31 | |
| 32 | |
| 33 | |

TABLE 1-continued

| Example | Chemical Formula |
|---|---|
| 34 | |
| 35 | |
| 36 | |
| 37 | |
| 38 | |

The chemical formulas of the compounds prepared in Examples 39-71 are summarized and shown in Table 2 below.

TABLE 2

| Example | Chemical Formula |
|---|---|
| 39 | |
| 40 | |
| 41 | |
| 42 | |
| 43 | |

TABLE 2-continued
| Example | Chemical Formula |
|---|---|
| 44 | 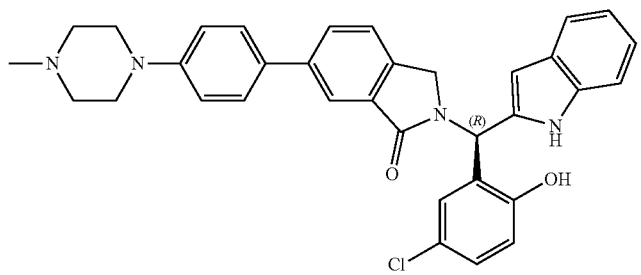 |
| 45 | 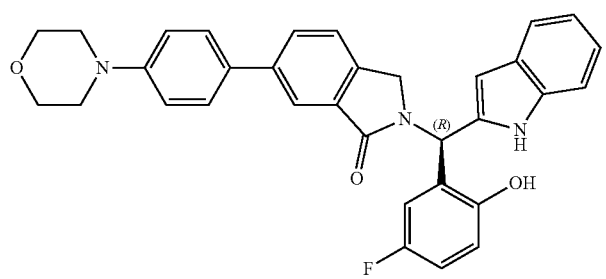 |
| 46 | 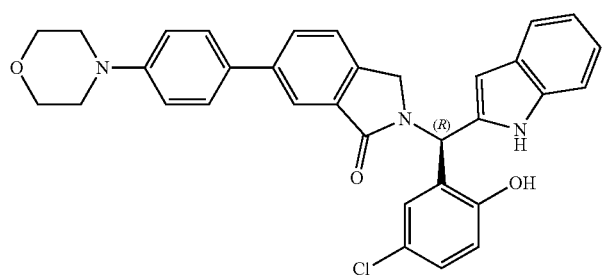 |
| 47 | 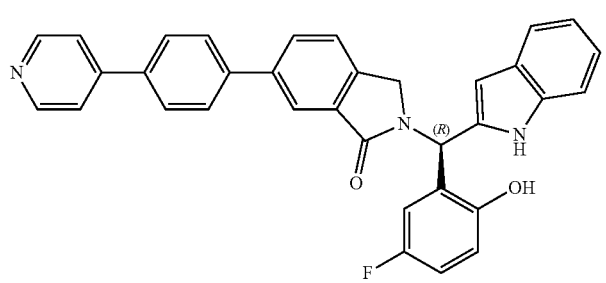 |
| 48 | 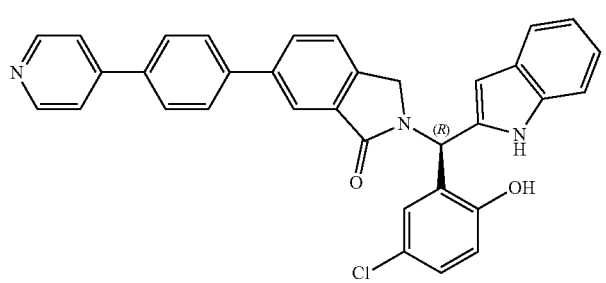 |

TABLE 2-continued
| Example | Chemical Formula |
|---|---|
| 49 | 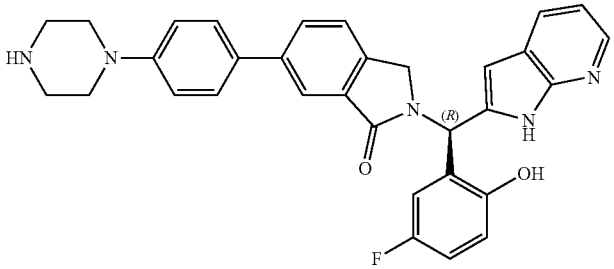 |
| 50 | 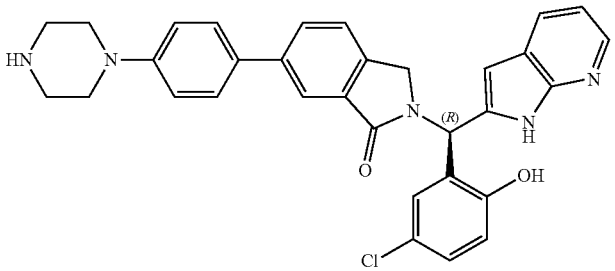 |
| 51 | 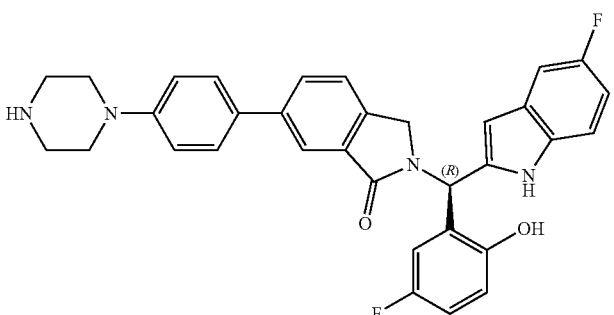 |
| 52 | 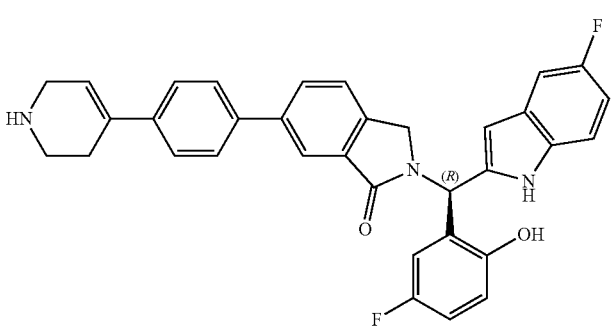 |
| 53 | 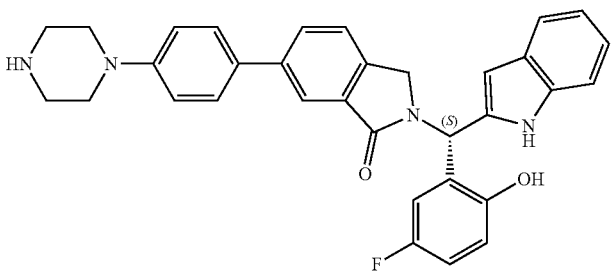 |

TABLE 2-continued

| Example | Chemical Formula |
|---|---|
| 54 | (structure) |
| 55 | (structure) |
| 56 | (structure) |
| 57 | (structure) |
| 58 | (structure) |
| 59 | (structure) |

TABLE 2-continued
| Example | Chemical Formula |
|---|---|
| 60 | 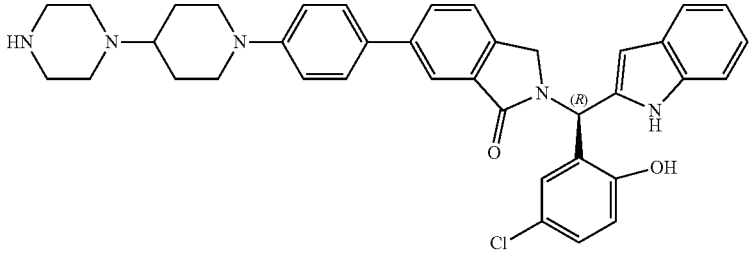 |
| 61 | 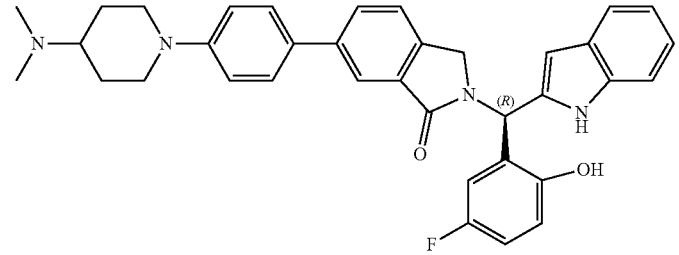 |
| 62 | 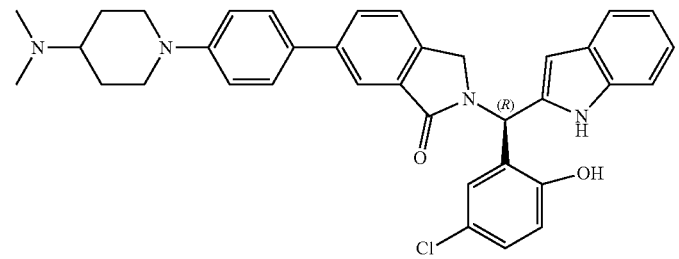 |
| 63 | 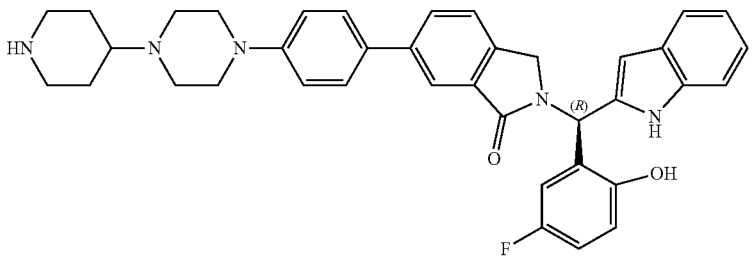 |
| 64 | 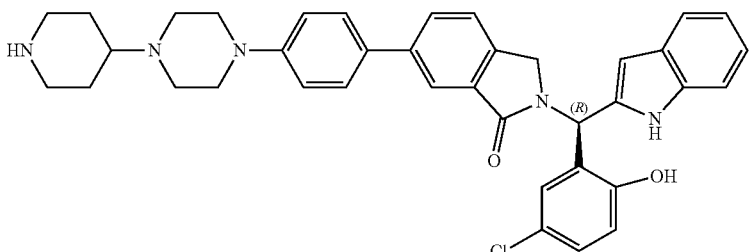 |
| 65 | 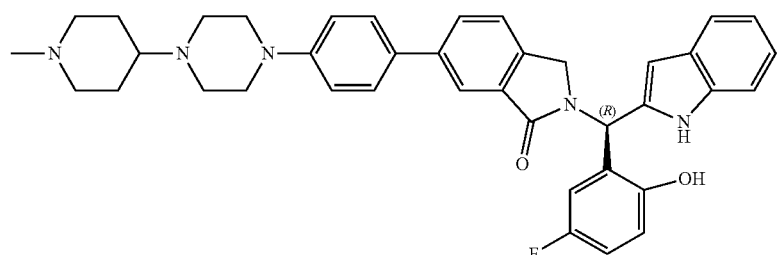 |

TABLE 2-continued

| Example | Chemical Formula |
|---|---|
| 66 | |
| 67 | |
| 68 | |
| 69 | |
| 70 | |
| 71 | |

<Experimental Example 1> Measurement of Inhibitory Activity of the Compound Represented by Formula 1 According to the Present Invention Against EGFR Mutation In order to evaluate the inhibitory activity of the compound represented by formula 1 according to the present invention against EGFR mutation, the following experiment was performed. The results are shown in Table 3 below.

The activity of the compound of the present invention against EGFR mutant enzyme was measured using the HTRF system of Cisbio Co. As an EGFR L858R/T790M/C797S mutant enzyme, a protein provided by SignalChem was purchased and used as an enzyme source.

The composition of the assay buffer used for the activity measurement was as follows: 50 mM Tris-HCl (pH 7.5), 100 mM NaCl, 7.5 mM $MgCl_2$, 3 mM KCl, 0.01% Tween 20, 0.1% BSA, and 1 mM DTT. Herein, an enzyme reaction was performed using a peptide substrate labeled with ATP at the concentration of 1 mM and biotin at the concentration of 0.5 µM. The analysis of the EGFR activity inhibitory effect of the compound was performed according to the following analytical reaction recipe.

Component 1: 4 µl of EGFR mutant enzyme
Component 2: 2 µl of compound solution
Component 3: 4 µl of ATP and biotin-labeled peptide mixture The enzyme reaction was initiated by mixing the component 1 and the component 2 first and then adding the component 3 thereto. After reacting the mixture at 37° C. for 2 hours, 10 µl of a measurement solution consisting of streptavidin-XL665 and europium-labeled anti-phosphotyrosine antibody provided by Cisbio was added to the enzyme reaction solution, followed by reaction at room temperature for 1 hour. Finally, the ratio of the fluorescence values at 615 nm and 665 nm was calculated using Envision equipment of Perkin-Elmer to quantitatively measure the enzyme activity and confirm the inhibitory ability of the compound. The values measured at 7 concentrations of the compound were analyzed using Prism program (version 5.01, Graphpad Software, Inc.), and the $IC_{50}$ value, an index of the inhibitory ability of the compound, was calculated.

TABLE 3

| Example | EGFR L858R/T790M/C797S $IC_{50}$ (µM) |
| --- | --- |
| 1 | 1 |
| 2 | 2.2 |
| 3 | 2.3 |
| 4 | 4.4 |
| 5 | 7 |
| 6 | >10 |
| 7 | 0.7 |
| 8 | 0.17 |
| 9 | 0.091 |
| 10 | 0.099 |
| 11 | 0.15 |
| 12 | 0.5 |
| 13 | 0.098 |
| 14 | 1.3 |
| 15 | 8.8 |
| 16 | 2.9 |
| 17 | 1.1 |
| 18 | 0.13 |
| 19 | >10 |
| 20 | 1.6 |
| 21 | >10 |
| 22 | >10 |
| 23 | 2.4 |
| 24 | 3.3 |
| 25 | >10 |
| 26 | 0.19 |
| 27 | 0.28 |
| 28 | 0.16 |
| 29 | 0.28 |
| 30 | 0.12 |
| 31 | 0.018 |
| 32 | 0.008 |
| 33 | 0.012 |
| 34 | 2.9 |
| 35 | 0.73 |
| 36 | 2.4 |
| 37 | >10 |
| 38 | 7.6 |
| 39 | 0.96 |
| 40 | 0.37 |
| 41 | 0.22 |
| 42 | 0.45 |
| 43 | 0.21 |
| 44 | 0.19 |
| 45 | 0.28 |
| 46 | 0.11 |
| 47 | 0.085 |
| 48 | >10 |
| 49 | 0.069 |
| 50 | 0.42 |
| 51 | 0.65 |
| 52 | >10 |
| 53 | 0.12 |
| 54 | 0.24 |
| 55 | 0.48 |
| 56 | 0.45 |
| 57 | 0.040 |
| 58 | 3.7 |
| 59 | 0.032 |
| 60 | 0.19 |
| 61 | 0.066 |
| 62 | 2.2 |
| 63 | 0.30 |
| 64 | 0.26 |
| 65 | 0.050 |
| 66 | 0.41 |
| 67 | 0.79 |
| 68 | 0.25 |
| 69 | 0.056 |
| 70 | 0.73 |
| 71 | 0.045 |

As shown in Table 3, the example compound of the present invention exhibited high inhibitory ability against EGFR L858R/T790M/C797S, a triple mutant of EGFR.

Therefore, the compound represented by formula 1 of the present invention was confirmed to have excellent effect of inhibiting EGFR L858R/T790M/C797S, a triple mutant of EGFR, and thus can be effectively used in the treatment of cancer, a disease related to EGFR mutation, and in particular, in the treatment of cancer expressing EGFR L858R/T790M/C797S.

<Experimental Example 2> Evaluation of Allosteric Inhibition Effect of the Compound Represented by Formula 1 According to the Present Invention on EGFR Wild-Type and Mutants in Ba/F3 Cell Lines and Evaluation of Cellular Activity According to Co-Administration In order to confirm that the compound represented by formula 1 according to the present invention acted as an allosteric inhibitor against EGFR wild-type and mutants, the inhibitory effect on EGFR wild-type and mutants in Ba/F3 cell lines was evaluated. In addition, in order to evaluate the cellular activity when the compound according to the present invention was co-administered with an existing drug, the cellular activity according to the combined administration was evaluated using Cetuximab used alone or in combination with chemotherapy in metastatic colorectal cancer and metastatic squamous head and neck cancer. The results are shown in FIGS. 1 to 7.

As the comparative control, EAI045 (Allosteric EGFR L858R/T790M inhibitor, CAS No. 1942114-09-1, 2-(5-fluoro-2-hydroxyphenyl)-2-(3-oxo-1H-isoindol-2-yl)-N-(1,3-thiazol-2-yl)acetamide) well known as an allosteric inhibitor against EGFR L858R/T790M was used.

Particularly, the activity of the compound of the present invention against the wild-type and mutant Ba/F3 EGFR cell lines was measured as follows using the CellTiter-Glo system of Promega. CellTiter-Glo assay is a method to confirm the cell viability by measuring ATP present in cells in cell culture state. Ba/F3 EGFR wild-type and Ba/F3 EGFR L858R, Ba/F3 EGFR L858R/T790M and Ba/F3 L858R/T790M/C797S mutant cell lines were purchased from Crown Bioscience and used. Ba/F3 EGFR wild-type and Ba/F3 EGFR L858R, Ba/F3 EGFR L858R/T790M and Ba/F3 L858R/T790M/C797S mutant cell lines were cultured in RPMI containing 10% FBS, 1% penicillin-streptomycin and 1 ug/ml of puromycine in a 37° C., 5% $CO_2$ incubator.

Analysis of the cell survival inhibitory effect of the compound according to each EGFR mutant was performed according to the following analytical reaction recipe.

BaF3 cells were aliquoted into 2500 cells/50 ul per well of a 96 well cell culture plate and cultured for 24 hours, to which 50 ul of the compound represented by formula 1 was treated at the concentrations of 0, 0.03, 0.1, 0.3, and 1 µM. The plate treated with the compound was reacted in a 37° C. incubator for 72 hours, and then left at room temperature for 30 minutes according to the CellTiter-Glo assay instruction to maintain the plate temperature at room temperature. Thereafter, 100 µl of CellTiter-Glo reagent was treated to each well of the plate, followed by shaking incubation at room temperature for 10 minutes. Finally, the ratio of the fluorescence values at 570 nm was quantitatively measured using a luminometer, and the ability of the compound to inhibit cell viability was confirmed. The values measured at concentrations of the compound were analyzed using Prism program (version 5.01, Graphpad Software, Inc.), and the $IC_{50}$ value, an index of the inhibitory ability of the compound, was calculated.

FIGS. 1-4 are graphs showing the evaluation results of the cell viability inhibitory effect of the allosteric inhibitors of Examples 9, 13, 32 and 33 on EGFR wild-type and mutants, respectively. The upper graphs show the survival rate of Ba/F3 cells when only the compound according to the present invention was treated as a tyrosine kinase inhibitor (TKI). The lower graphs show the survival rate of Ba/F3 cells when Cetuximab (Cet.) was treated in combination with the compound of the present invention (TKI in the graph). FIG. 1a, FIG. 2a, FIG. 3a, FIG. 4a: treated TKI alone, FIG. 1b, FIG. 2b, FIG. 3b, FIG. 4b: treated combined with Cetuximab FIG. 5 is a set of graphs showing the evaluation results of allosteric inhibitory effects of EAI045 on EGFR wild type and mutants. FIG. 5a: treated TKI alone, FIG. 5b: treated combined with Cetuximab FIG. 6 is a set of graphs showing the survival rate of Ba/F3 cells when 30 nM or 100 nM of the compounds of Examples 9, 13, 32 and 33 and EAI045 (EAI in the graph) were treated to the EGFR L858R/T790M mutants. FIG. 6a: treated with 30 nM, FIG. 6b: treated with 100 nM FIG. 7 is a set of graphs showing the survival rate of Ba/F3 cells when 30 nM or 100 nM of the compounds of Examples 9, 13, 32 and 33 and EAI045 (EAI in the graph) were treated to the EGFR L858R/T790M/C797S mutants. FIG. 7a: treated with 30 nM, FIG. 7b: treated with 100 nM As shown in FIGS. 1 to 4, when the compounds of Examples 9, 13, 32 and 33 of the present invention were administered alone, Ba/F3 cells expressing EGFR wild-type and mutants (EGFR L858R, EGFR L858R/T790M, EGFR del19/T790M/C797S, and EGFR L858R/T790M/C797S) showed similar degree of cell viability, and Ba/F3 cells expressing EGFR L858R/T790M showed increased cell viability after the administration.

On the other hand, when the compounds of the present invention were co-administered with Cetuximab, the cell viability of Ba/F3 cells expressing EGFR L858R/T790M and EGFR L858R/T790M/C797S was significantly reduced.

That is, the example compounds of the present invention exhibited a selective inhibitory effect on EGFR mutants than wild type, and particularly, among the mutants, exhibited remarkably excellent inhibitory effect on EGFR L858R/T790M and EGFR L858R/T790M/C797S.

Comparing the results of FIG. 5 and FIGS. 1 to 4, when co-administered with Cetuximab, the compounds of the present invention significantly reduced the cell viability of Ba/F3 cells expressing EGFR L858R/T790M and EGFR L858R/T790M/C797S compared to EAI045, a well known allosteric inhibitor to EGFR L858R/T790M. Therefore, it was confirmed that the compounds of the present invention exhibited superior effects to the conventional inhibitor.

As shown in FIGS. 6 and 7, when the compounds of Examples 9, 32 and 33 of the present invention were co-administered with Cetuximab, the compounds of the present invention significantly reduced the cell viability of Ba/F3 cells expressing EGFR L858R/T790M compared to EAI045, a well known allosteric inhibitor to EGFR L858R/T790M. Therefore, it was confirmed that the compounds of the present invention exhibited superior effects to the conventional inhibitor.

Accordingly, the compound represented by formula 1 according to the present invention exhibited higher inhibitory ability against EGFR mutations than EGFR wild type, and particularly, showed remarkably excellent inhibitory effect on EGFR L858R/T790M/C797S. Among the various EGFR mutations, the compound of the present invention selectively showed excellent inhibitory effect on EGFR L858R/T790M and EGFR L858R/T790M/C797S, so that the compound of the present invention can be effectively used in the treatment of cancer expressing EGFR L858R/T790M or EGFR L858R/T790M/C797S.

In addition, the compound of the present invention exhibited a significant synergistic effect when co-administered, and thus can be beneficially used in concomitant therapy.

<Manufacturing Example 1> Preparation of Powders

| | |
|---|---|
| Derivative represented by formula 1 | 2 g |
| Lactose | 1 g |

Powders were prepared by mixing all the above components, which were filled in airtight packs according to the conventional method for preparing powders.

\<Manufacturing Example 2\> preparation of tablets

| Derivative represented by formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

\<Manufacturing Example 3\> Preparation of Capsules

| Derivative represented by formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

\<Manufacturing Example 4\> Preparation of Injectable Solutions

| Derivative represented by formula 1 | 100 mg |
|---|---|
| Mannitol | 180 mg |
| $Na_2HPO_4 \cdot 2H_2O$ | 26 mg |
| Distilled water | 2974 mg |

Injectable solutions were prepared by containing all the above components in the amounts indicated according to the conventional method for preparing injectable solutions.

\<Manufacturing Example 5\> Preparation of Health Functional Foods

| Derivative represented by formula 1 | 500 ng |
|---|---|
| Vitamin complex | proper amount |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate | 15 mg |
| Calcium phosphate, dibasic | 55 mg |
| Potassium citrate | 90 mg |
| Calcium carbonate | 100 mg |
| Magnesium chloride | 24.8 mg |

The vitamins and minerals appropriate for health functional foods were mixed according to the preferred mixing ratio but the composition ratio can be adjusted arbitrarily. After mixing the above components according to the conventional method for preparing health functional foods, granules were prepared and the granules were used for the preparation of health functional foods according to the conventional method.

\<Manufacturing Example 6\> Preparation of Health Beverages

| Derivative represented by formula 1 | 500 ng |
|---|---|
| Citric acid | 1000 mg |
| Oligosaccharide | 100 g |
| Maesil (Prunus mume) Extract | 2 g |
| Taurine | 1 g |
| Purified water up to | 900 ml |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and ethnic preferences such as demand class, demand country, and purpose of use, etc.

INDUSTRIAL APPLICABILITY

The isoindolin-1-one derivative of the present invention can be effectively used in the treatment of cancers in which EGFR mutations have occurred, and can also be beneficially used in concomitant therapy.

What is claimed is:

1. A compound represented by formula 1, a stereoisomer thereof, a solvate thereof, a hydrate thereof or a pharmaceutically acceptable salt thereof:

[Formula 1]

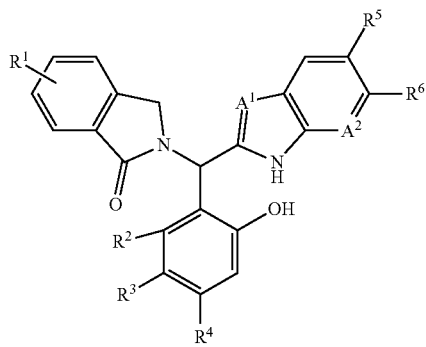

wherein,
$A^1$ is CH or N;
$A^2$ is CH or N;
$R^1$ is hydrogen, $C_{3-10}$ cycloalkyl, $C_{6-10}$ aryl, 3-10 membered heterocycloalkyl containing one or more heteroatoms selected from the group consisting of N, O and S, or 5-10 membered heteroaryl containing one or more heteroatoms selected from the group consisting of N, O and S, wherein the cycloalkyl and heterocycloalkyl may be unsaturated by including one double bond, cycloalkyl, aryl, heterocycloalkyl and heteroaryl can be independently substituted with one or more substituents selected from the group consisting of —NR$^a$R$^b$; straight or branched C$_{1-6}$ alkyl; acetyl; straight or branched C$_{1-6}$ alkylcarbonyl; straight or branched C$_{1-6}$ alkylaminocarbonyl; straight or branched C$_{1-6}$ alkylcarbonylamino; straight or branched C$_{1-6}$ alkylsulfonyl; saturated or unsaturated C$_{3-7}$ cycloalkyl including one double bond, which is nonsubstituted or substituted with one or more substituents selected from the group consisting of —N$^c$R$^d$, acetyl, straight or branched C$_{1-6}$ alkyl, straight or branched C$_{1-6}$ alkylcarbonyl, straight or branched C$_{1-6}$ alkylaminocarbonyl, straight or branched C$_{1-6}$ alkylcarbonylamino straight or branched C$_{1-6}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; saturated or unsaturated 3-7 membered heterocycloalkyl including one double bond and one or more heteroatoms selected from the group consisting of N, O and S, which is nonsubstituted or substituted with one or more substituents selected from the group consisting of —NR$^e$R$^f$, acetyl, straight or branched C$_{1-6}$ alkyl, straight or branched C$_{1-6}$ alkylcarbonyl, straight or branched C$_{1-6}$ alkylaminocarbonyl, straight or branched C$_{1-6}$ alkylcarbonylamino, straight or branched C$_{1-6}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S, wherein R$^a$, R$^b$, R$^c$, R$^d$, R$^e$ and R$^f$ are independently hydrogen, straight or branched C$_{1-6}$ alkyl or straight or branched C$_{1-6}$ alkylsulfonyl;

R$^2$, R$^3$ and R$^4$ are independently hydrogen, halogen or straight or branched C$_{1-6}$ alkyl, wherein the alkyl can be substituted with one or more halogens; and R$^5$ and R$^6$ are independently hydrogen, halogen or straight or branched C$_{1-6}$ alkyl, wherein the alkyl can be substituted with one or more halogens.

2. The compound, the stereoisomer thereof, the solvate thereof, the hydrate thereof or the pharmaceutically acceptable salt thereof according to claim 1, wherein:

R$^1$ is hydrogen, C$_{3-7}$ cycloalkyl, phenyl, 3-7 membered heterocycloalkyl containing one or more heteroatoms selected from the group consisting of N, O and S, or 5-8 membered heteroaryl containing one or more heteroatoms selected from the group consisting of N, O and S, wherein the cycloalkyl and heterocycloalkyl may be unsaturated by including one double bond, cycloalkyl, phenyl, heterocycloalkyl and heteroaryl can be independently substituted with one or more substituents selected from the group consisting of —NR$^a$R$^b$; straight or branched C$_{1-4}$ alkyl; acetyl; straight or branched C$_{1-4}$ alkylcarbonyl; straight or branched C$_{1-4}$ alkylaminocarbonyl; straight or branched C$_{1-4}$ alkylcarbonylamino; straight or branched C$_{1-4}$ alkylsulfonyl; saturated or unsaturated C$_{3-6}$ cycloalkyl including one double bond, which is nonsubstituted or substituted with one or more substituents selected from the group consisting of —NR$^c$R$^d$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; saturated or unsaturated 5 or 6 membered heterocycloalkyl including one double bond and one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —NR$^e$R$^f$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino, straight or branched C$_{1-4}$ alkylsulfonyl, and 5 or 6 membered heterocycloalkyl nonsubstituted or substituted with one or more straight or branched C$_{1-4}$ alkyl containing one or more heteroatoms selected from the group consisting of N, O and S, wherein R$^a$, R$^b$, R$^c$, R$^d$, R$^e$ and R$^f$ are independently hydrogen, straight or branched C$_{1-4}$ alkyl or straight or branched C$_{1-4}$ alkylsulfonyl.

3. The compound, the stereoisomer thereof, the solvate thereof, the hydrate thereof or the pharmaceutically acceptable salt thereof according to claim 1, wherein:

R$^1$ is hydrogen, C$_{5-6}$ cycloalkyl, phenyl, 5 or 6 membered heterocycloalkyl containing one or more heteroatoms selected from the group consisting of N, O and S, or 5 or 6 membered heteroaryl containing one or more heteroatoms selected from the group consisting of N, O and S, wherein the cycloalkyl and heterocycloalkyl may be unsaturated by including one double bond, cycloalkyl, phenyl, heterocycloalkyl and heteroaryl can be independently substituted with one or more substituents selected from the group consisting of —NR$^a$R$^b$; straight or branched C$_{1-4}$ alkyl; acetyl; straight or branched C$_{1-4}$ alkylcarbonyl; straight or branched C$_{1-4}$ alkylaminocarbonyl; straight or branched C$_{1-4}$ alkylcarbonylamino; straight or branched C$_{1-4}$ alkylsulfonyl; saturated or unsaturated C$_{5-6}$ cycloalkyl nonsubstituted or substituted with one or more substituents selected from the group consisting of —NR$^c$R$^d$, acetyl, straight or branched C$_{1-4}$ alkyl, straight or branched C$_{1-4}$ alkylcarbonyl, straight or branched C$_{1-4}$ alkylaminocarbonyl, straight or branched C$_{1-4}$ alkylcarbonylamino straight or branched C$_{1-4}$ alkylsulfonyl, and 5 or 6 membered heterocycloalkyl nonsubstituted or substituted with one or more straight or branched $C_{1-4}$ alkyl containing one or more heteroatoms selected from the group consisting of N, O and S; saturated or unsaturated 5 or 6 membered heterocycloalkyl containing one or more heteroatoms selected from the group consisting of N, O and S, which is nonsubstituted or substituted with one or more substituents selected from the group consisting of —$NR^eR^f$, acetyl, straight or branched $C_{1-4}$ alkyl, straight or branched $C_{1-4}$ alkylcarbonyl, straight or branched $C_{1-4}$ alkylaminocarbonyl, straight or branched $C_{1-4}$ alkylcarbonylamino, straight or branched $C_{1-4}$ alkylsulfonyl, and 5 or 6 membered heterocycloalkyl nonsubstituted or substituted with one or more straight or branched $C_{1-4}$ alkyl containing one or more heteroatoms selected from the group consisting of N, O and S; and 5 or 6 membered heteroaryl containing one or more heteroatoms selected from the group consisting of N, O and S, which is nonsubstituted or substituted with one or more substituents selected from the group consisting of —$NR^eR^f$, acetyl, straight or branched $C_{1-4}$ alkyl, straight or branched $C_{1-4}$ alkylcarbonyl, straight or branched $C_{1-4}$ alkylaminocarbonyl, straight or branched $C_{1-4}$ alkylcarbonylamino, straight or branched $C_{1-4}$ alkylsulfonyl, and 5 or 6 membered heterocycloalkyl nonsubstituted or substituted with one or more straight or branched $C_{1-4}$ alkyl containing one or more heteroatoms selected from the group consisting of N, O and S, wherein $R^a$, $R^b$, $R^c$, $R^d$, $R^e$ and $R^f$ are independently hydrogen, straight or branched $C_{1-4}$ alkyl or straight or branched $C_{1-4}$ alkylsulfonyl.

4. The compound, the stereoisomer thereof, the solvate thereof, the hydrate thereof or the pharmaceutically acceptable salt thereof according to claim 1, wherein:

$R^1$ is hydrogen, cyclohexyl, phenyl, tetrahydrofuranyl, morpholinyl, piperidinyl, piperazinyl, pyridinyl, pyrimidinyl, thiophenyl, quinolinyl, isoquinolinyl or quinazolinyl, wherein the cyclohexyl, tetrahydrofuranyl, morpholinyl, piperidinyl and piperazinyl may be unsaturated by including one double bond, cyclohexyl, phenyl, tetrahydrofuranyl, morpholinyl, piperidinyl, piperazinyl, pyridinyl, pyrimidinyl, thiophenyl, quinolinyl, isoquinolinyl and quinazolinyl can be independently substituted with one or more substituents selected from the group consisting of —$NR^aR^b$; straight or branched $C_{1-4}$ alkyl; acetyl; straight or branched $C_{1-4}$ alkylcarbonyl; straight or branched $C_{1-4}$ alkylaminocarbonyl; straight or branched $C_{1-4}$ alkylcarbonylamino; straight or branched $C_{1-4}$ alkylsulfonyl; saturated or unsaturated cyclohexyl including one double bond, which is nonsubstituted or substituted with one or more substituents selected from the group consisting of —$NR^cR^d$, acetyl, straight or branched $C_{1-4}$ alkyl, straight or branched $C_{1-4}$ alkylcarbonyl, straight or branched $C_{1-4}$ alkylaminocarbonyl, straight or branched $C_{1-4}$ alkylcarbonylamino and straight or branched $C_{1-4}$ alkylsulfonyl; saturated or unsaturated 5 or 6 membered heterocycloalkyl containing one double bond and one or more heteroatoms selected from the group consisting of N, O and S, which is nonsubstituted or substituted with one or more substituents selected from the group consisting of —$NR^eR^f$, acetyl, straight or branched $C_{1-4}$ alkyl, straight or branched $C_{1-4}$ alkylcarbonyl, straight or branched $C_{1-4}$ alkylaminocarbonyl, straight or branched $C_{1-4}$ alkylcarbonylamino, straight or branched $C_{1-4}$ alkylsulfonyl, piperidinyl nonsubstituted or substituted with one or more straight or branched $C_{1-4}$ alkyl, and piperazinyl nonsubstituted or substituted with one or more straight or branched $C_{1-4}$ alkyl; and 5 or 6 membered heteroaryl containing one or more heteroatoms selected from the group consisting of N, O and S, which is nonsubstituted or substituted with one or more substituents selected from the group consisting of —$NR^eR^f$, acetyl, straight or branched $C_{1-4}$ alkyl, straight or branched $C_{1-4}$ alkylcarbonyl, straight or branched $C_{1-4}$ alkylaminocarbonyl, straight or branched $C_{1-4}$ alkylcarbonylamino, straight or branched $C_{1-4}$ alkylsulfonyl, piperidinyl nonsubstituted or substituted with one or more straight or branched $C_{1-4}$ alkyl, and piperazinyl nonsubstituted or substituted with one or more straight or branched $C_{1-4}$ alkyl, wherein $R^a$, $R^b$, $R^c$, $R^d$, $R^e$ and $R^f$ are independently hydrogen, straight or branched $C_{1-4}$ alkyl or straight or branched $C_{1-4}$ alkylsulfonyl.

5. The compound, the stereoisomer thereof, the solvate thereof, the hydrate thereof or the pharmaceutically acceptable salt thereof according to claim 1, wherein:

$R^1$ is hydrogen, phenyl, piperidinyl or piperazinyl, wherein the piperidinyl may be unsaturated by including one double bond, phenyl, piperidinyl and piperazinyl can be independently substituted with one or more substituents selected from the group consisting of —$NR^aR^b$; straight or branched $C_{1-4}$ alkyl; and pyridinyl, pyrrolyl, piperidinyl, piperazinyl or morpholinyl nonsubstituted or substituted with one or more substituents selected from the group consisting of —$NR^eR^f$; acetyl; straight or branched $C_{1-4}$ alkyl; piperidinyl nonsubstituted or substituted with one or more straight or branched $C_{1-4}$ alkyl; and piperazinyl nonsubstituted or substituted with one or more straight or branched $C_{1-4}$ alkyl, wherein $R^a$, $R^b$, $R^e$ and $R^f$ are independently hydrogen or straight or branched $C_{1-4}$ alkyl.

6. The compound, the stereoisomer thereof, the solvate thereof, the hydrate thereof or the pharmaceutically acceptable salt thereof according to claim 1, wherein:

$R^1$ is hydrogen,

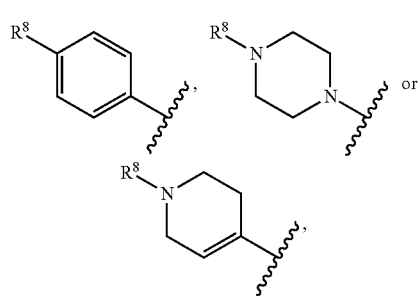

$R^8$ is independently hydrogen, —$NH_2$, straight or branched $C_{1-4}$ alkyl, pyridinyl, pyrrolyl, piperidinyl, piperazinyl or morpholinyl, wherein the pyridinyl, pyrrolyl, piperidinyl, piperazinyl and morpholinyl can be independently substituted with one or more substituents selected from the group consisting of —$NR^eR^f$; acetyl; straight or branched $C_{1-4}$ alkyl; piperidinyl nonsubstituted or substituted with one or more $C_{1-2}$ alkyl; and piperazinyl nonsubstituted or substituted with one or more $C_{1-2}$ alkyl, wherein $R^e$ and $R^f$ are independently hydrogen or straight or branched $C_{1-4}$ alkyl.

7. The compound, the stereoisomer thereof, the solvate thereof, the hydrate thereof or the pharmaceutically acceptable salt thereof according to claim 1, wherein:
R¹ is hydrogen,
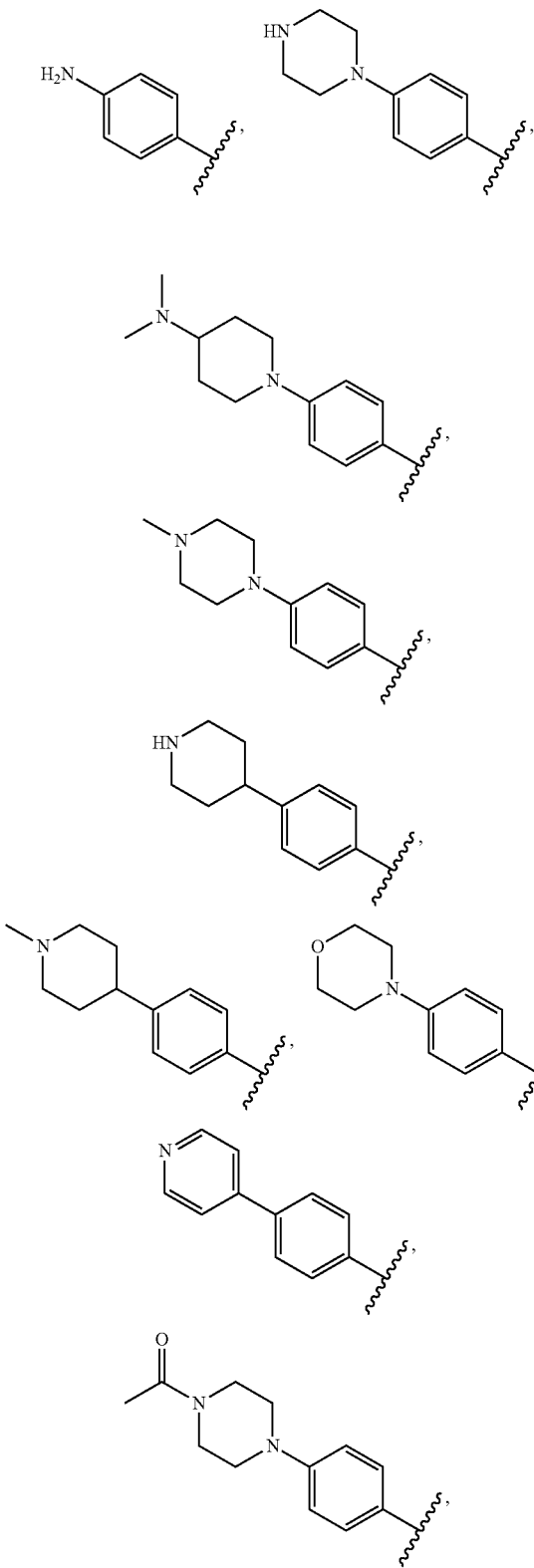
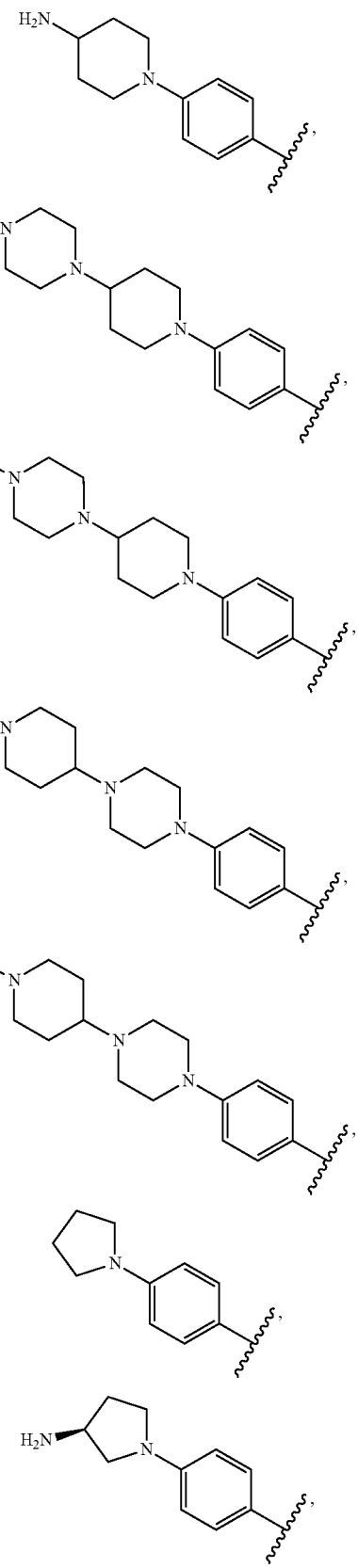

-continued

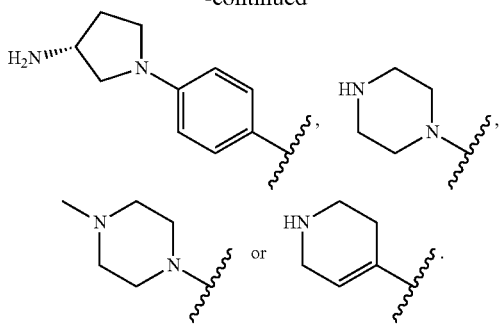

8. The compound, the stereoisomer thereof, the solvate thereof, the hydrate thereof or the pharmaceutically acceptable salt thereof according to claim 1, wherein:
$R^2$, $R^3$ and $R^4$ are independently hydrogen, halogen or straight or branched $C_{1-4}$ alkyl, wherein the alkyl can be substituted with one or more halogens; and
$R^5$ and $R^6$ are independently hydrogen, halogen or straight or branched $C_{1-4}$ alkyl, wherein the alkyl can be substituted with one or more halogens.

9. The compound, the stereoisomer thereof, the solvate thereof, the hydrate thereof or the pharmaceutically acceptable salt thereof according to claim 1, wherein:
$R^2$, $R^3$ and $R^4$ are independently hydrogen, halogen or $C_{1-2}$ alkyl, wherein the alkyl can be substituted with one or more halogens; and
$R^5$ and $R^6$ are independently hydrogen, halogen or $C_{1-2}$ alkyl, wherein the alkyl can be substituted with one or more halogens.

10. The compound, the stereoisomer thereof, the solvate thereof, the hydrate thereof or the pharmaceutically acceptable salt thereof according to claim 1, wherein:
$R^2$, $R^3$ and $R^4$ are independently hydrogen, F, Cl, $CH_3$ or $CF_3$; and
$R^5$ and $R^6$ are independently hydrogen, F or Cl.

11. The compound, the stereoisomer thereof, the solvate thereof, the hydrate thereof or the pharmaceutically acceptable salt thereof according to claim 1, wherein the compound represented by formula 1 is selected from the group consisting of the following compounds:

<1> 2-((1H-benzo[d]imidazole-2-yl)(2-hydroxyphenyl)methyl)isoindolin-1-one;
<2> 2-((6-fluoro-1H-benzo[d]imidazole-2-yl)(2-hydroxyphenyl)methyl)isoindolin-1-one;
<3> 2-((2-hydroxyphenyl)(3H-imidazo[4,5-b]pyridine-2-yl)methyl)isoindolin-1-one;
<4> 2-((6-chloro-1H-benzo[d]imidazole-2-yl)(2-hydroxyphenyl)methyl)isoindolin-1-one;
<5> 2-((5,6-dichloro-1H-benzo[d]imidazole-2-yl)(2-hydroxyphenyl)methyl)isoindolin-1-one;
<6> 2-((5-chloro-3H-imidazo[4,5-b]pyridine-2-yl)(2-hydroxyphenyl)methyl)isoindolin-1-one;
<7> 2-((1H-benzo[d]imidazole-2-yl)(5-fluoro-2-hydroxyphenyl)methyl)isoindolin-1-one;
<8> 2-((1H-benzo[d]imidazole-2-yl)(5-chloro-2-hydroxyphenyl)methyl)isoindolin-1-one;
<9> 2-((1H-benzo[d]imidazole-2-yl)(2-hydroxyphenyl)methyl)-6-(4-(piperazine-1-yl)phenyl)isoindolin-1-one;
<10> 2-((1H-benzo[d]imidazole-2-yl)(5-fluoro-2-hydroxyphenyl)methyl)-6-(4-(piperazine-1-yl)phenyl)isoindolin-1-one;
<11> 2-((1H-benzo[d]imidazole-2-yl)(5-chloro-2-hydroxyphenyl)methyl)-6-(4-(piperazine-1-yl)phenyl)isoindolin-1-one;
<12> 2-((1H-benzo[d]imidazole-2-yl)(2-hydroxyphenyl)methyl)-6-(4-aminophenyl)isoindolin-1-one;
<13> 2-((1H-benzo[d]imidazole-2-yl)(5-fluoro-2-hydroxyphenyl)methyl)-6-(4-aminophenyl)isoindolin-1-one;
<14> 2-((1H-benzo[d]imidazole-2-yl)(5-chloro-2-hydroxyphenyl)methyl)-6-(4-aminophenyl)isoindolin-1-one;
<15> 2-((1H-benzo[d]imidazole-2-yl)(2-hydroxyphenyl)methyl)-6-(1,2,3,6-tetrahydropyridine-4-yl)isoindolin-1-one;
<16> 2-((1H-benzo[d]imidazole-2-yl)(5-fluoro-2-methoxyphenyl)methyl)-6-(1,2,3,6-tetrahydropyridine-4-yl)isoindolin-1-one;
<17> 2-((1H-benzo[d]imidazole-2-yl)(5-chloro-2-methoxyphenyl)methyl)-6-(1,2,3,6-tetrahydropyridine-4-yl)isoindolin-1-one;
<18> 2-((1H-benzo[d]imidazole-2-yl)(5-fluoro-2-hydroxyphenyl)methyl)-6-(4-(4-methylpiperazine-1-yl)phenyl)isoindolin-1-one;
<19> (R)-2-((2-hydroxyphenyl)(1H-indole-2-yl)methyl)isoindolin-1-one;
<20> (R)-2-((2-hydroxy-5-methylphenyl)(1H-indole-2-yl)methyl)isoindolin-1-one;
<21> (R)-2-((2,3-difluoro-6-hydroxyphenyl)(1H-indole-2-yl)methyl)isoindolin-1-one;
<22> (R)-2-((4,5-difluoro-2-hydroxyphenyl)(1H-indole-2-yl)methyl)isoindolin-1-one;
<23> (R)-2-((5-fluoro-2-hydroxyphenyl)(1H-indole-2-yl)methyl)isoindolin-1-one;
<24> (S)-2-((5-fluoro-2-hydroxyphenyl)(1H-indole-2-yl)methyl)isoindolin-1-one;
<25> (R)-2-((2-fluoro-6-hydroxyphenyl)(1H-indole-2-yl)methyl)isoindolin-1-one;
<26> (R)-2-((5-chloro-2-hydroxyphenyl)(1H-indole-2-yl)methyl)isoindolin-1-one;
<27> (S)-2-((5-fluoro-2-hydroxyphenyl)(1H-pyrrolo[2,3-b]pyridine-2-yl)methyl)isoindolin-1-one;
<28> (R)-6-(4-aminophenyl)-2-((2-hydroxyphenyl)(1H-indole-2-yl)methyl)isoindolin-1-one;
<29> (R)-6-(4-aminophenyl)-2-((5-fluoro-2-hydroxyphenyl)(1H-indole-2-yl)methyl)isoindolin-1-one;
<30> (R)-6-(4-aminophenyl)-2-((5-chloro-2-hydroxyphenyl)(1H-indole-2-yl)methyl)isoindolin-1-one;
<31> (R)-2-((2-hydroxyphenyl)(1H-indole-2-yl)methyl)-6-(4-(piperazine-1-yl)phenyl)isoindolin-1-one;
<32> (R)-2-((5-fluoro-2-hydroxyphenyl)(1H-indole-2-yl)methyl)-6-(4-(piperazine-1-yl)phenyl)isoindolin-1-one;
<33> (R)-2-((5-chloro-2-hydroxyphenyl)(1H-indole-2-yl)methyl)-6-(4-(piperazine-1-yl)phenyl)isoindolin-1-one;
<34> (R)-2-((2-hydroxyphenyl)(1H-indole-2-yl)methyl)-6-(1,2,3,6-tetrahydropyridine-4-yl)isoindolin-1-one;
<35> (R)-2-((5-fluoro-2-hydroxyphenyl)(1H-indole-2-yl)methyl)-6-(1,2,3,6-tetrahydropyridine-4-yl)isoindolin-1-one;
<36> (R)-2-((5-chloro-2-hydroxyphenyl)(1H-indole-2-yl)methyl)-6-(1,2,3,6-tetrahydropyridine-4-yl)isoindolin-1-one;
<37> (R)-2-((5-fluoro-2-hydroxyphenyl)(1H-indole-2-yl)methyl)-6-(piperazine-1-yl)isoindolin-1-one;
<38> (R)-2-((5-fluoro-2-hydroxyphenyl)(1H-indole-2-yl)methyl)-6-(4-methylpiperazine-1-yl)isoindolin-1-one;

<39> 2-((1H-benzo[d]imidazole-2-yl)(5-fluoro-2-hydroxyphenyl)methyl)-6-(4-morpholinophenyl)isoindolin-1-one;
<40> 2-((1H-benzo[d]imidazole-2-yl)(5-chloro-2-hydroxyphenyl)methyl)-6-(4-morpholinophenyl)isoindolin-1-one;
<41> 2-((1H-benzo[d]imidazole-2-yl)(5-fluoro-2-hydroxyphenyl)methyl)-6-(4-(pyridine-4-yl)phenyl)isoindolin-1-one;
<42> 2-((1H-benzo[d]imidazole-2-yl)(5-chloro-2-hydroxyphenyl)methyl)-6-(4-(pyridine-4-yl)phenyl)isoindolin-1-one;
<43> (R)-2-((5-fluoro-2-hydroxyphenyl)(1H-indole-2-yl)methyl)-6-(4-(4-methylpiperazine-1-yl)phenyl)isoindolin-1-one;
<44> (R)-2-((5-chloro-2-hydroxyphenyl)(1H-indole-2-yl)methyl)-6-(4-(4-methylpiperazine-1-yl)phenyl)isoindolin-1-one;
<45> (R)-2-((5-fluoro-2-hydroxyphenyl)(1H-indole-2-yl)methyl)-6-(4-morpholinophenyl)isoindolin-1-one;
<46> (R)-2-((5-chloro-2-hydroxyphenyl)(1H-indole-2-yl)methyl)-6-(4-morpholinophenyl)isoindolin-1-one;
<47> (R)-2-((5-fluoro-2-hydroxyphenyl)(1H-indole-2-yl)methyl)-6-(4-(pyridine-4-yl)phenyl)isoindolin-1-one;
<48> (R)-2-((5-chloro-2-hydroxyphenyl)(1H-indole-2-yl)methyl)-6-(4-(pyridine-4-yl)phenyl)isoindolin-1-one;
<49> (R)-2-((5-fluoro-2-hydroxyphenyl)(1H-pyrrolo[2,3-b]pyridine-2-yl)methyl)-6-(4-(piperazine-4-yl)phenyl)isoindolin-1-one;
<50> (R)-2-((5-chloro-2-hydroxyphenyl)(1H-pyrrolo[2,3-b]pyridine-2-yl)methyl)-6-(4-(piperazine-4-yl)phenyl)isoindolin-1-one;
<51> (R)-2-((5-fluoro-1H-indole-2-yl)(5-fluoro-2-hydroxyphenyl)methyl)-6-(4-(piperazine-1-yl)phenyl)isoindolin-1-one;
<52> (R)-2-((5-fluoro-1H-indole-2-yl)(5-fluoro-2-hydroxyphenyl)methyl)-6-(4-(1,2,3,6-tetrahydropyridine-4-yl)phenyl)isoindolin-1-one;
<53> (S)-2-((5-fluoro-2-hydroxyphenyl)(1H-indole-2-yl)methyl)-6-(4-(piperazine-1-yl)phenyl)isoindolin-1-one;
<54> (R)-6-(4-(4-acetylpiperazine-1-yl)phenyl)-2-((5-fluoro-2-hydroxyphenyl)(1H-indole-2-yl)methyl)-isoindolin-1-one;
<55> (R)-6-(4-(4-aminopiperidine-1-yl)phenyl)-2-((5-fluoro-2-hydroxyphenyl)(1H-indole-2-yl)methyl)-isoindolin-1-one;
<56> (R)-6-(4-(4-aminopiperazine-1-yl)phenyl)-2-((5-chloro-2-hydroxyphenyl)(1H-indole-2-yl)methyl)-isoindolin-1-one;
<57> (R)-2-((5-fluoro-2-hydroxyphenyl)(1H-indole-2-yl)methyl)-6-(4-(4-(4-methylpiperazine-1-yl)piperidine-1-yl)phenyl)isoindolin-1-one;
<58> (R)-2-((5-chloro-2-hydroxyphenyl)(1H-indole-2-yl)methyl)-6-(4-(4-(4-methylpiperazine-1-yl)piperidine-1-yl)phenyl)isoindolin-1-one;
<59> (R)-2-((5-fluoro-2-hydroxyphenyl)(1H-indole-2-yl)methyl)-6-(4-(4-(piperazine-1-yl)piperidine-1-yl)phenyl)isoindolin-1-one;
<60> (R)-2-((5-chloro-2-hydroxyphenyl)(1H-indole-2-yl)methyl)-6-(4-(4-(piperazine-1-yl)piperidine-1-yl)phenyl)isoindolin-1-one;
<61> (R)-6-(4-(4-(dimethylamino)piperidine-1-yl)phenyl)-2-((5-fluoro-2-hydroxyphenyl)(1H-indole-2-yl)methyl)-isoindolin-1-one;
<62> (R)-2-((5-chloro-2-hydroxyphenyl)(1H-indole-2-yl)methyl)-6-(4-(4-(dimethylamino)piperidine-1-yl)phenyl)-isoindolin-1-one;
<63> (R)-2-((5-fluoro-2-hydroxyphenyl)(1H-indole-2-yl)methyl)-6-(4-(4-(piperidine-4-yl)piperazine-1-yl)phenyl)isoindolin-1-one;
<64> (R)-2-((5-chloro-2-hydroxyphenyl)(1H-indole-2-yl)methyl)-6-(4-(4-(piperidine-4-yl)piperazine-1-yl)phenyl)isoindolin-1-one;
<65> (R)-2-((5-fluoro-2-hydroxyphenyl)(1H-indole-2-yl)methyl)-6-(4-(4-(1-methylpiperidine-4-yl)piperazine-1-yl)phenyl)isoindolin-1-one;
<66> (R)-2-((5-chloro-2-hydroxyphenyl)(1H-indole-2-yl)methyl)-6-(4-(4-(1-methylpiperidine-4-yl)piperazine-1-yl)phenyl)isoindolin-1-one;
<67> (R)-2-((5-fluoro-2-hydroxyphenyl)(1H-indole-2-yl)methyl)-6-(4-(pyrrolidine-1-yl)phenyl)isoindolin-1-one;
<68> (R)-2-((5-chloro-2-hydroxyphenyl)(1H-indole-2-yl)methyl)-6-(4-(pyrrolidine-1-yl)phenyl)isoindolin-1-one;
<69> 6-(4-((R)-3-aminopyrrolidine-1-yl)phenyl)-2-((R)-(5-fluoro-2-hydroxyphenyl)(1H-indole-2-yl)methyl)isoindolin-1-one;
<70> 6-(4-((R)-3-aminopyrrolidine-1-yl)phenyl)-2-((R)-(5-chloro-2-hydroxyphenyl)(1H-indole-2-yl)methyl)isoindolin-1-one; and
<71> 6-(4-((S)-3-aminopyrrolidine-1-yl)phenyl)-2-((R)-(5-fluoro-2-hydroxyphenyl)(1H-indole-2-yl)methyl)isoindolin-1-one.

12. A method for preparing a compound represented by formula 1a comprising the following steps, as shown in reaction formula 1 below:

preparing a compound represented by formula 3 by reacting a compound represented by formula 5 with a compound represented by formula 4 (step 1);

preparing a compound represented by formula 2 by cyclization of the compound represented by formula 3 (step 2); and preparing a compound represented by formula 1a by reacting the compound represented by formula 2 (step 3):

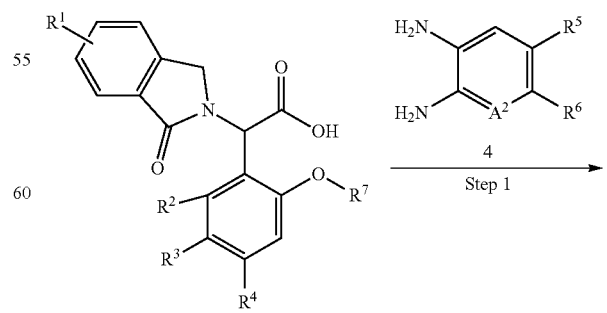

-continued

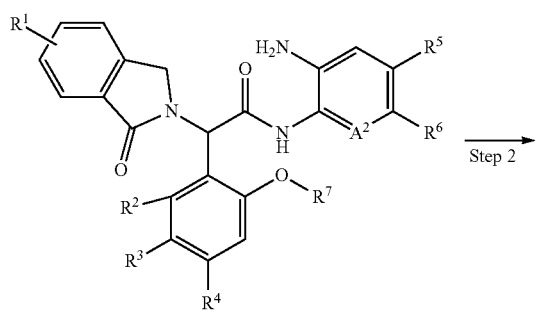

3

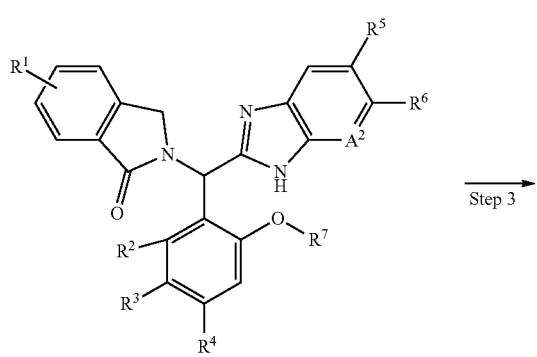

2

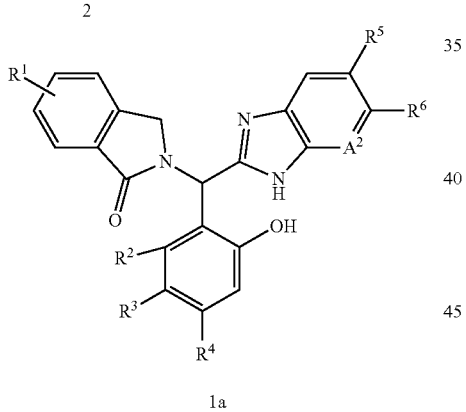

1a wherein,
A², R¹, R², R³, R⁴, R⁵ and R⁶ are as defined in formula 1 of claim 1;
R⁷ is straight or branched $C_{1-6}$ alkyl; and
the compound represented by formula 1a is a derivative when A¹ is N in the compound represented by formula 1 of claim 1.

13. A method for preparing a compound represented by formula 1b comprising the following steps, as shown in reaction formula 2 below:
preparing a compound represented by formula 6 by reacting a compound represented by formula 8 with a compound represented by formula 7 (step 1); and
preparing a compound represented by formula 1b by reacting the compound represented by formula 6 (step 2):

[Reaction Formula 2]

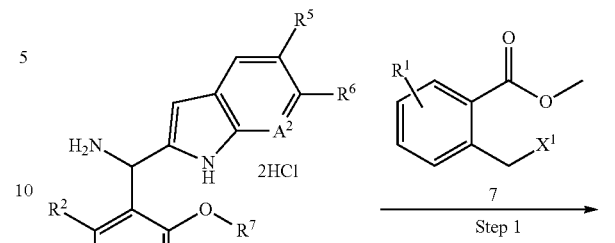

8

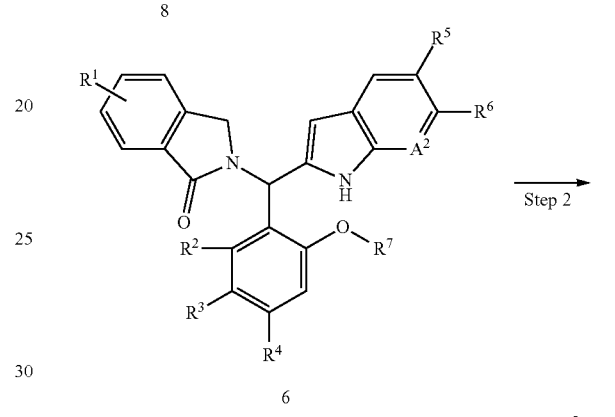

6

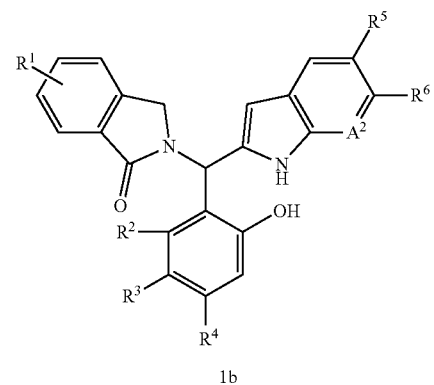

1b wherein
A², R¹, R², R³, R⁴, R⁵ and R⁶ are as defined in formula 1 of claim 1;
R⁷ is straight or branched $C_{1-6}$ alkyl;
X¹ is halogen; and
the compound represented by formula 1b is a derivative when A¹ is CH in the compound represented by formula 1 of claim 1.

14. A method of treating an EGFR-mutated cancer comprising administering a compound represented by formula 1 of claim 1, a stereoisomer thereof, a solvate thereof, a hydrate thereof or a pharmaceutically acceptable salt thereof as an active ingredient in a pharmaceutically effective amount to a subject in need thereof.

15. The method according to claim 14, wherein the compound inhibits EGFR (epidermal growth factor receptor) mutations.

16. The method according to claim 15, wherein the EGFR mutation is at least one selected from the group consisting of EGFR del19, EGFR del19/T790M, EGFR del19/T790M/C797S, EGFR L858R, EGFR L858R/T790M and EGFR L858R/T790M/C797S.

17. The method according to claim 14, wherein the EGFR-mutated cancer is at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lip cancer, mycelia, acute myelogenous leukemia, acute lymphocytic leukemia, basal cell cancer, ovarian epithelial carcinoma, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer and thymus cancer.

18. The method according to claim 14, wherein the compound acts as an allosteric inhibitor to EGFR (epidermal growth factor receptor).

19. The method according to claim 14, wherein the compound is administered in combination with an anticancer agent to enhance the anticancer effect.

* * * * *